United States Patent [19]
Wyvratt et al.

[11] Patent Number: 5,968,924
[45] Date of Patent: *Oct. 19, 1999

[54] BENZO-FUSED LACTAMS PROMOTE RELEASE OF GROWTH HORMONE

[75] Inventors: Matthew Wyvratt, Mountainside; Robert Devita, Westfield; Richard Bochis, East Brunswick; William Schoen, Edison, all of N.J.

[73] Assignee: Merck & Co., Inc., Rahway, N.J.

[ * ] Notice: This patent is subject to a terminal disclaimer.

[21] Appl. No.: 08/820,302

[22] Filed: Mar. 18, 1997

Related U.S. Application Data

[60] Division of application No. 08/392,961, Apr. 18, 1995, Pat. No. 5,672,596, which is a continuation-in-part of application No. 07/936,975, Aug. 28, 1992, Pat. No. 5,283,241.

[51] Int. Cl.$^6$ .................... C07D 243/10; C07D 267/02; C07D 281/02; A61K 31/55
[52] U.S. Cl. ............................................. 514/211; 540/491
[58] Field of Search .............................. 540/491; 514/211

[56] References Cited

U.S. PATENT DOCUMENTS

| | | | |
|---|---|---|---|
| 3,239,345 | 3/1966 | Hodge et al. | 99/3 |
| 4,036,979 | 7/1977 | Asato | 424/275 |
| 4,411,890 | 10/1983 | Momany | 244/177 |
| 4,692,522 | 9/1987 | Parsons et al. | 540/523 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |
| 5,374,721 | 12/1994 | Schoen et al. | 540/491 |
| 5,430,144 | 7/1995 | Schoen et al. | 540/461 |
| 5,434,261 | 7/1995 | Schoen et al. | 540/461 |
| 5,438,136 | 8/1995 | Devita et al. | |
| 5,583,130 | 12/1996 | Bochis et al. | 514/183 |

FOREIGN PATENT DOCUMENTS

| | | |
|---|---|---|
| 166357 | 1/1986 | European Pat. Off. . |
| 253310 | 1/1988 | European Pat. Off. . |
| 291969 | 11/1988 | European Pat. Off. . |
| 324377 | 7/1989 | European Pat. Off. . |
| 349949 | 1/1990 | European Pat. Off. . |

OTHER PUBLICATIONS

Jones, et al., *J. Chem. Soc.* c, 2176–2181 (1969), "N–Alkylaminoalkyl Derivatives of some Hexahydrobenzazocines".

Davis, et al., *Arch. Biochem. Biophys*, 102, 48–51 (1963), "The Synthesis . . . of o–Aminophenylalanine . . . ".

Wattley, et al., *J. Med. Chem.*, 28, 1511–1516 (1985), "Synthesis . . . of (Carboxyalkyl) amino–substituted Lactam Inhibitors . . ".

Slade, et al., *J. Med. Chem*, 28, 1517–1521 (1985), "Angiotensin Converting Enzyme Inhibitors . . . ".

Huang, et al., *Synthesis*, 10, 851 (1984), "Synthesis of 3–Oxo–3,4–dihydro–2H–1,4–benzoxazines . . . ".

Stewart, *Austalia J. Chem.*, 33, 633–640 (1980), "Synthesis of L–Kynurenine Peptides . . . ".

Still, et al., *J. Org. Chem.*, 43, 2923 (1978), "Rapid Chromatographic Technique . . . ".

Parsons, et al., *Med. Chem.*, 32, 1681–1685 (1989), "Cholecystokinin Antagonists . . . ".

Smith, et al., *Science*, 260, 1640–1643 (1993), "A Nonpeptidyl Growth Hormone Secretagogue".

*Primary Examiner*—Richard L. Raymond
*Assistant Examiner*—Bruck Kifle
*Attorney, Agent, or Firm*—J. Eric Thies; David L. Rose

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused lactams as the active ingredient thereof are also disclosed.

19 Claims, No Drawings

BENZO-FUSED LACTAMS PROMOTE RELEASE OF GROWTH HORMONE

This application is a division of Ser. No. 08/392,961, filed Apr. 18, 1995 now U.S. Pat. No. 5,672,596, which is a continuation-in-part of application Ser. No. 07/936,975, filed Aug. 28, 1992, now U.S. Pat. No. 5,283,241.

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

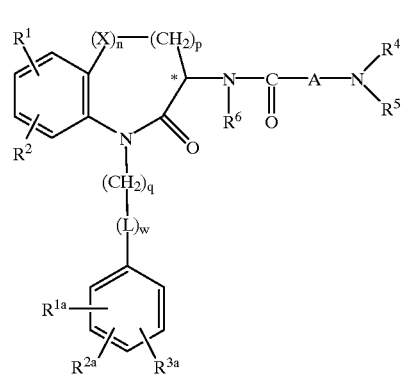

where L is

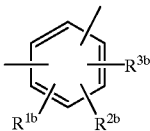

n is 0 or 1;
p is 0 to 3;
q is 0 to 4;
w is 0 or 1;

X is C=O, O, S(O)$_m$,

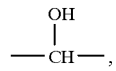

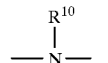

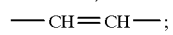

m is 0 to 2;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl or substituted phenyl; phenyl or substituted phenyl where the phenyl substituents are from 1 to 3 of halogen, $C_1$–$C_6$ alkyl, $C_1$–$C_6$ alkoxy, or hydroxy and v is 0 to 3;

$R^{3a}$ and $R^{3b}$ are independently hydrogen, $R^9$, $C_1$–$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is
$R^{4b}R^{12b}NCON(R^{12a})(CH_2)_v$—,
$R^{4b}R^{12b}NCSN(R^{12a})(CH_2)_v$—,
$R^{4b}R^{12c}NN(R^{12b})CSN(R^{12a})(CH_2)_v$—,
$R^{4b}R^{12c}NN(R^{12b})CON(R^{12a})(CH_2)_v$—,
$R^{4b}R^{12c}NN(R^{12b})COO(CH_2)_v$—, $R^{4b}R^{12b}NCOO(CH_2)_v$—
or $R^{13}OCON(R^{12a})(CH_2)_v$—, where v is 0 to 3.

$R^{12a}$, $R^{12b}$ and $R^{12c}$ are independently $R^{5a}$, $OR^{5a}$, or $COR^{5a}$. $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined.

$R^{13}$ is
$C_1$–$C_3$ perfluoroalkyl, $C_1$–$C_6$ alkyl, substituted $C_1$–$C_6$ alkyl, where the substitutents are hydroxy, $NR^{10}R^{11}$, carboxy, phenyl or substituted phenyl; phenyl or substituted phenyl where the subsfituents on the phenyl are from 1 to 3 of halogen, $C_1$–$C_6$ alkyl, $C_1$–$C_6$ alkoxy or hydroxy.
and v is as defined above;

$R^4$, $R^{4b}$, $R^5$ and $R^{5a}$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl, or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, fluoro, $R^1$, $R^2$ independently disubstituted phenyl $C_1$–$C_3$ alkoxy, $R^1$, $R^2$ independently disubstituted phenyl, $C_1$–$C_{20}$-alkanoyloxy, $C_1$–$C_5$ alkoxycarbonyl, carboxy, formyl or —$NR^{10}R^{11}$ where $R^{10}$ and $R^{11}$ are independently hydrogen, $C_1$–$C_6$ alkyl, phenyl, phenyl $C_1$–$C_6$ alkyl, $C_1$–$C_5$-alkoxycarbonyl or $C_1$–$C_5$-alkanoyl-$C_1$–$C_6$ alkyl; or $R^4$ and $R^5$ can be taken together to form —$(CH_2)_r$—B—$(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$–$C_{10}$ alkyl, phenyl or phenyl $C_1$–$C_{10}$ alkyl;

A is

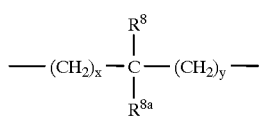

where x and y are independently 0–3;

$R^8$ and $R^{8a}$ are independently hydrogen, $C_1$–$C_{10}$ alkyl, trifluoromethyl, phenyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $C_3$–$C_7$ cycloalkyl, $R^1$, $R^2$ independently disubstituted phenyl $C_1$–$C_3$ alkoxy, $R^1$, $R^2$ independently disubstituted phenyl, $C_1$–$C_5$-alkanoyloxy, $C_1$–$C_5$ alkoxycarbonyl, carboxy, formyl, or —$NR^{10}R^{11}$ where $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
w is 0 or 1;

X is O, $S(O)_m$,

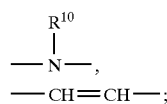

—CH=CH—;

m is 0 to 2;

$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$–$C_6$ alkyl, $C_1$–$C_6$ alkoxy or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl; phenyl and v is 0 to 2;

$R^{3a}$ and $R^{3b}$ are independently hydrogen, $R^9$, $C_1$–$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is
$R^{4b}R^{12b}NCON(R^{12a})(CH_2)_v$—,
$R^{4b}R^{12b}NCSN(R^{12a})(CH_2)_v$—,
$R^{4b}R^{12c}NN(R^{12b})CON(R^{12a})(CH_2)_v$—,
$R^{4b}R^{12}CNN(R^{12b})COO(CH_2)_v$—, $R^{4b}R^{12b}NCOO(CH_2)_v$— or $R^{13}OCON(R^{12a})(CH_2)_v$—, where v is 0 to 3.

$R^{12a}$, $R^{12b}$ and $R^{12c}$ are independently $R^{5a}$, $OR^{5a}$, or $COR^{5a}$. $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl.

$R^{13}$ is
$C_1$-$C_3$ perfluoroalkyl, $C_1$-$C_6$ alkyl, substituted $C_1$-$C_6$ alkyl, where the substituents are hydroxy, $NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

where v is as defined above;

$R^4$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, where the substituents on the alkyl or phenyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$-alkanoyloxy, $C_1$-$C_5$ alkoxycarbonyl, carboxy or formyl;

$R^4$ and $R^5$ can be taken together to form —$(CH_2)_r$—B—$(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;

A is

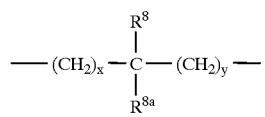

where x and y are independently 0–2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy, formyl, —$NR^{10}R^{11}$ where $R^{10}$ and $R^{11}$ are independently hydrogen, $C_1$-$C_6$ alkyl or $C_1$-$C_5$ alkanoyl-$C_1$-$C_6$ alkyl;

or $R^8$ and $R^{8a}$ can be taken together to form —$(CH_2)_t$— where t is 2 to 4;

and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Additional preferred compounds are realized in the above structural formula when:

n is 0 or 1;
p is 0 to 2;
q is 0 to 2;
w is 0 or 1;
X is $S(O)_m$ or —CH=CH—;
m is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl or substituted $C_1$-$C_6$ alkyl where the substituents are phenyl and v is 0 to 2;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$ with the proviso that either $R^{3a}$ or $R^{3b}$ must be a substituent other than hydrogen;

$R^9$ is
$R^{4b}R^{12b}NCON(R^{12a})(CH_2)_v$—,
$R^{4b}R^{12b}NCSN(R^{12a})(CH_2)_v$—,
$R^{4b}R^{12c}NN(R^{12b})CON(R^{12a})(CH_2)_v$—,
$R^{4b}R^{12c}NN(R^{12b})COO(CH_2)_v$—,
$R^{4b}R^{12b}NCOO(CH_2)_v$— or $R^{13}OCON(R^{12a})(CH_2)_v$—, where v is 0 to 2.

$R^{12a}$, $R^{12b}$ and $R^{12c}$ are independently $R^{5a}$, $OR^{5a}$, or $COR^{5a}$. $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$-$C_6$ alkyl or $C_1$-$C_5$ alkanoyl-$C_1$-$C_6$ alkyl;

$R^{13}$ is
$C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4b}$, $R^5$ and $R^{5a}$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, fluoro, $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;

A is

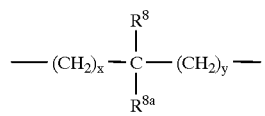

where x and y are independently 0–2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Still further preferred compounds of the instant invention are realized in the above structural formula when;

n is 0 or 1;
p is 0 to 2;

q is 1;
w is 1;
X is S(O)$_m$ or —CH=CH—;
m is 0 or 1;
R$^1$, R$^2$, R$^{1a}$, R$^{2a}$, R$^{1b}$ and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, phenyl or substituted phenyl where the substituents are from 1 to 3 of halogen, C$_1$–C$_6$ alkyl, C$_1$–C$_6$ alkoxy or hydroxy;
R$^{7a}$ and R$^{7b}$ are independently hydrogen, C$_1$–C$_6$ alkyl, substituted C$_1$–C$_6$ alkyl, where the substituents are phenyl and v is 0 or 1;
R$^{3a}$ and R$^{3b}$ are independently hydrogen, R$^9$, or C$_1$–C$_6$ alkyl substituted with R$^9$ with the proviso that either R$^{3a}$ or R$^{3b}$ must be a substituent other than hydrogen;
R$^9$ is
R$^{4b}$R$^{12b}$NCON(R$^{12a}$)(CH$_2$)$_v$—,
R$^{4b}$R$^{12c}$NN(R$^{12b}$)CON(R$^{12a}$)(CH$_2$)$_v$—,
R$^{4b}$R$^{12c}$NN(R$^{12b}$)COO(CH$_2$)$_v$—,
R$^{4b}$R$^{12b}$NCOO(CH$_2$)$_v$— or R$^{13}$OCON(R$^{12a}$)(CH$_2$)$_v$—,
where v is 0 or 1.
R$^{12a}$, R$^{12b}$ and R$^{12c}$ are independently R$^{5a}$, OR$^{5a}$, or COR$^{5a}$. R$^{12a}$ and R$^{12b}$, or R$^{12b}$ and R$^{12c}$, or R$^{12a}$ and R$^{12c}$, or R$^{12b}$ and R$^{4b}$, or
R$^{12c}$ and R$^{4b}$, or R$^{13}$ and R$^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above and R$^{10}$ is hydrogen, C$_1$–C$_6$ alkyl or C$_1$–C$_5$ alkanoyl-C$_1$–C$_6$ alkyl;
R$^{13}$ is
C$_1$–C$_6$ alkyl, substituted C$_1$–C$_6$ alkyl, where the substituents are phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;
R$^4$, R$^{4b}$, R$^5$ and R$^{5a}$ are independently hydrogen, C$_1$–C$_{10}$ alkyl, substituted C$_1$–C$_{10}$ alkyl, where the substituents on the alkyl are from 1 to 3 of hydroxy, C$_1$–C$_3$ alkoxy, fluoro, R$^1$, R$^2$ independently disubstituted phenyl, C$_1$–C$_{20}$ alkanoyloxy, C$_1$–C$_5$ alkoxycarbonyl or carboxy;
R$^6$ is hydrogen;
A is

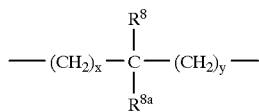

where x and y are independently 0–1;
R$^8$ and R$^{8a}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$, R$^2$ independently disubstituted phenyl, C$_1$–C$_5$-alkanoyloxy, C$_1$–C$_5$ alkoxycarbonyl, carboxy; or R$^8$ and R$^{8a}$ can be taken together to form —(CH$_2$)$_t$— where t is 2; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms;
and pharmaceutically acceptable salts thereof.
Representative preferred growth hormone releasing compounds of the present invention include the following:

1. N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3-methylbutanamide;
2. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
3. N-[1-[[2'-[(Ethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
4. N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
5. N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
6. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide;
7. N-[1-[[2'-[(Piperazinocarbonyl)amino][1,1'-biphenyl]-4-yl]methyl]-2,3,4,5-tetrahydro-2-oxo-1H-1-benzazepin-3(R)-yl]-3-amino-3-methylbutanamide;
8. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
9. N-[1-[[2'-[[(2-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
10. N-[1-[[2'-[(Methylaminocarbonyl)oxy][1,1-biphenyl]-4-yl]methyl]-2,3,4,5-tetrahydro-2-oxo-1H-1-benzazepin-3(R)-yl]-3-amino-3-methylbutanamide;
11. N-[1-[[2'-[(Dimethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
12. N-[1-[[2'-[[(2(R)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
13. N-[1-[[2'-[[(2(S)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
14. N-[1-[[2'-[[[[1-Hydroxyprop-2(R)-yl]amino]carbonyl]amino][1,1'-biphenyl]-4-yl]methyl]-2,3,4,5-tetrahydro-2-oxo-1H-1-benzazepin-3(R)-yl]-3-amino-3-methylbutanamide;
15. N-[1-[[2'-[4-[(Methylaminocarbonyl)amino]phenoxy][1,1'-biphenyl]-4-yl]methyl]-2,3,4,5-tetrahydro-2-oxo-1H-1-benzazepin-(R)-yl]-3-amino-3-methylbutanamide;
16. N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide;
17. N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide;
18. N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;
19. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide;
20. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(S)-hydroxypropyl]amino-3-methylbutanamide;

21. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;
22. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide;
23. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;
24. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide;
25. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(S)-hydroxypropyl]amino-3-methylbutanamide;
26. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;
27. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-2-amino-2-methylpropanamide;
28. N-[1-[[2'-[(Aminocarbonyl)amino][1,1'-biphenyl]-4-yl]methyl]-2,3,4,5-tetrahydro-2-oxo-1H-1-benzazepin-3(R)-yl]-2-amino-2-methylpropanamide;
29. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-2-amino-2-methylpropanamide;
30. N-[1-[[2'-[(Piperazinocarbonyl)amino][1,1'-biphenyl]-4-yl]methyl]-2,3,4,5-tetrahydro-2-oxo-1H-1-benzazepin-3(R)-yl]-2-amino-2-methylpropanamide;
31. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-2-amino-2-methylpropanamide;
32. N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-2-amino-2-methylpropanamide;
33. N-[1-[[2'-[[(Methoxycarbonylmethylamino)carbonyl]amino][1,1'-biphenyl]-4-yl]methyl]-2,3,4,5-tetrahydro-2-oxo-1H-1-benzazepin-3(R)-yl]-2-amino-2-methylpropanamide;
34. N-[1-[[2'-[(Hydroxyaminocarbonyl)amino][1,1'-biphenyl]-4-yl]methyl]-2,3,4,5-tetrahydro-2-oxo-1H-1-benzazepin-3(R)-yl]-2-amino-2-methylpropanamide;
35. N-[1-[[2'-[(Methoxycarbonyl)amino][1,1'-biphenyl]-4-yl]-methyl]-7-fluoro-2,3,4,5-tetrahydro-2-oxo-1H-1-benzazepin-3(R)-yl]-3-amino-3-methylbutanamide;
36. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-amino-3-methylbutanamide;
37. N-[1-[[2'-[(Methylaminocarbonyl)amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;
38. N-[1-[[2'-[(Morpholinocarbonyl)amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;
39. N-[1-[[2'-[[(2-Hydroxyethylamino)carbonyl]amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;
40. N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-3-amino-3-methylbutanamide;
41. N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-3-amino-3-methylbutanamide;
42. N-[1-[[2'-[2-[(Methylaminocarbonyl)amino]phenoxy][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;
43. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-[2(R)-hydroxypropyl]amino-3-methylbutanamide;
44. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-[2(S),3-dihydroxypropyl]amino-3-methylbutanamide;
45. N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-3-[2(R)-hydroxypropyl]amino-3-methylbutanamide;
46. N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-3-[2(S),3-dihydroxypropyl]amino-3-methylbutanamide;
47. N-[1-[[2'-[[(2-Hydroxyethylamino)carbonyl]amino][1,1'-biphenyl]4-yl]methyl]-7-fluoro-2,3,4,5-tetrahydro-2-oxo-1H-1-benzazepin-3(R)-yl]-3-[2(R)-hydroxypropyl]amino-3-methylbutanamide;
48. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide;
49. N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide;
50. N-[1-[[2'-[(Piperazinocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide;
51. N-[1-[[2'-[[(2-Hydroxyethylamino)carbonyl]amino][1,1'-biphenyl]-4-yl]methyl]-7-fluoro-2,3,4,5-tetrahydro-2-oxo-1-benzazepin-3(R)-yl]-2-amino-2-methylpropanamide;
52. N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-2-amino-2-methylpropanamide;
53. 2-Amino-2-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]propanamide;
54. 2-Amino-2-methyl-N-[2,3,4,5-tetrahydro-1-[[2'-[[[(methylamino)carbonyl]amino]methyl][1,1'-biphenyl]-4-yl]methyl]-7-fluoro-2-oxo-1H-benzazepin-3(R)-yl]propanamide;
55. 2-Amino-2-methyl-N-[2,3,4,5-tetrahydro-1-[[2'-[[[(methylamino)carbonyl]amino]methyl][1,1'-biphenyl]-4-yl]methyl]-7-methoxy-2-oxo-1H-benzazepin-3(R)-yl]propanamide;
56. 2-Amino-2-methyl-N-[2,3,4,5-tetrahydro-1-[[2'-[[[(methylamino)carbonyl]amino]methyl][1,1'-biphenyl]-4-yl]methyl]-7-methylthio-2-oxo-1H-benzazepin-3(R)-yl]propanamide;
57. 2-Amino-2-methyl-N-[2,3,4,5-tetrahydro-1-[[2'-[[[(methylamino)carbonyl]amino]methyl][1,1'-biphenyl]-4-yl]methyl]-7-trifluoromethyl-2-oxo-1H-benzazepin-3(R)-yl]propanamide;

58. 3-Amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;
59. 3-Amino-3-methyl-N-[2,3,4,5-tetrahydro-1-[[2'-[[[(methylamino)carbonyl]amino]methyl][1,1'-biphenyl]-4-yl]methyl]-7-fluoro-2-oxo-1H-benzazepin-3(R)-yl]butanamide;
60. 3-Amino-3-methyl —N-[2,3,4,5-tetrahydro-1-[[2'-[[[(methylamino)carbonyl]amino]methyl][1,1'-biphenyl]-4-yl]methyl]-7-methoxy-2-oxo-1H-benzazepin-3(R)-yl]butanamide;
61. 3-Amino-3-methyl-N-[2,3,4,5-tetrahydro-1-[[2'-[[[(methylamino)carbonyl]amino]methyl][1,1'-biphenyl]-4-yl]methyl]-7-methylthio-2-oxo-1H-benzazepin-3(R)-yl]butanamide;
62. 3-Amino-3-methyl-N-[2,3,4,5-tetrahydro--[[2'-[[[(methylamino)carbonyl]amino]methyl][1,1'-biphenyl]-4-yl]methyl]-7-trifluoromethyl-2-oxo-1H-benzazepin-3(R) -yl]butanamide;
63. 3-[2(R)-Hydroxypropylamino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;
64. 3-[2(R)-Hydroxypropyl]amino-3-methyl-N-[2,3,4,5-tetrahydro-1-[[2'-[[[(methylamino)carbonyl]amino]methyl][1,1'-biphenyl]-4-yl]methyl]-7-fluoro-2-oxo-1H-benzazepin-3(R)-yl]butanamide;
65. 3-[2(R)-Hydroxypropyl]amino-3-methyl-N-[2,3,4,5-tetrahydro-1-[[2'-[[[(methylamino)carbonyl]amino]methyl][1,1'-biphenyl]-4-yl]methyl]-7-methoxy-2-oxo-1H-benzazepin-3(R)-yl]butanamide;
66. 3-[2(R)-Hydroxypropylamino-3-methyl-N-[2,3,4,5-tetrahydro-1-[[2'-[[[(methylamino)carbonyl]amino]methyl][1,1'-biphenyl]-4-yl]methyl]-7-methylthio-2-oxo-1H-benzazepin-3(R)-yl]butanamide;
67. 3-[2(R)-Hydroxypropyl]amino-3-methyl-N-[2,3,4,5-tetrahydro-1-[[2'-[[[(methylamino)carbonyl]amino]methyl][1,1'-biphenyl]-4-yl]methyl]-7-trifluoromethyl-2-oxo-1H-benzazepin-3(R)-yl]butanamide;
68. 3-[2(S),3-Dihydroxypropyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide;
69. 3-[2(S),3-Dihydroxypropyl]amino-3-methyl —N-[2,3,4,5-tetrahydro-1-[[2'-[[[(methylamino)carbonyl]amino]methyl][1,1'-biphenyl]-4-yl]methyl]-7-fluoro-2-oxo-1H-benzazepin-3(R)-yl]butanamide;
70. 3-[2(S),3-Dihydroxypropyl]amino-3-methyl-N-[2,3,4,5-tetrahydro-1-[[2'-[[[(methylamino)carbonyl]amino]methyl][1,1'-biphenyl]4-yl]methyl]-7-methoxy-2-oxo-1H-benzazepin-3(R)-yl]butanamide;
71. 3-[2(S),3-Dihydroxypropyl]amino-3-methyl-N-[2,3,4,5-tetrahydro-1-[[2'-[[[(methylamino)carbonyl]amino]methyl][1,1'-biphenyl]-4-yl]methyl]-7-methylthio-2-oxo-1H-benzazepin-3(R)-yl]butanamide;
72. 3-[2(S),3-Dihydroxypropyl]amino-3-methyl-N-[2,3,4,5-tetrahydro-1-[[2'-[[[(methylamino)carbonyl]amino]methyl][1,1'-biphenyl]-4-yl]methyl]-7-trifluoromethyl-2-oxo-1H-benzazepin-3(R)-yl]butanamide;
73. 2-Amino-2-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]propanamide;
74. 2-Amino-2-methyl-N-[2,3,4,5-tetrahydro-1-[[2'-[[(aminocarbonyl)amino]methyl][1,1'-biphenyl]-4-yl]methyl]-7-fluoro-2-oxo-1H-benzazepin-3(R)-yl]propanamide;
75. 2-Amino-2-methyl-N-[2,3,4,5-tetrahydro-1-[[2'-[[(aminocarbonyl)amino]methyl][1,1'-biphenyl]-4-yl]methyl]-7-methoxy-2-oxo-1H-benzazepin-3(R)-yl]propanamide;
76. 2-Amino-2-methyl-N-[2,3,4,5-tetrahydro-1-[[2'-[[(aminocarbonyl)amino]methyl][1,1'-biphenyl]-4-yl]methyl]-7-methylthio-2-oxo-1H-benzazepin-3(R)-yl]propanamide;
77. 2-Amino-2-methyl-N-[2,3,4,5-tetrahydro-1-[[2'-[[(aminocarbonyl)amino]methyl][1,1'-biphenyl]-4-yl]methyl]-7-trifluoromethyl-2-oxo-1H-benzazepin-3(R)-yl]propanamide;
78. 3-Amino-3-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]butanamide;
79. 3-Amino-3-methyl-N-[2,3,4,5-tetrahydro-1-[[2'-[[(aminocarbonyl)amino]methyl][1,1'-biphenyl]-4-yl]methyl]-7-fluoro-2-oxo-1H-benzazepin-3(R)-yl]butanamide;
80. 3-Amino-3-methyl-N-[2,3,4,5-tetrahydro-1-[[2'-[[(aminocarbonyl)amino]methyl][1,1'-biphenyl]-4-yl]methyl]-7-methoxy-2-oxo-1H-benzazepin-3(R)-yl]butanamide;
81. 3-Amino-3-methyl-N-[2,3,4,5-tetrahydro-1-[[2'-[[(aminocarbonyl)amino]methyl][1,1'-biphenyl]-4-yl]methyl]-7-methylthio-2-oxo-1H-benzazepin-3(R)-yl]butanamide;
82. 3-Amino-3-methyl-N-[2,3,4,5-tetrahydro-1-[[2'-[[(aminocarbonyl)amino]methyl][1,1'-biphenyl]-4-yl]methyl]-7-trifluoromethyl-2-oxo-1H-benzazepin-3(R)-yl]butanamide;
83. 3-[2(R)-Hydroxypropyl]amino-3-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]butanamide;
84. 3-[2(R)-Hydroxypropyl]amino-3-methyl-N-[2,3,4,5-tetrahydro-1-[[2'-[[(aminocarbonyl)amino]methyl][1,1'-biphenyl]-4-yl]methyl]-7-fluoro-2-oxo-1H-benzazepin-3(R)-yl]butanamide;
85. 3-[2(R)-Hydroxypropyl]amino-3-methyl-N-[2,3,4,5-tetrahydro-1-[[2'-[[(aminocarbonyl)amino]methyl][1,1'-biphenyl]-4-yl]methyl]-7-methoxy-2-oxo-1H-benzazepin-3(R)-yl]butanamide;
86. 3-[2(R)-Hydroxypropyl]amino-3-methyl-N-[2,3,4,5-tetrahydro-1-[[2'-[[(aminocarbonyl)amino]methyl][1,1'-biphenyl]-4-yl]methyl]-7-methylthio-2-oxo-1H-benzazepin-3(R)-yl]butanamide;
87. 3-[2(R)-Hydroxypropyl]amino-3-methyl-N-[2,3,4,5-tetrahydro-1-[[2'-[[(aminocarbonyl)amino]methyl][1,1'-biphenyl]-4-yl]methyl]-7-trifluoromethyl-2-oxo-1H-benzazepin-3(R)-yl]butanamide;
88. 3-[2(S),3-Dihydroxypropyl]amino-3-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]butanamide;
89. 3-[2(S),3-Dihydroxypropyl]amino-3-methyl-N-[2,3,4,5-tetrahydro-1-[[2'-[[(aminocarbonyl)amino]methyl][1,1'-biphenyl]-4-yl]methyl]-7-fluoro-2-oxo-1H-benzazepin-3(R)-yl]butanamide;
90. 3-[2(S),3-Dihydroxypropyl]amino-3-methyl-N-[2,3,4,5-tetrahydro-1-[[2'-[[(aminocarbonyl)amino]methyl][1,1'-biphenyl]-4-yl]methyl]-7-methoxy-2-oxo-1H-benzazepin-3(R)-yl]butanamide;
91. 3-[2(S),3-Dihydroxypropyl]amino-3-methyl-N-[2,3,4,5-tetrahydro-1-[[2'-[[(aminocarbonyl)amino]methyl][1,1'-biphenyl]-4-yl]methyl]-7-methylthio-2-oxo-1H-benzazepin-3(R)-yl]butanamide;
92. 3-[2(S),3-Dihydroxypropyl]amino-3-methyl-N-[2,3,4,5-tetrahydro-1-[[2'-[[(aminocarbonyl)amino]methyl][1,1'-biphenyl]-4-yl]methyl]-7-trifluoromethyl-2-oxo-1H-benzazepin-3(R)-yl]butanamide;

93. 2-Amino-2-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]propanamide;

94. 2-Amino-2-methyl-N-[2,3,4,5-tetrahydro-1-[[2'-[[[(ethylamino)carbonyl]amino]methyl][1,1'-biphenyl]-4-yl]methyl]-7-fluoro-2-oxo-1H-benzazepin-3(R)-yl]propanamide;

95. 2-Amino-2-methyl-N-[2,3,4,5-tetrahydro-1-[[2'-[[[(ethylamino)carbonyl]amino]methyl][1,1'-biphenyl]-4-yl]methyl]-7-methoxy-2-oxo-1H-benzazepin-3(R)-yl]propanamide;

96. 2-Amino-2-methyl-N-[2,3,4,5-tetrahydro-1-[[2'-[[[(ethylamino)carbonyl]amino]methyl][1,1'-biphenyl]-4-yl]methyl]-7-methylthio-2-oxo-1H-benzazepin-3(R)-yl]propanamide;

97. 2-Amino-2-methyl-N-[2,3,4,5-tetrahydro-1-[[2'-[[[(ethylamino)carbonyl]amino]methyl][1,1'-biphenyl]-4-yl]methyl]-7-trifluoromethyl-2-oxo-1H-benzazepin-3(R)-yl]propanamide;

98. 3-Amino-3-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]butanamide;

99. 3-Amino-3-methyl-N-[2,3,4,5-tetrahydro-1-[[2'-[[[(ethylamino)carbonyl]amino]methyl][1,1'-biphenyl]-4-yl]methyl]-7-fluoro-2-oxo-1H-benzazepin-3(R)-yl]butanamide;

100. 3-Amino-3-methyl-N-[2,3,4,5-tetrahydro-1-[[2'-[[[(ethylamino)carbonyl]amino]methyl][1,1'-biphenyl]-4-yl]methyl]-7-methoxy-2-oxo-1H-benzazepin-3(R)-yl]butanamide;

101. 3-Amino-3-methyl-N-[2,3,4,5-tetrahydro-1-[[2'-[[[(ethylamino)carbonyl]amino]methyl][1,1'-biphenyl]-4-yl]methyl]-7-methylthio-2-oxo-1H-benzazepin-3(R)-yl]butanamide;

102. 3-Amino-3-methyl-N-[2,3,4,5-tetrahydro-1-[[2'-[[[(ethylamino)carbonyl]amino]methyl][1,1'-biphenyl]-4-yl]methyl]-7-trifluoromethyl-2-oxo-1H-benzazepin-3(R)-yl]butanamide;

103. 3-[2(R)-Hydroxypropyl]amino-3-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]butanamide;

104. 3-[2(R)-Hydroxypropyl]amino-3-methyl-N-[2,3,4,5-tetrahydro-1-[[2'-[[[(ethylamino)carbonyl]amino]methyl][1,1'-biphenyl]-4-yl]methyl]-7-fluoro-2-oxo-1H-benzazepin-3(R)-yl]butanamide;

105. 3-[2(R)-Hydroxypropyl]amino-3-methyl-N-[2,3,4,5-tetrahydro-1-[[2'-[[[(ethylamino)carbonyl]amino]methyl][1,1'-biphenyl]-4-yl]methyl]-7-methoxy-2-oxo-1H-benzazepin-3(R)-yl]butanamide;

106. 3-[2(R)-Hydroxypropyl]amino-3-methyl-N-[2,3,4,5-tetrahydro-1-[[2'-[[[(ethylamino)carbonyl]amino]methyl][1,1'-biphenyl]4-yl]methyl]-7-methylthio-2-oxo-1H-benzazepin-3(R)-yl]butanamide;

107. 3-[2(R)-Hydroxypropyl]amino-3-methyl-N-[2,3,4,5-tetrahydro-1-[[2'-[[[(ethylamino)carbonyl]amino]methyl][1,1'-biphenyl]-4-yl]methyl]-7-trifluoromethyl-2-oxo-1H-benzazepin-3(R)-yl]butanamide;

108. 3-[2(S),3-Dihydroxypropyl]amino-3-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]butanamide;

109. 3-[2(S),3-Dihydroxypropyl]amino-3-methyl-N-[2,3,4,5-tetrahydro-1-[[2'-[[[(ethylamino)carbonyl]amino]methyl][1,1'-biphenyl]-4-yl]methyl]-7-fluoro-2-oxo-1H-benzazepin-3(R)-yl]butanamide;

110. 3-[2(S),3-Dihydroxypropyl]amino-3-methyl-N-[2,3,4,5-tetrahydro-1-[[2'-[[[(ethylamino)carbonyl]amino]methyl][1,1'-biphenyl]-4-yl]methyl]-7-methoxy-2-oxo-1H-benzazepin-3(R)-yl]butanamide;

111. 3-[2(S),3-Dihydroxypropyl]amino-3-methyl-N-[2,3,4,5-tetrahydro-1-[[2'-[[[(ethylamino)carbonyl]amino]methyl][1,1'-biphenyl]-4-yl]methyl]-7-methylthio-2-oxo-1H-benzazepin-3(R)-yl]butanamide;

112. 3-[2(S),3-Dihydroxypropyl]amino-3-methyl-N-[2,3,4,5-tetrahydro-1-[[2'-[[[(ethylamino)carbonyl]amino]methyl][1,1'-biphenyl]-4-yl]methyl]-7-trifluoromethyl-2-oxo-1H-benzazepin-3(R)-yl]butanamide;

113. 2-Amino-2-methyl-N-[2,3,4,5-tetrahydro-1-[[2'-[[[[(hydroxethyl)amino]carbonyl]amino]methyl][1,1'-biphenyl]-4-yl]methyl]-2-oxo-1H-benzazepin-3(R)-yl]propanamide;

114. 2-Amino-2-methyl-N-[2,3,4,5-tetrahydro-1-[[2'-[[[[(hydroxyethyl)amino]carbonyl]amino]methyl][1,1'-biphenyl]-4-yl]methyl]-7-fluoro-2-oxo-1H-benzazepin-3(R)-yl]propanamide;

115. 2-Amino-2-methyl-N-[2,3,4,5-tetrahydro-1-[[2'-[[[[(hydroxyethyl)amino]carbonyl]amino]methyl][1,1'-biphenyl]-4-yl]methyl]-7-methoxy-2-oxo-1H-benzazepin-3(R)-yl]propanamide;

116. 2-Amino-2-methyl-N-[2,3,4,5-tetrahydro-1-[[2'-[[[[(hydroxyethyl)amino]carbonyl]amino]methyl][1,1'-biphenyl]-4-yl]methyl]-7-methylthio-2-oxo-1H-benzazepin-3(R)-yl]propanamide;

117. 2-Amino-2-methyl-N-[2,3,4,5-tetrahydro-1-[[2'-[[[[(hydroxyethyl)amino]carbonyl]amino]methyl][1,1'-biphenyl]-4-yl]methyl]-7-trifluoromethyl-2-oxo-1H-benzazepin-3(R)-yl]propanamide;

118. 3-Amino-3-methyl-N-[2,3,4,5-tetrahydro-1-[[2'-[[[[(hydroxyethyl)amino]carbonyl]amino]methyl][1,1'-biphenyl]-4-yl]methyl]-2-oxo-1H-benzazepin-3(R)-yl]butanamide;

119. 3-Amino-3-methyl-N-[2,3,4,5-tetrahydro-1-[[2'-[[(hydroxyethyl)amino]carbonyl]amino]methyl][1,1'-biphenyl]-4-yl]methyl]-7-fluoro-2-oxo-1H-benzazepin-3(R)-yl]butanamide;

120. 3-Amino-3-methyl-N-[2,3,4,5-tetrahydro-1-[[2'-[[[[(hydroxyethyl)amino]carbonyl]amino]methyl][1,1'-biphenyl]-4-yl]methyl]-7-methoxy-2-oxo-1H-benzazepin-3(R)-yl]butanamide;

121. 3-Amino-3-methyl-N-[2,3,4,5-tetrahydro-1-[[2'-[[[[(hydroxyethyl)amino]carbonyl]amino]methyl][1,1'-biphenyl]-4-yl]methyl]-7-methylthio-2-oxo-1H-benzazepin-3(R)-yl]butanamide;

122. 3-Amino-3-methyl-N-[2,3,4,5-tetrahydro-1-[[2'-[[[[(hydroxyethyl)amino]carbonyl]amino]methyl][1,1'-biphenyl]-4-yl]methyl]-7-trifluoromethyl-2-oxo-1H-benzazepin-3(R)-yl]butanamide;

123. 3-[2(R)-Hydroxypropylamino-3-methyl-N-[2,3,4,5-tetrahydro-1-[[2'-[[[[(hydroxyethyl)amino]carbonyl]amino]methyl][1,1'-biphenyl]-4-yl]methyl]-2-oxo-1H-benzazepin-3(R)-yl]butanamide;

124. 3-[2(R)-Hydroxypropyl]amino-3-methyl-N-[2,3,4,5-tetrahydro-1-[[2'-[[[[(hydroxyethyl)amino]carbonyl]amino]methyl][1,1'-biphenyl]-4-yl]methyl]-7-fluoro-2-oxo-1H-benzazepin-3(R)-yl]butanamide;

125. 3-[2(R)-Hydroxypropyl]amino-3-methyl-N-[2,3,4,5-tetrahydro-1-[[2'-[[[[(hydroxyethyl)amino]carbonyl]amino]methyl][1,1'-biphenyl]-4-yl]methyl]-7-methoxy-2-oxo-1H-benzazepin-3(R)-yl]butanamide;

126. 3-[2(R)-Hydroxypropyl]amino-3-methyl-N-[2,3,4,5-tetrahydro-1-[[2'-[[[[(hydroxyethyl)amino]carbonyl]amino]methyl][1,1'-biphenyl]-4-yl]methyl]-7-methylthio-2-oxo-1H-benzazepin-3(R)-yl]butanamide;

127. 3-[2(R)-Hydroxypropyl]amino-3-methyl-N-[2,3,4,5-tetrahydro-1-[[2'-[[[[(hydroxyethyl)amino]carbonyl]amino]methyl][1,1'-biphenyl]-4-yl]methyl]-7-trifluoromethyl-2-oxo-1H-benzazepin-3(R)-yl]butanamide;

128. 3-[2(S),3-Dihydroxypropyl]amino-3-methyl-N-[2,3,4,5-tetrahydro-1-[[2'-[[[[(hydroxyethyl)amino]carbonyl]amino]methyl]-[1,1'-biphenyl]-4-yl]methyl]-2-oxo-1H-benzazepin-3(R)-yl]butanamide;

129. 3-[2(S),3-Dihydroxypropyl]amino-3-methyl-N-[2,3,4,5-tetrahydro-1-[[2'-[[[[(hydroxyethyl)amino]carbonyl]amino]methyl]-[1,1'-biphenyl]-4-yl]methyl]-7-fluoro-2-oxo-1H-benzazepin-3(R)-yl]butanamide;

130. 3-[2(S),3-Dihydroxypropyl]amino-3-methyl-N-[2,3,4,5-tetrahydro-1-[[2'-[[[[(hydroxyethyl)amino]carbonyl]amino]methyl]-[1,1'-biphenyl]-4-yl]methyl]-7-methoxy-2-oxo-1H-benzazepin-3(R)-yl]butanamide;

131. 3-[2(S),3-Dihydroxypropyl]amino-3-methyl-N-[2,3,4,5-tetrahydro-1-[[2'-[[[[(hydroxyethyl)amino]carbonyl]amino]methyl]-[1,1'-biphenyl]-4-yl]methyl]-7-methylthio-2-oxo-1H-benzazepin-3(R)-yl]butanamide;

132. 3-[2(S),3-Dihydroxypropyl]amino-3-methyl-N-[2,3,4,5-tetrahydro-1-[[2'-[[[[(hydroxyethyl)amino]carbonyl]amino]methyl]-[1,1'-biphenyl]-4-yl]methyl]-7-trifluoromethyl-2-oxo-1H-benzazepin-3(R)-yl]butanamide;

133. N-[5-[[2'-[(Methoxycarbonyl)amino][1,1'-biphenyl]-4-yl]methyl]-2,3,4,5-tetrahydro-4-oxo-1,5-benzothiazepin-3(S)-yl]-3-amino-3-methylbutanamide;

134. N-[5-[[2'-[(Methylaminocarbonyl)amino][1,1'-biphenyl]-4-yl]-methyl]-2,3,4,5-tetrahydro-4-oxo-1,5-benzothiazepin-3(S)-yl]-3-amino-3-methylbutanamide;

135. N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-amino-3-methylbutanamide;

136. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-amino-3-methylbutanamide;

137. N-[5-[[2'-[(Methylaminocarbonyl)amino][1,1'-biphenyl]-4-yl]methyl]-2,3,4,5-tetrahydro-4-oxo-1,5-benzothiazepin-3 (S)-yl]-3-[2(R)-hydroxypropyl]amino-3-methylbutanamide;

138. N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-[2(R)-hydroxypropyl]amino-3-methylbutanamide;

139. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[2(R)-hydroxypropyl]amino-3-methylbutanamide;

140. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[2(S),3-dihydroxypropyl]amino-3-methylbutanamide;

141. 2-Amino-2-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]propanamide;

142. 2-Amino-2-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]propanamide;

143. 2-Amino-2-methyl-N-[2,3,4,5-tetrahydro-5-[[2'-[[[(methylamino)carbonyl]amino]methyl][1,1'-biphenyl]-4-yl]methyl]-8-methoxy-4-oxo-1,5-benzothiazepin-3(S)-yl]propanamide;

144. 2-Amino-2-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]propanamide;

145. 2-Amino-2-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]propanamide;

146. 3-Amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;

147. 3-Amino-3-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]butanamide;

148. 3-Amino-3-methyl-N-[2,3,4,5-tetrahydro-5-[[2'-[[[(methylamino)carbonyl]amino]methyl][1,1'-biphenyl]-4-yl]methyl]-8-methoxy-4-oxo-1,5-benzothiazepin-3 (S)-yl]butanamide;

149. 3-Amino-3-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]butanamide;

150. 3-Amino-3-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]butanamide;

151. 3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;

152. 3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]butanamide;

153. 3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-methoxy-4-oxo-1,5-benzothiazepin-3(S)-yl]butanamide;

154. 3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]butanamide;

155. 3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]butanamide;

156. 3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;

157. 3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]butanamide;

158. 3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]methyl]-8-methoxy4-oxo-1,5-benzothiazepin-3(S)-yl]butanamide;

159. 3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]butanamide;

160. 3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]butanamide;

161. 2-Amino-2-methyl-N-[2,3,4,5-tetrahydro-1-[[2'-[[[(aminocarbonyl)amino]methyl][1,1'-biphenyl]-4-yl]methyl]-4-oxo-1,5-benzothiazepin-3(S)-yl]propanamide;

162. 2-Amino-2-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]propanamide;

163. 2-Amino-2-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]propanamide;

164. 2-Amino-2-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]propanamide;

165. 2-Amino-2-methyl-N-[2,3,4,5-tetrahydro-1-[[2'-[[(aminocarbonyl)amino]methyl][1,1'-biphenyl]-4-yl]methyl)-8-trifluoromethyl-4-oxo-1,5-benzothiazepin-3(S)-yl]propanamide;

166. 3-Amino-3-methyl-N-[2,3,4,5-tetrahydro-5-[[2'-[[(aminocarbonyl)amino]methyl][1,1'-biphenyl]-4-yl]methyl]4-oxo-1,5-benzothiazepin-3(S)-yl]butanamide;

167. 3-Amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;

168. 3-Amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]butanamide;

169. 3-Amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;

170. 3-Amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]butanamide;

171. 3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-4-oxo-1,5-benzothiazepin-3(S)-yl]butanamide;

172. 3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;

173. 3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3 (S)-yl]butanamide;

174. 3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;

175. 3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]butanamide;

176. 3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-4-oxo-1,5-benzothiazepin-3(S)-yl]butanamide;

177. 3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;

178. 3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]butanamide;

179. 3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;

180. 3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]butanamide;

181. 2-Amino-2-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]propanamide;

182. 2-Amino-2-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]propanamide;

183. 2-Amino-2-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]propanamide;

184. 2-Amino-2-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]propanamide;

185. 2-Amino-2-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzothiazepin-3(S)-yl]propanamide;

186. 3-Amino-3-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]butanamide;

187. 3-Amino-3-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]butanamide;

188. 3-Amino-3-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]butanamide;

189. 3-Amino-3-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]butanamide;

190. 3-Amino-3-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzothiazepin-3(S)-yl]butanamide;

191. 3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]butanamide;

192. 3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]butanamide;

193. 3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]butanamide;

194. 3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]butanamide;

195. 3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzothiazepin-3(S)-yl]butanamide;

196. 3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]butanamide;

197. 3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]butanamide;

198. 3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]butanamide;

199. 3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]butanamide;

200. 3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzothiazepin-3(S)-yl]butanamide;

201. 2-Amino-2-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]propanamide;

202. 2-Amino-2-methyl-N-[2,3,4,5-tetrahydro-5-[[2'-[[[[(hydroxyethyl)amino]carbonyl]amino]methyl][1,1'-biphenyl]-4-yl]methyl]-8-fluoro-4-oxo-1,5-benzothiazepin-3(S)-yl]propanamide;

203. 2-Amino-2-methyl-N-[2,3,4,5-tetrahydro-5-[[2'-[[[[(hydroxyethyl)amino]carbonyl]amino]methyl][1,1'-biphenyl]-4-yl]methyl]-8-methoxy-4-oxo-1,5-benzothiazepin-3(S)-yl]propanamide;

204. 2-Amino-2-methyl-N-[2,3,4,5-tetrahydro-5-[[2'-[[[[(hydroxyethyl)amino]carbonyl]amino]methyl][1,1'-biphenyl]-4-yl]methyl]-8-methylthio-4-oxo-1,5-benzothiazepin-3(S)-yl]propanamide;

205. 2-Amino-2-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]propanamide;

206. 3-Amino-3-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]butanamide;

207. 3-Amino-3-methyl-N-[2,3,4,5-tetrahydro-5-[[2'-[[[[(hydroxyethyl)amino]carbonyl]amino]methyl]1,1'-biphenyl]-4-yl]methyl]-8-fluoro-4-oxo-1,5-benzothiazepin-3(S)-yl]butanamide;

208. 3-Amino-3-methyl-N-[2,3,4,5-tetrahydro-5-[[2'-[[[[(hydroxyethyl)amino]carbonyl]amino]methyl][1,1'-biphenyl]-4-yl]methyl]-8-methoxy-4-oxo-1,5-benzothiazepin-3(S)-yl]butanamide;

209. 3-Amino-3-methyl-N-[2,3,4,5-tetrahydro-5-[[2'-[[[[(hydroxyethyl)amino]carbonyl]amino]methyl][1,1'-biphenyl]4-yl]methyl]-8-methylthio-4-oxo-1,5-benzothiazepin-3(S)-yl]butanamide;

210. 3-Amino-3-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]butanamide;

211. 3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]butanamide;

212. 3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-fluoro-4-oxo-1,5-benzothiazepin-3 (S)-yl]butanamide;

213. 3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-methoxy-4-oxo-1,5-benzothiazepin-3(S)-yl]butanamide;

214. 3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-methylthio-4-oxo-1,5-benzothiazepin-3(S)-yl]butanamide;

215. 3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]butanamide;

216. 3-[2(S),3-Dihydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]butanamide;

217. 3-[2(S),3-Dihydroxypropyl]amino-3-methyl-N-[2,3,4,5-tetrahydro-5-[[2'-[[[[(hydroxyethyl)amino]carbonyl]amino]methyl][1,1'-biphenyl]-4-yl]methyl]-8-fluoro-4-oxo-1,5-benzo-thiazepin-3(S)-yl]butanamide;

218. 3-[2(S),3-Dihydroxypropyl]amino-3-methyl-N-[2,3,4,5-tetrahydro-5-[[2'-[[[[(hydroxyethyl)amino]carbonyl]amino]methyl]-[1,1'-biphenyl]-4-yl]methyl]-8-methoxy-4-oxo-1,5-benzothiazepin-3(S)-yl]butanamide;

219. 3-[2(S),3-Dihydroxypropyl]amino-3-methyl-N-[2,3,4,5-tetrahydro-5-[[2'-[[[[(hydroxyethyl)amino]carbonyl]amino]methyl]-[1,1'-biphenyl]-4-yl]methyl]-8-methylthio-4-oxo-1,5-benzothiazepin-3(S)-yl]butanamide;

220. 3-[2(S),3-Dihydroxypropyl]amino-3-methyl-N-[2,3,4,5-tetrahydro-5-[[2'-[[[[(hydroxyethyl)amino]carbonyl]amino]methyl]-[1,1'-biphenyl]-4-yl]methyl]-8-trifluoromethyl-4-oxo-1,5-benzothiazepin-3(S)-yl]butanamide;

221. 2-Amino-2-methyl-N-[2,3,4,5-tetrahydro-1-[[2'-[2-[[(methylamino)carbonyl]amino]prop-2-yl][1,1'-biphenyl]-4-yl]methyl]-2-oxo-1H-benzazepin-3(R)-yl]propanamide;

222. 2-Amino-2-methyl-N-[2,3,4,5-tetrahydro-1-[[2'-[1-[[(methylamino)carbonyl]amino]ethyl][1,1'-biphenyl]-4-yl]methyl]-2-oxo-1H-benzazepin-3(R)-yl]propanarnide;

223. 2-Amino-2-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]propanamide;

224. 3-Amino-3-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]butanamide;

225. 3-[2(R)-Hydroxypropyl]amino-3-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]butanamide;

226. 3-[2(S),3-Dihydroxypropyl]amino-3-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]butanamide;

227. 2-Amino-2-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]propanamide;

228. 3-Amino-3-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]butanamide;

229. 3-[2(R)-Hydroxypropyl]amino-3-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]butanamide;

230. 3-[2(S),3-Dihydroxypropyl]amino-3-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]butanamide;

231. 2-Amino-2-methyl-N-[2,3,4,5-tetrahydro-1-[[2'-[[[(methylamino)carbonyl]oxy]methyl][1,1'-biphenyl]-4-yl]methyl]-2-oxo-1H-benzazepin-3(R)-yl]propanamide;

232. 3-Amino-3-methyl-N-[2,3,4,5-tetrahydro-1-[[2'-[[[(methylamino)carbonyl]oxy]methyl][1,1'-biphenyl]-4-yl]methyl]-2-oxo-1H-benzazepin-3(R)-yl]butanamide;

233. 3-[2(R)-Hydroxypropyl]amino-3-methyl-N-[2,3,4,5-tetrahydro-1-[[2'-[[[(methylamino)carbonyl]oxy]methyl][1,1'-biphenyl]-4-yl]methyl]-2-oxo-1H-benzazepin-3(R)-yl]butanamide;

234. 3-[2(S),3-Dihydroxypropyl]amino-3-methyl-N-[2,3,4,5-tetrahydro-1-[[2'-[[[(methylamino)carbonyl]oxy]methyl][1,1'-biphenyl]-4-yl]methyl]-2-oxo-1H-benzazepin-3(R)-yl]butanamide;

235. 2-Amino-2-methyl-N-[2,3,4,5-tetrahydro-5-[[2'-[[[(methylamino)carbonyl]oxy]methyl][1,1'-biphenyl]-4-yl]methyl]-4-oxo-1,5-benzothiazepin-3(S)-yl]propanamide;

236. 3-Amino-3-methyl-N-[2,3,4,5-tetrahydro-5-[[2'-[[[(methylamino)carbonyl]oxy]methyl][1,1'-biphenyl]-4-yl]methyl]-4-oxo-1,5-benzothiazepin-3(S)-yl]butanamide;

237. 3-[2(R)-Hydroxypropyl]amino-3-methyl-N-[2,3,4,5-tetrahydro-5-[[2'-[[[(methylamino)carbonyl]oxy]methyl][1,1'-biphenyl]-4-yl]methyl]-4-oxo-1,5-benzothiazepin-3(S)-yl]butanamide;

238. 3-[2(S),3-Dihydroxypropyl]amino-3-methyl-N-[2,3,4,5-tetrahydro-5-[[2'-[[[(methylamino)carbonyl]oxy]methyl][1,1'-biphenyl]-4-yl]methyl]-4-oxo-1,5-benzothiazepin-3(S)-yl]butanamide.

Representative examples of the nomenclature employed are given below:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide

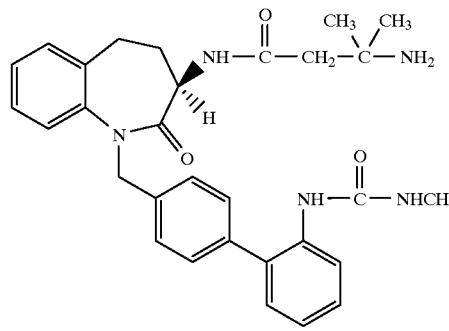

N-[1-[[2'-[(Methylaminocarbonyl)oxy][1,1'-biphenyl]-4-yl]methyl]-7-methyl-2,3,4,5-tetrahydro-2-oxo-1H-1-benzazepin-3(R)-yl]-2-amino-2-methylpropanamide

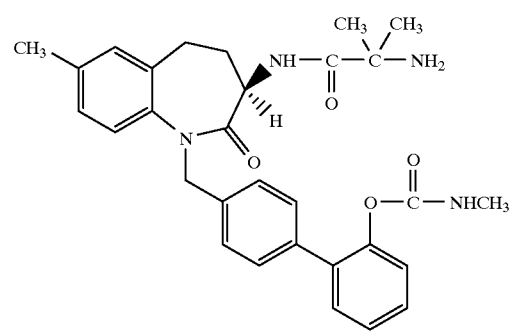

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide

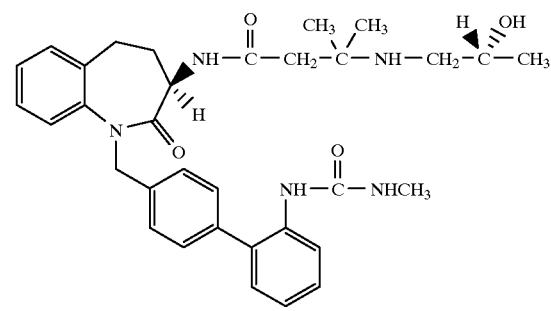

3-[2(S),3-Dihydroxypropyl]amino-3-methyl-N-[2,3,4,5-tetrahydro-5-[[2'-[2-[[4-morpholinocarbonyl]amino]ethyl][1,1'-biphenyl]-4-yl]methyl]-7-methyl-4-oxo-1,5-benzothiazepin-3(S)-yl]butanamide

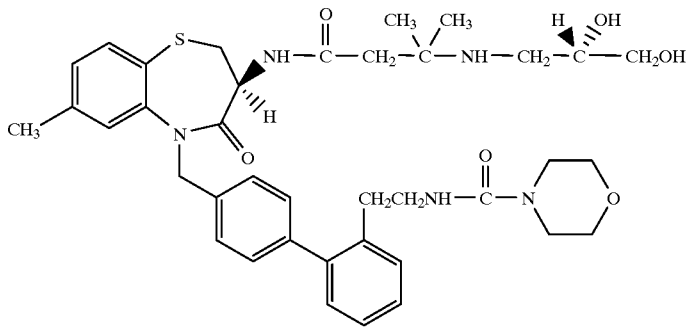

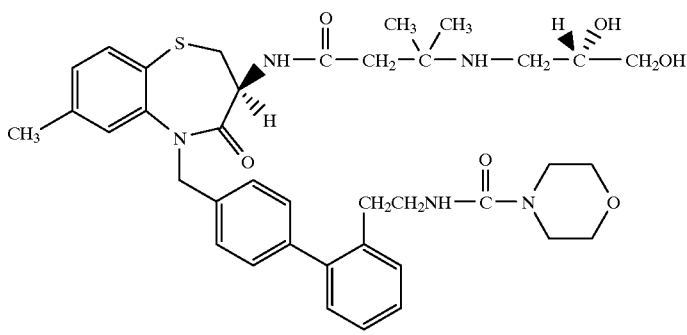

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when n=0, the asymmetric center is designated as the R-isomer. When n=1, this center will be designated according to the R/S rules as either R or S depending upon the value of X.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described in the following reaction Schemes.

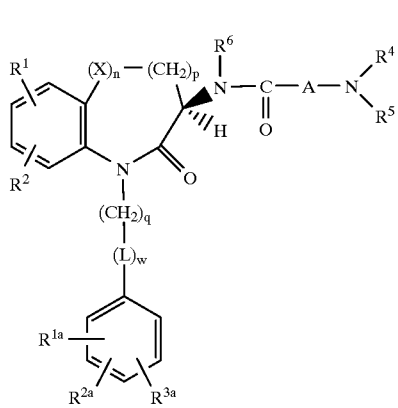

Ia

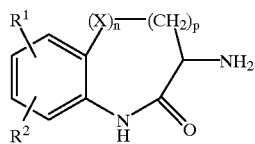

II

Benzo-fused lactams 3 wherein the lactam is a seven-membered ring are conveniently prepared from substituted tetralones 2 using known procedures. The substituted tetralones are, in some cases, commercially available or are prepared from a suitably substituted derivative of 4-phenylbutyric acid 1. Cyclization of 1 can be achieved by a number of methods well known in the literature including treatment with polyphosphoric acid at elevated temperatures as shown in Scheme 1.

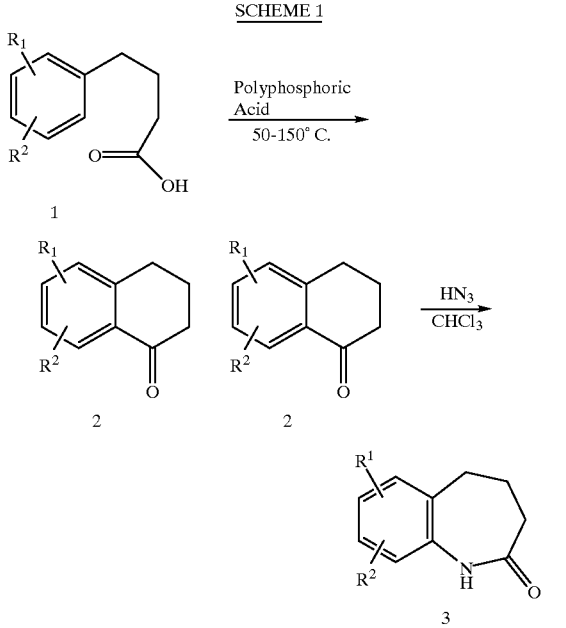

Conversion of substituted tetralones 2 to benzolactams 3 can be achieved by a number of methods familiar to those skilled in the art. A suitable method involves the use of hydrazoic acid (Schmidt or Curtius reactions) to form the substituted benzolactam 3.

Benzo-fused lactams wherein the lactam is an eight-membered ring (6) are prepared as described by D. H. Jones, et al, *J. Chem. Soc.* C, 2176–2181 (1969) by a series of analogous transformations starting from a substituted derivative of 5-phenylpentanoic acid 4 as shown in Scheme 2.

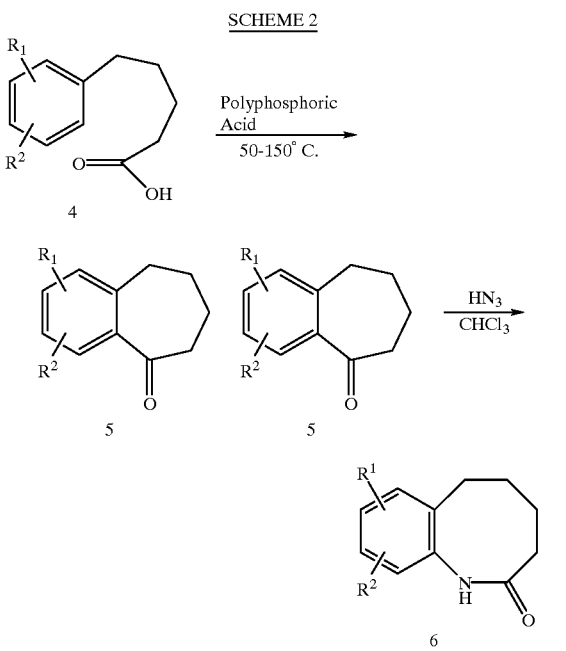

As illustrated in Scheme 3, an analogous sequence is employed in the construction of benzo-fused lactams containing nine-membered rings. The requisite benzocyclo octanone intermediate 8 is obtained by acid-catalyzed cyclization of the substituted 6-phenylhexanoic acid precursor 7 using the aforementioned conditions. Elaboration to the desired nine-membered lactam product 9 can be achieved directly, through the use of hydrazoic acid (Schmidt reaction) using conditions described by R. Huisgen, et al, *Ann.*, 586, 30–51 (1954); or, via Beckmann rearrangement of an intermediate oxime, as demonstrated by W. M. Schubert, et al, *J. Amer. Chem. Soc.*, 76, 5462–5465 (1954).

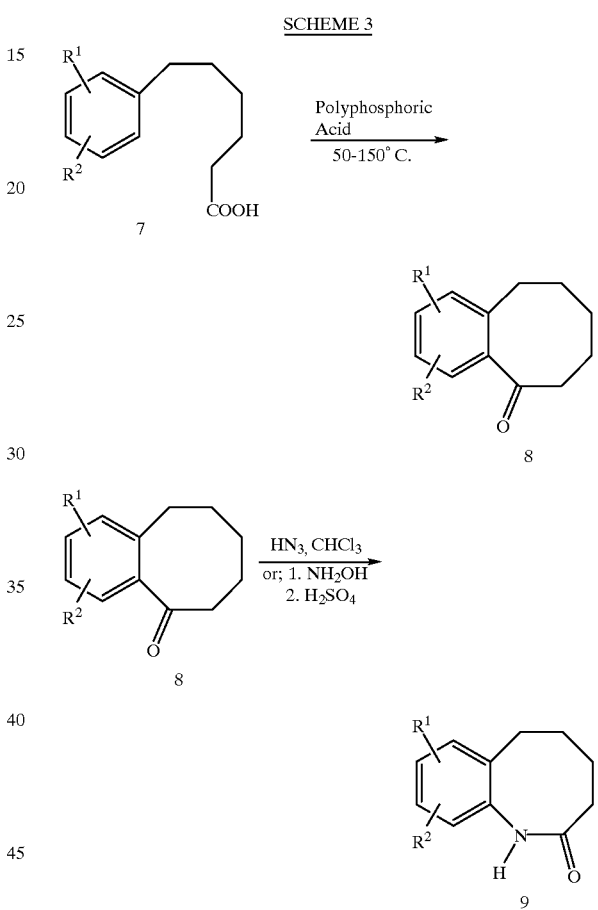

As shown in Scheme 4, 3-aminobenzolactam analogs wherein the lactam is a six-membered ring (14) are prepared from a substituted derivative of 2-nitrobenzyl chloride (or bromide) 10 by the method of A. L. Davis, et al, *Arch. Biochem. Biophys.*, 102, 48–51 (1963) and references cited therein.

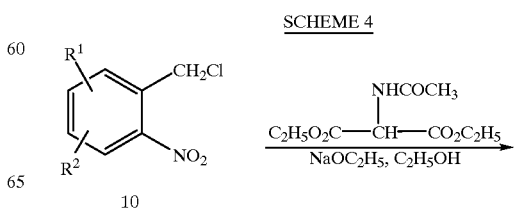

-continued

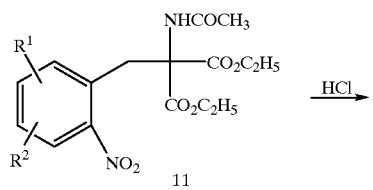
11

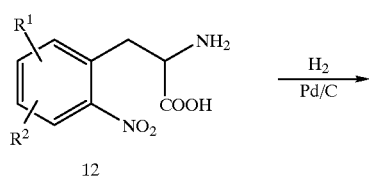
12

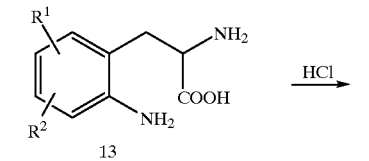
13

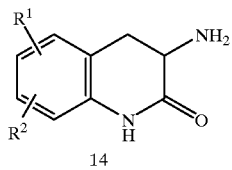
14

Benzo-fused aminolactam analogs containing a five-membered lactam are prepared by an analogous sequence from appropriately substituted derivatives of ethyl o-nitromandelate 15 by the procedure of A. L. Davis, et al, *J. Med. Chem.*, 16, 1043–1045 (1973), as shown in Scheme 5.

-continued

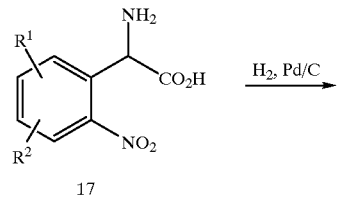
17

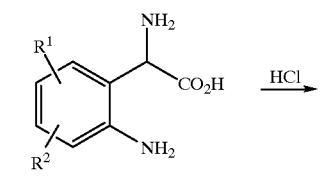
18

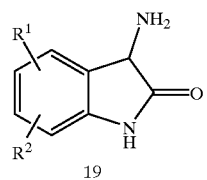
19

Conversion of substituted benzo-fused lactams to the requisite 3-amino derivatives can be achieved by a number of methods familiar to those skilled in the art, including those described by Watthey, et al, *J. Med. Chem.*, 28, 1511–1516 (1985) and references cited therein. One common route proceeds via the intermediacy of a 3-halo (chloro, bromo or iodo) intermediate which is subsequently displaced by a nitrogen nucleophile, typically azide. A useful method of forming the 3-iodobenzolactam intermediate 20 involves treating the benzolactam with two equivalents each of iodotrimethylsilane and iodine at low temperature, as illustrated in Scheme 6 for the seven-membered ring analog 3.

SCHEME 5

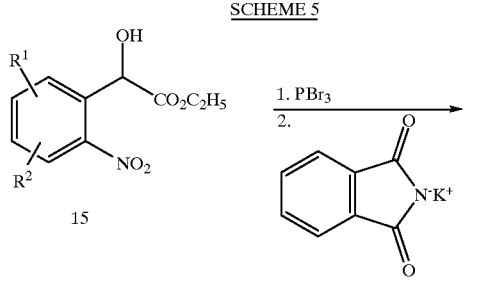

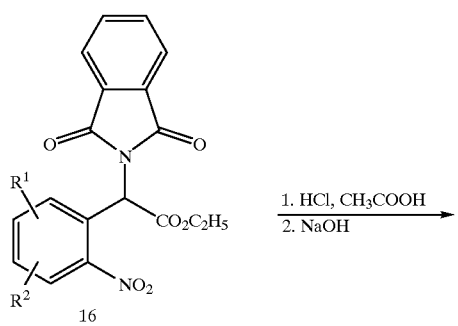
16

SCHEME 6

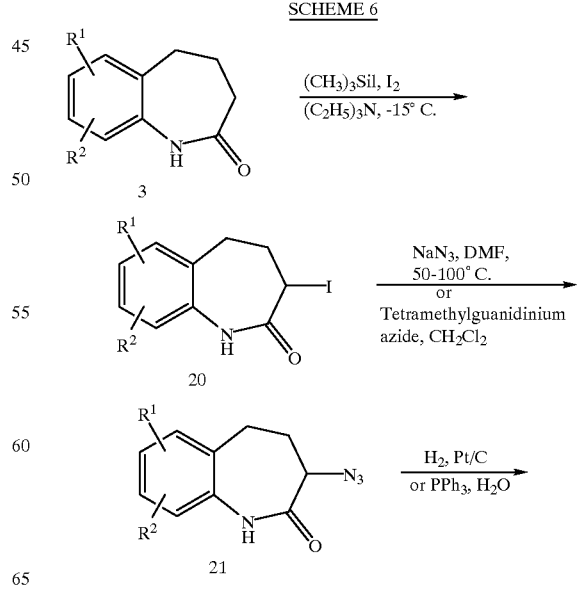

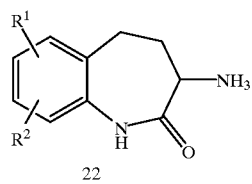

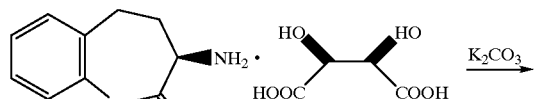

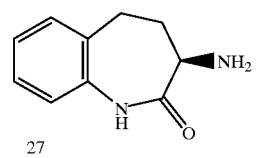

Elaboration of the iodobenzolactams to the desired aminolactam intermediate II is achieved by a two-step procedure illustrated in Scheme 6. Typically, iodobenzolactam 20 is treated with sodium azide in N,N-dimethylformamide at 50–1001° C. to give the 3-azido derivative 21. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative 22. Formation of the analogous derivatives of the eight- and nine-membered benzolactams is also achieved by the routes shown in Scheme 6.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

A useful preparation of the chiral intermediate 27 is shown in Scheme 7.

Conversion of 1-tetralone to the seven-membered benzolactam 24 is achieved by Beckman rearrangement of the intermediate oxime 23. Treatment of 24 with iodine and hexamethyldisilazane gives the 3-iodo derivative 25 which is sequentially treated with ammonia and D-tartaric acid to give the diastereomeric D-tartrate salt 26 after recrystallization. Liberation of the free amine 27 is achieved by neutralization of the D-tartrate salt with potassium carbonate followed by extractive isolation.

Intermediates of Formula II wherein X is a sulfur atom are prepared by methods described in the literature and known to those skilled in the art. As illustrated in Scheme 8, the seven-membered ring analog 35 is prepared from a protected derivative of cysteine 29 by the method of Slade, et al, *J. Med. Chem.*, 28, 1517–1521 (1985) and references cited therein (CBz is benzyloxycarbonyl).

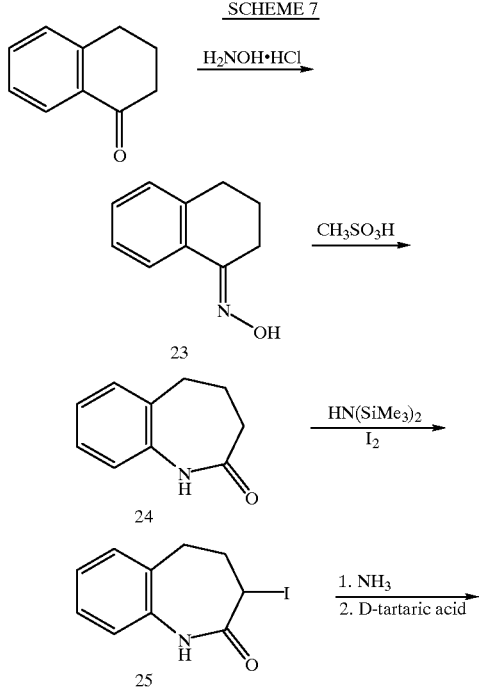

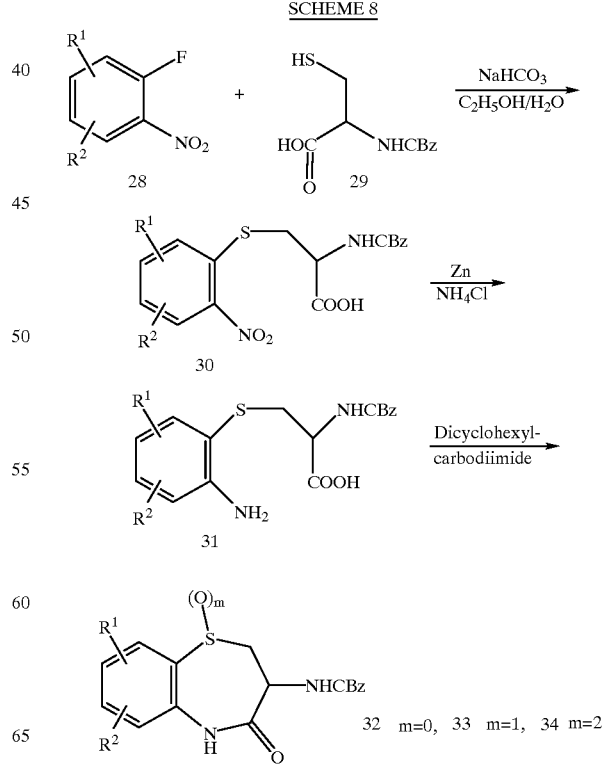

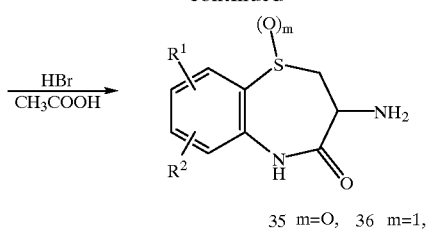

35 m=0, 36 m=1, 37 m=2

Sulfoxide and sulfone intermediates 36 and 37 are prepared by oxidation of 32 with various oxidants such as sodium periodate or meta-chloroperbenzoic acid. Eight-membered ring intermediates of Formula II wherein X is sulfur can be prepared by an analogous route starting from derivatives of homo-cysteine.

Intermediates of Formula II wherein X is an oxygen atom are prepared by methods described in the literature and known to those skilled in the art. For example, the seven-membered ring analog 39 can be prepared from a substituted derivative of 3-(2-nitrophenoxy)-propanoic acid 38 by the method of J. Ott, *Arch. Pharm.* (Weinheim, Ger.), 323(9), 601–603 (1990).

SCHEME 9

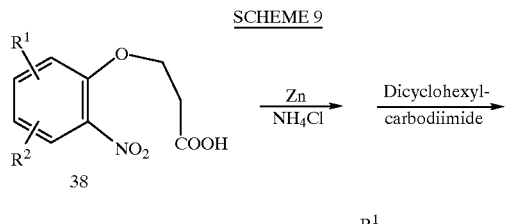

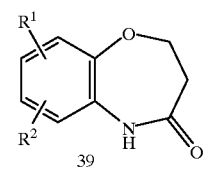

39

Six-membered ring analogs wherein X is oxygen (41) may be prepared by reaction of a substituted derivative of 2-aminophenol 40 with chloroacetyl chloride by the method of Huang and Chan, *Synthesis*, 10, 851 (1984) and references cited therein. Subsequent incorporation of an amino group at the 3 position of either 39 or 41 is achieved by the methods described in Scheme 6.

SCHEME 10

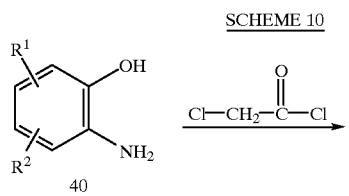

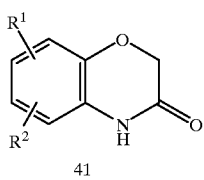

41

Seven-membered ring analogs of Formula II wherein X is C=O can be prepared from derivatives of tryptophan as described in the *Australian J. Chem.*, 22, 633–640 (1980). Seven-membered ring analogs of Formula II wherein X is CH=CH can be prepared from the aforementioned analogs wherein X is C=O. Treatment of 42 with chemical reducing agents such as sodium borohydride in a polar solvent such as methanol or ethanol results in reduction to give the secondary alcohol derivative 43 (X=CHOH).

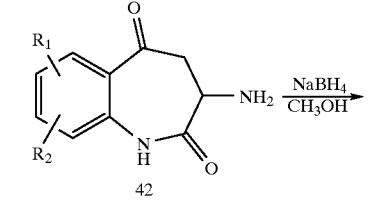

42

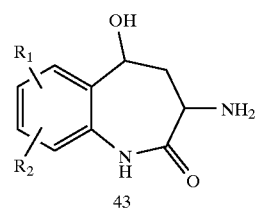

43

Dehydration of 43 can be achieved by several methods described in the literature and familiar to those skilled in the art. For example, treatment of 43 in an inert solvent, such as benzene, with a strong acid such as p-toluenesulfonic acid, can result in dehydration to the unsaturated analog 44.

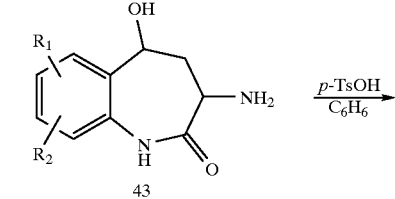

43

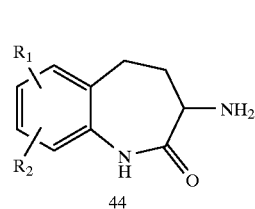

44

Intermediates of formula II can be further elaborated to new intermediates (formula III) which are substituted on the amino group (Scheme 11). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 11

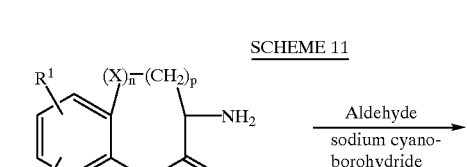

II

-continued

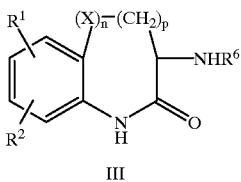

III

Attachment of the amino acid sidechain to intermediates of formula III is accomplished by the route shown in Scheme 12. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") or benzotriazol-1-yloxytripyrrolidinophosphonium hexafluorophosphate ("PyBOP") in an inert solvent such as methylene chloride. Separation of unwanted side products, and purification of intermediates is achieved by chromatography on silica gel, employing flash chromatography (W. C. Still, M. Kahn and A. Mitra, *J. Org. Chem.*, 43, 2923 (1978)) or by medium pressure liquid chromatography.

SCHEME 12

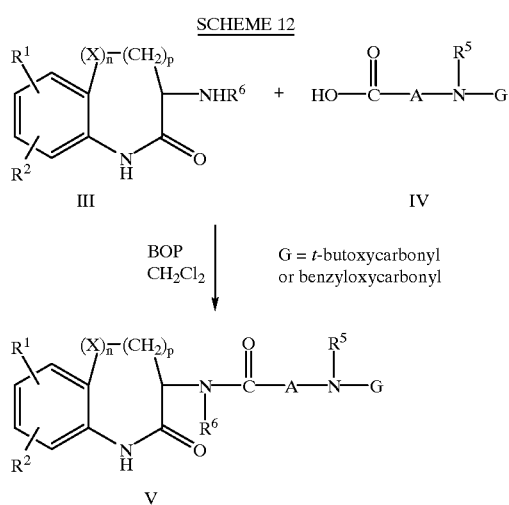

The protected amino acid derivatives IV are, in many cases, commercially available in t-butoxycarbonyl (BOC) or benzyloxycarbonyl (CBz) forms. A useful method to prepare the preferred sidechain 49 is shown in Scheme 13.

SCHEME 13

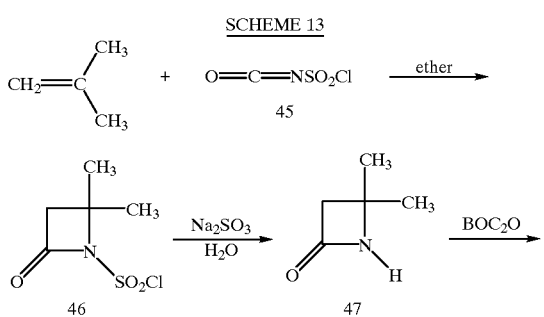

-continued

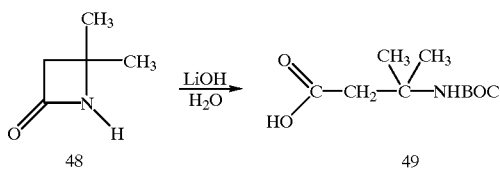

Reaction of isobutylene with N-chlorosulfonylisocyanate 45 in diethyl ether gives the azetidinone derivative 46. Removal of the chlorosulfonyl group with aqueous sodium sulfite followed by reaction with di-t-butyldicarbonate gives the BOC-protected intermediate 48. Alkaline hydrolysis gives the protected amino acid derivative 49 in good overall yield.

Intermediates of formula VII are prepared as shown in Scheme 14 by treatment of the desired lactam intermediate V with an alkylating agent VI, wherein Y is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20–100° C. Substituents on the alkylating agent VI may need to be protected during alkylation. A description of such protecting groups may be found in: *Protective Groups in Organic Synthesis*, T. W. Greene, John Wiley and Sons, New York, 1981.

SCHEME 14

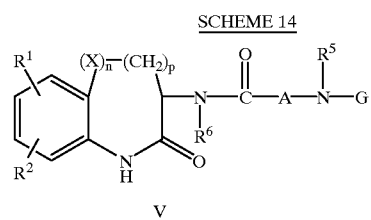

V

1. NaH/DMF
2. 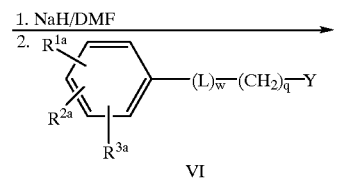

VI

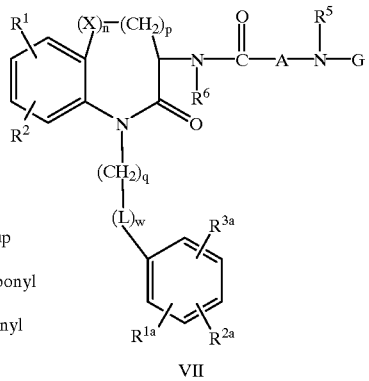

Y is a leaving group

G is a t-butoxycarbonyl or benzyloxycarbonyl

VII

Alkylating agents VI are in some cases commercially available or may be prepared by methods described in the literature and familiar to one skilled in the art. Compounds of formula I where $R^{3a}$ or $R^{3b}$ is a carbamate, semicarbazide or urea derivative, wherein this functionality is attached to the phenyl ring by a nitrogen atom are prepared from intermediate 50, obtained by alkylation with a derivative of formula VI wherein $R^{3a}$ or $R^{3b}$ is a nitro group as shown in Scheme 15.

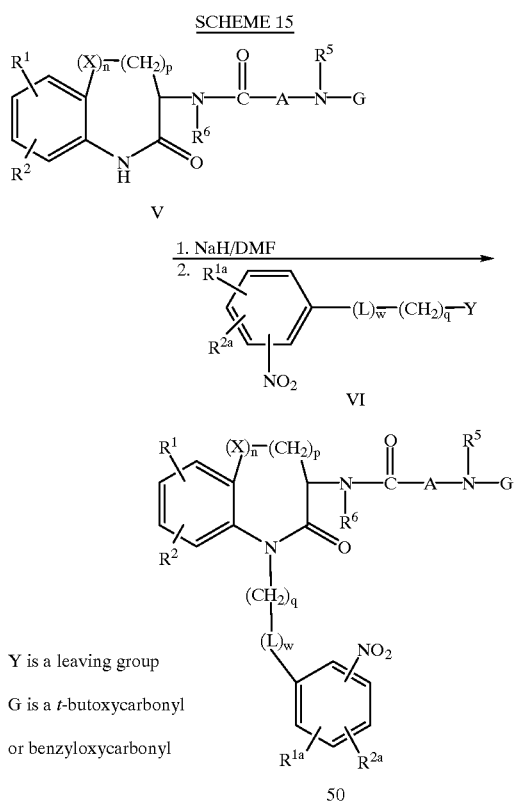

Y is a leaving group
G is a *t*-butoxycarbonyl or benzyloxycarbonyl

A useful method of synthesizing a preferred alkylating agent 54 is shown in reaction Scheme 16.

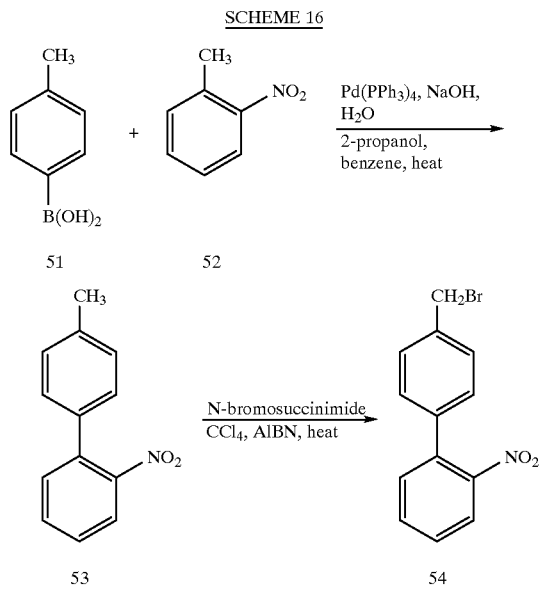

Reaction of 4-tolylboronic acid 51 with 2-bromonitrobenzene 52 in the presence of a transition metal catalyst such as (tetrakis)triphenylphosphine palladium (0) in a mixed solvent system containing aqueous sodium hydroxide, water, 2-propanol and benzene at elevated temperatures for several hours gives the coupled product 53 in good overall yield. Chromatographic purification and separation of unwanted by-products is conveniently performed on silica, eluting with common organic solvents such as hexane, ethyl acetate and methylene chloride. Conversion of 53 to the bromide derivative 54 is accomplished by treatment with N-bromosuccinimide in refluxing carbon tetrachloride in the presence of a radical initiator such as benzoyl peroxide or 2,2'-azobisisobutyronitrile (AIBN).

As shown in Scheme 17, reduction of the nitro group of 50 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 50 must be compatible with the experimental conditions anticipated for reduction. For example, intermediate 50 wherein G is t-butoxycarbonyl (BOC) is stable to the conditions of catalytic reduction employed in the conversion to 55. Intermediate 55 may also be further elaborated to a new intermediate 56 by reductive alkylation with an aldehyde by the aforementioned procedures.

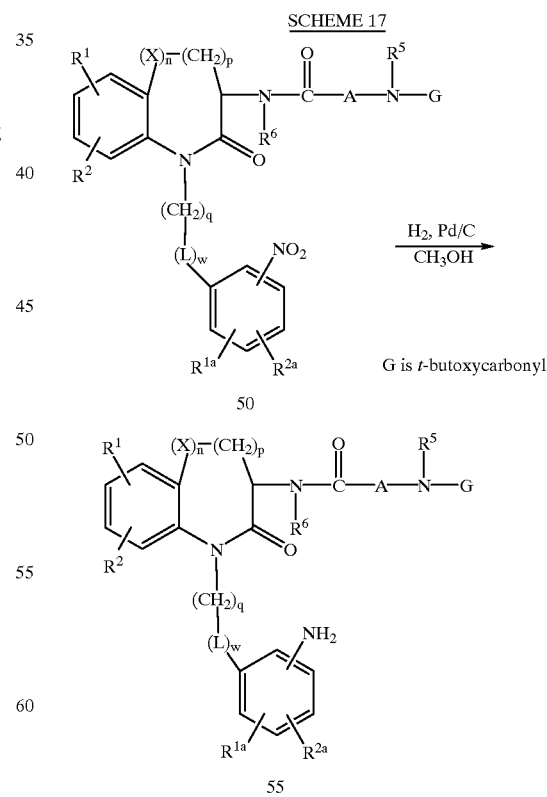

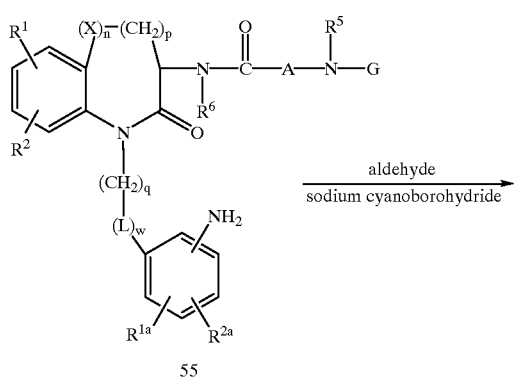

55

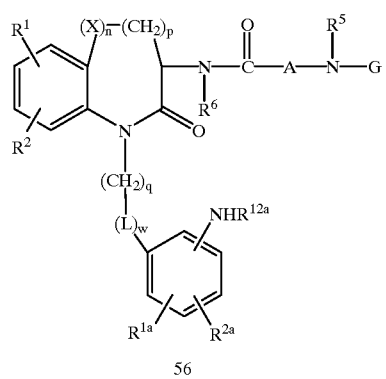

56

Elaboration of 56 to carbamate compound 57 is achieved by reaction with the appropriate chloroformate reagent in pyridine or in methylene chloride with triethylamine as shown in Scheme 18.

SCHEME 18

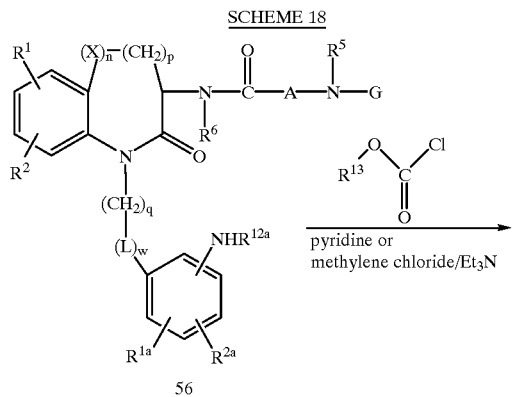

56

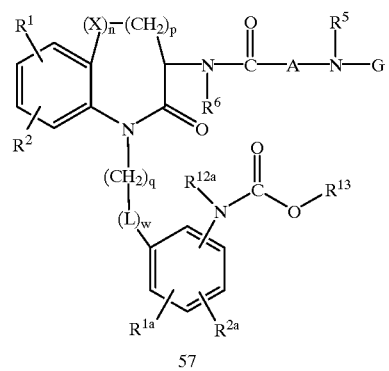

57

Transformation of amine intermediate 56 to urea derivatives is accomplished in several ways. Terminally disubstituted compounds can be obtained directly by reaction of 56 with a disubstituted carbamoyl chloride 58 in an inert solvent such as methylene chloride in the presence of triethylamine or 4-dimethylaminopyridine. In addition, mono-substituted compound 61 wherein either $R^{4b}$ or $R^{12b}$ is hydrogen is obtained from 56 by reaction with an isocyanate 60 as shown in Scheme 19. Terminally unsubstituted urea 61, wherein $R^{12b}$ is hydrogen, is also prepared from amine 56 by reaction with trimethylsilyl isocyanate (60; $R^{12b}$ is $(CH_3)_3Si$).

SCHEME 19

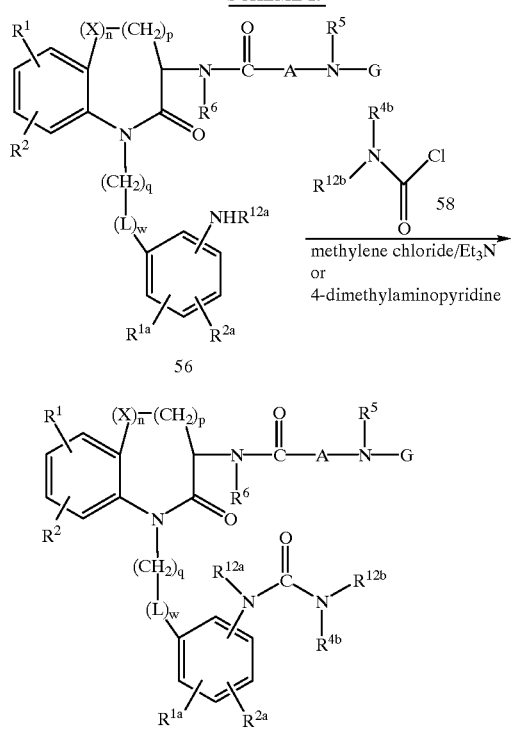

59

39

-continued

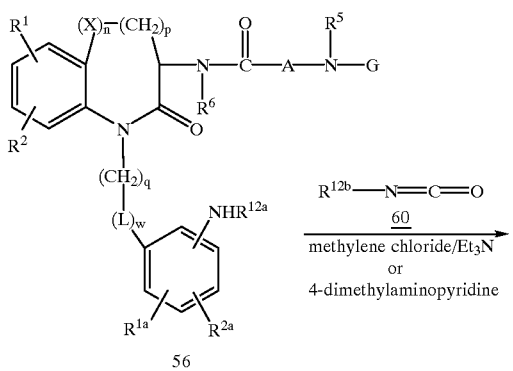

56

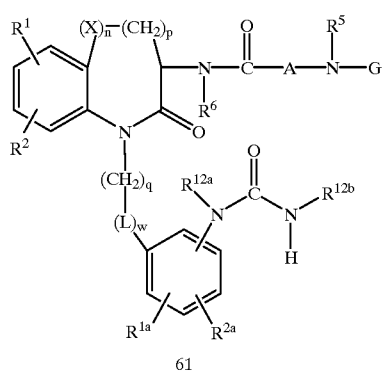

61

Alternatively, amine 55 is converted to an isocyanate 62 by treatment with phosgene or an equivalent reagent such as bis(trichloromethyl)carbonate (triphosgene) as indicated in Scheme 20. Subsequent reaction of 62 with primary or secondary amines in an inert solvent such as methylene chloride gives the corresponding urea derivative 59 in good yield. Isocyanate 62 is also converted to substituted semi-carbazides 63 or hydroxy- or alkoxyureas 64 by reaction with substituted hydrazines or hydroxy- or alkoxylamines, respectively.

SCHEME 20

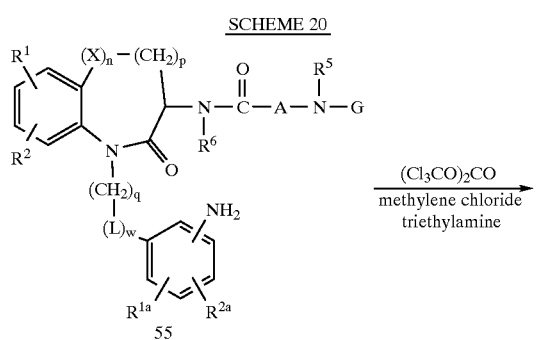

55

G is t-butoxycarbonyl
or
benzyloxycarbonyl

40

-continued

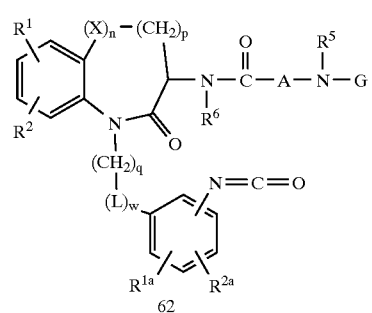

62

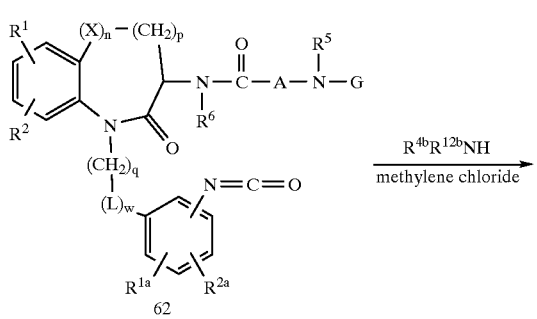

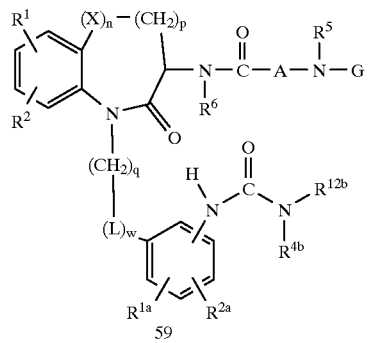

59

G is t-butoxycarbonyl
or
benzyloxycarbonyl

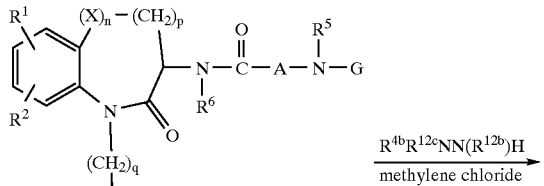

62

41
-continued

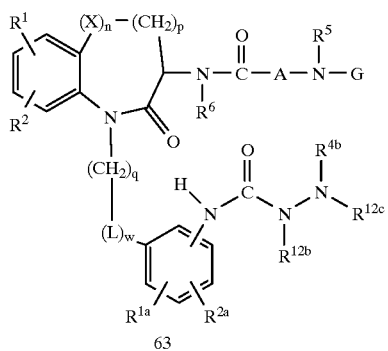
63

G is t-butoxycarbonyl
or
benzyloxycarbonyl

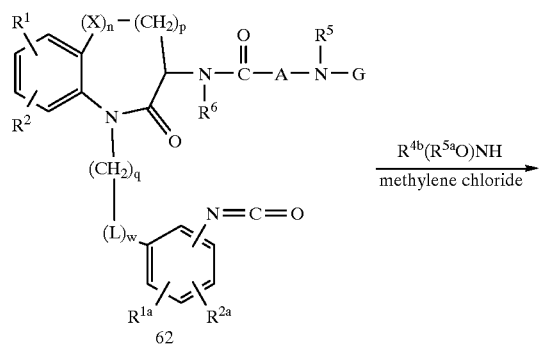
62

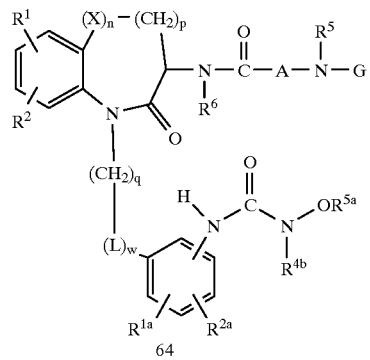
64

G is t-butoxycarbonyl
or
benzyloxycarbonyl

Compounds of formula I where $R^{3a}$ or $R^{3b}$ is a carbazate or carbamate derivative where attachment to the phenyl ring is through the oxygen atom of the carbazate or carbamate linkage are prepared from acetophenone intermediate 65 as indicated in Scheme 21.

42

SCHEME 21

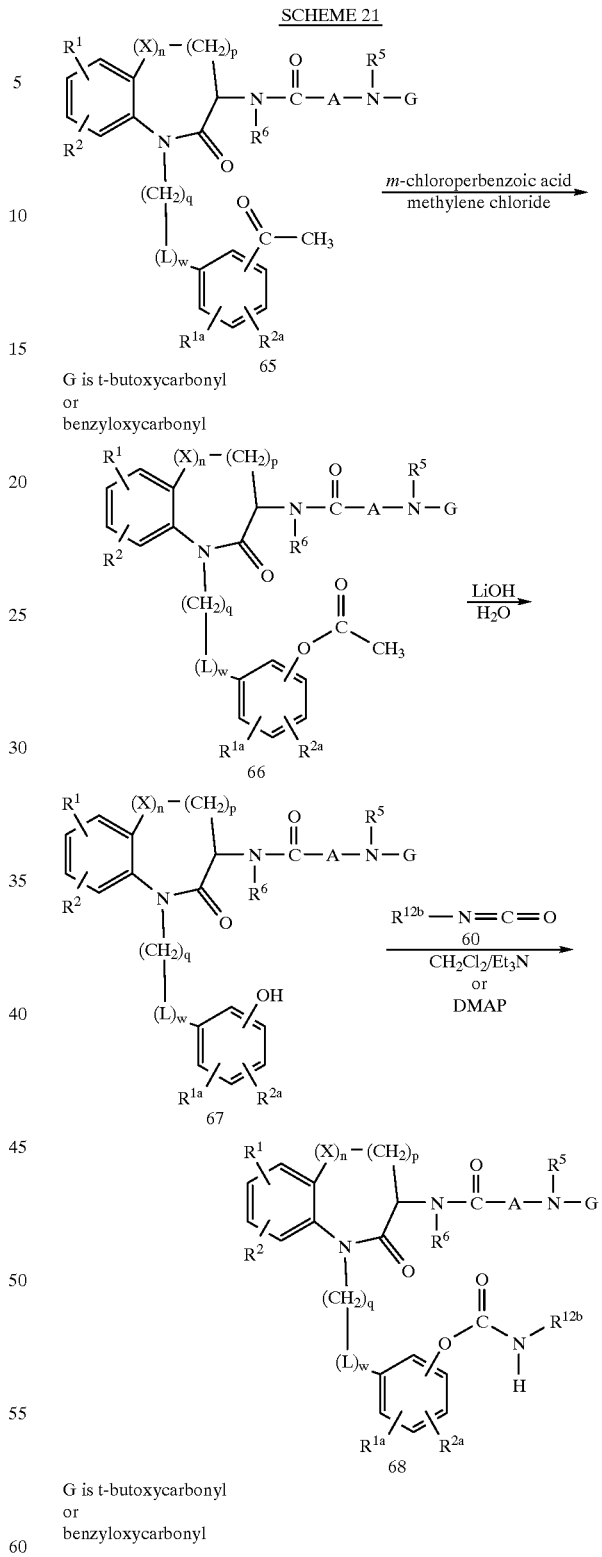

G is t-butoxycarbonyl
or
benzyloxycarbonyl

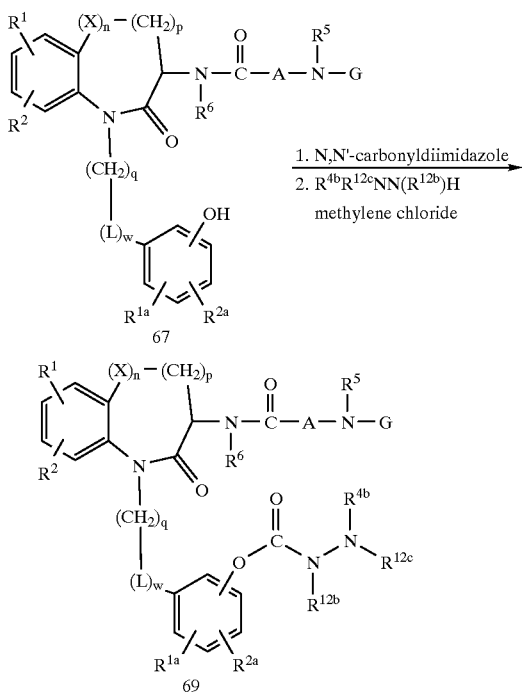

G is t-butoxycarbonyl
or
benzyloxycarbonyl

Oxidative rearrangement of 65 through the use of a peroxy-carboxylic acid (Baeyer-Villager reaction) such as m-chloroperbenzoic acid gives the ester 66 which is hydrolyzed in the presence of a strong base such as sodium or lithium hydroxide to give phenol 67. Reaction of 67 with an isocyanate leads directly to carbamate 68. Additionally, treatment of 67 with N,N'-carbonyldiimidazole in dimethylformamide can form an activated intermediate which will react with substituted hydrazine reagents to give a carbazate product 69.

Compounds of formula I wherein $R^{3a}$ or $R^{3b}$ is $R^{4b}R^{12b}NCON(R^{12a})CH_2$—, $R^{4b}R^{12b}NCSN(R^{12a})CH_2$—, $R^{4b}R^{12c}NN(R^{12b})CSN(R^{12a})CH_2$—, $R^{4b}R^{12c}NN(R^{12b})CON(R^{12a})CH_2$— or $R^{13}OCON(R^{12a})CH_2$— can be prepared from the t-butyl ester intermediate 70 as described in Scheme 22. Removal of the t-butyl ester through the use of trifluoroacetic acid will give the carboxylic acid 71. It may be appreciated by one skilled in the art that the protecting group G in 70 must therefore be compatible with the strongly acidic conditions employed for ester cleavage; hence G is taken as benzyloxycarbonyl. Conversion of the carboxylic acid to the benzylamine derivative 72 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 72 can be further elaborated to 73 by the aforementioned reductive amination procedure.

SCHEME 22

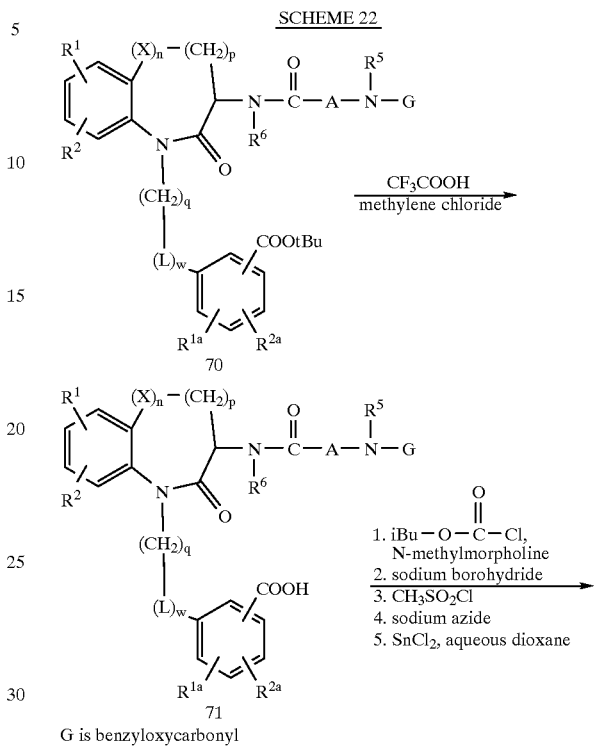

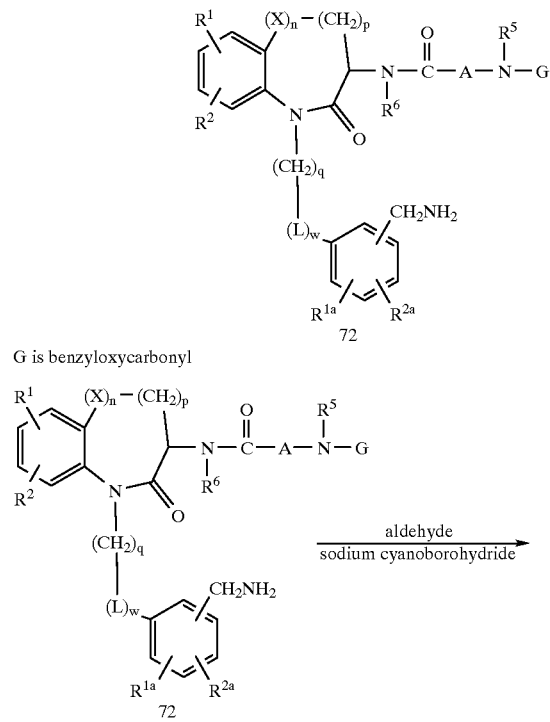

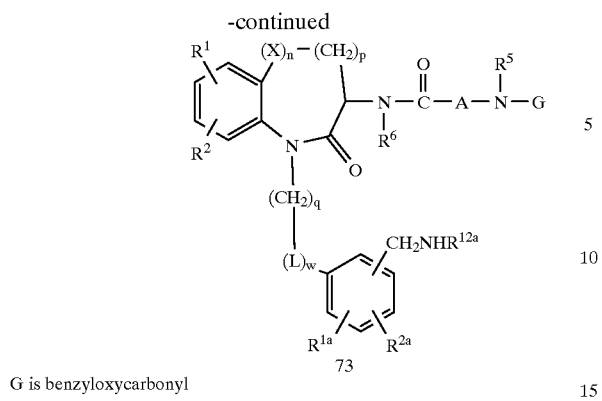

73

G is benzyloxycarbonyl

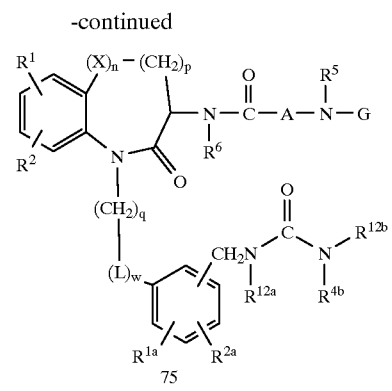

75

G is benzyloxycarbonyl

Reactions of amine 73 with the appropriate reagents to form urea-linked compounds 74 and 75 and carbamate-linked compound 76 are illustrated in Scheme 23. Terminally unsubstituted urea 74, wherein $R^{12b}$ is hydrogen, is also prepared from amine 73 by reaction with trimethylsilyl isocyanate (60; $R^{12b}$ is $(CH_3)_3Si$).

SCHEME 23

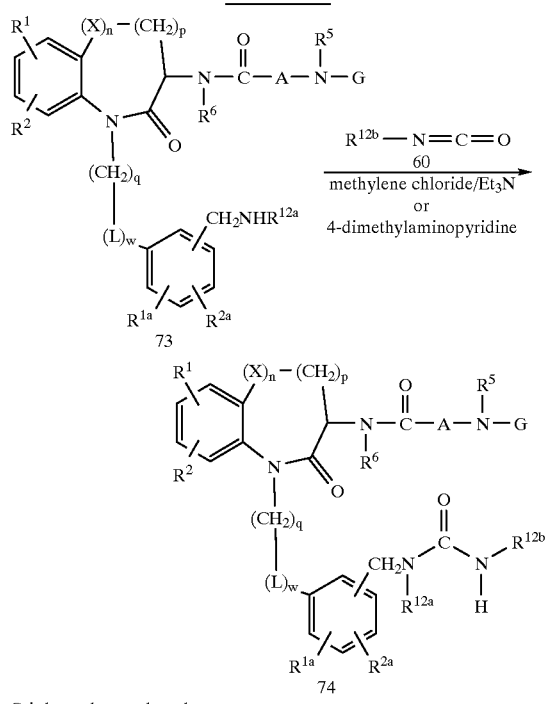

74

G is benzyloxycarbonyl

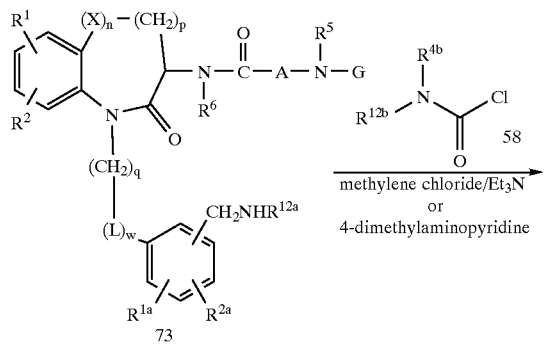

73

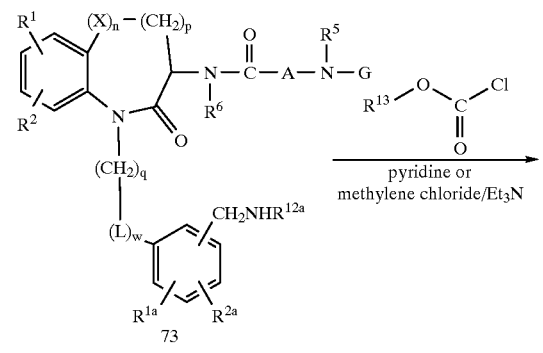

73

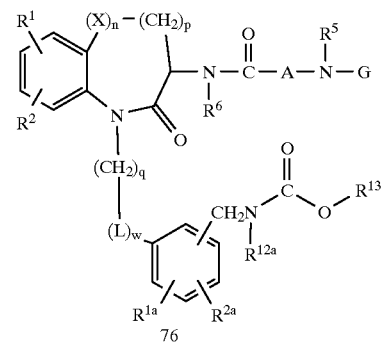

76

G is benzyloxycarbonyl

As shown in Scheme 24, hydrazide compound 77 can be prepared from intermediate 73 by a two-step procedure consisting of activation of the amine via treatment with N,N'-carbonyldiimidazole followed by treatment with the appropriately substituted hydrazine derivative $R^{4b}R^{12c}NN(R^{12b})H$.

SCHEME 24

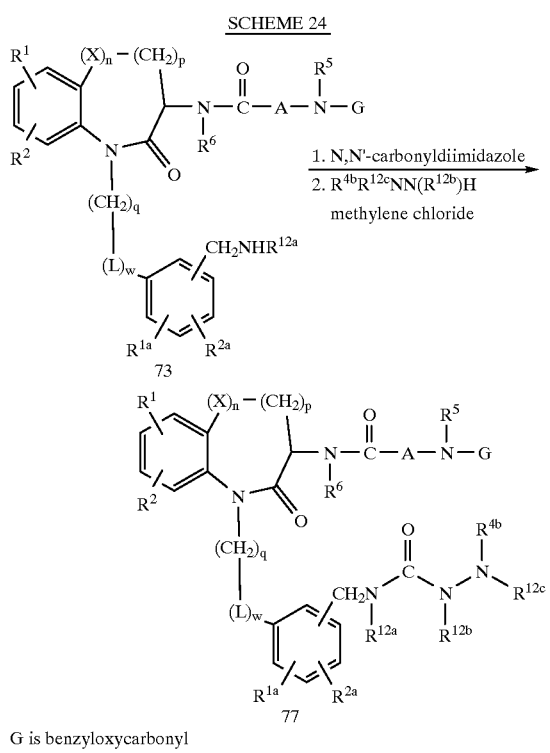

G is benzyloxycarbonyl

A useful preparation of the protected benzylamine intermediate 82 is shown in Scheme 25. Metallation of 4-bromobenzyl t-butyldiphenylsilylether 78 with n-butyllithium followed by treatment with triisopropyl borate gives the aryl boronic acid 79. Reaction of 79 with 2-bromo-N-(t-butoxycarbonyl)benzylamine 80 in the presence of tetrakis(triphenylphosphine)palladium(0) and sodium hydroxide in a mixed solvent system at elevated temperature gives the coupled product 81 in good yield. Desilylation and conversion to the O-methanesulfonate 82 is achieved by treatment with tetrabutylammonium fluoride followed by methanesulfonyl chloride. Reaction of 82 with compounds of formula V is carried out using the conditions described in Scheme 14.

SCHEME 25

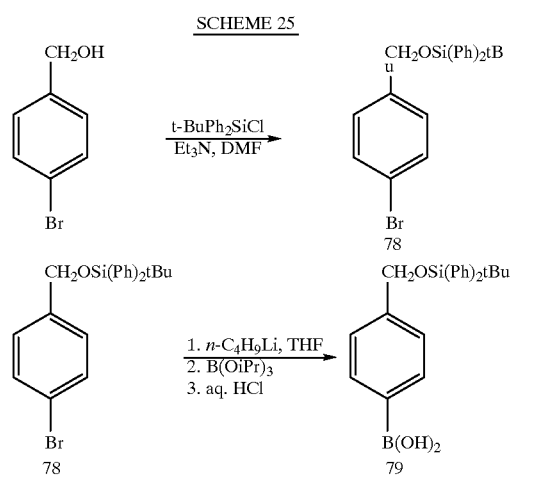

-continued

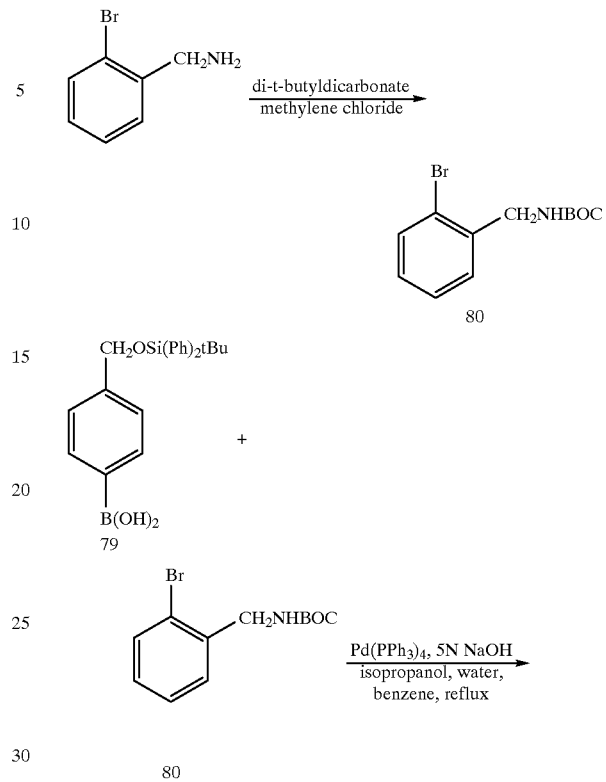

Conversion to the final products of formula I wherein $R^4$ is hydrogen, is carried out by simultaneous or sequential removal of all protecting groups from intermediate VII as illustrated in Scheme 26.

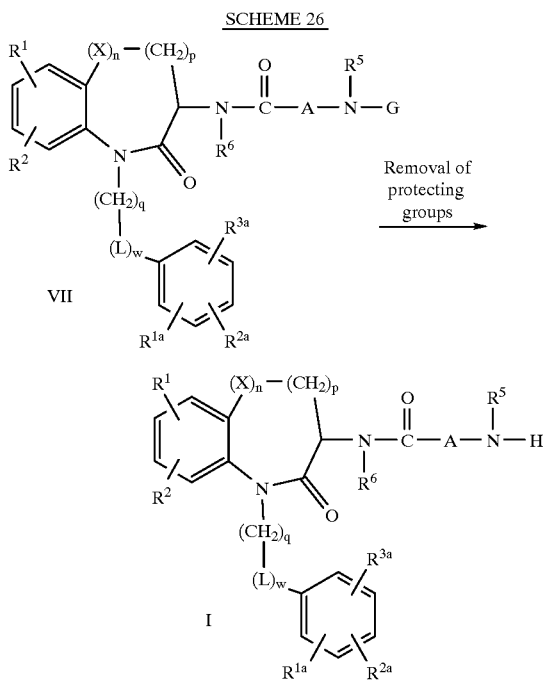

Removal of benzyloxycarbonyl (CBz) groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, N.Y. 1981.

As shown in Scheme 27, compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatography (HPLC) or by recrystallization.

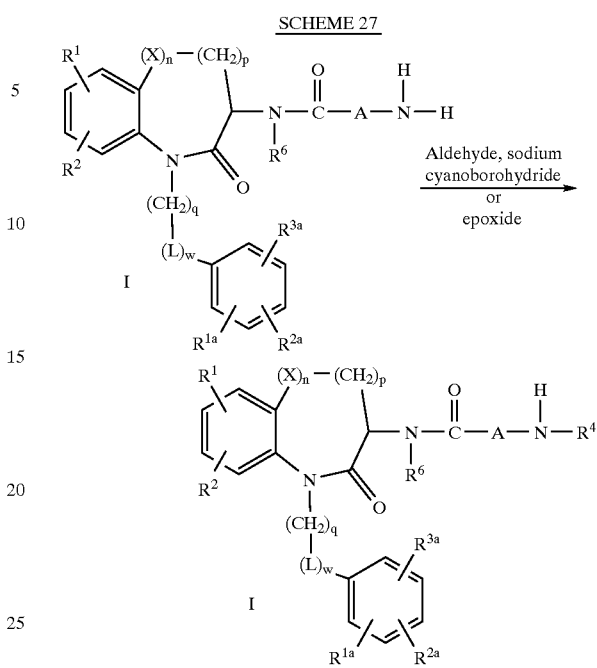

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 or GHRP-2 as described in U.S. Pat. Nos. 4,411,890; and publications WO 89/07110 and WO 89/07111 and B-HT 920 or in combination with growth hormone releasing factor and its analogs or growth hormone and its analogs. A still further use of the disclosed novel benzo-fused lactam growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis. A still further use of the disclosed novel benzo-fused lactam growth hormone secretagogues is in combination with IGF-1 to reverse the catabolic effects of nitrogen wasting as described by Kupfer, et al, *J. Clin. Invest.*, 21, 391 (1993).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids; treatment of osteoporosis; stimulation of the immune system; treatment of retardation; acceleration of wound healing; accelerating bone fracture repair; treatment of growth retardation, treating renal failure or insufficiency resulting in growth retardation; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondro-dysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS. Treatment of hyperinsulinemia including nesidioblastosis; adjuvant treatment for ovulation induction; to stimulate thymic development and prevent the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock and stimulation of wool growth in sheep.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/Kg of body weight daily are administered to patients and animals, e.g., mammals, to obtain effective release of growth hormone.

The following examples are provided for the purpose of further illustration only and are not intended to be limitations on the disclosed invention.

EXAMPLE 1

N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

1-Tetralone oxime

To 4.6 L of water at room temperature in a 4-neck 50 L flask sitting in a steam bath apparatus equipped with an overhead stirrer, a temperature probe and reflux condenser was added 3.72 Kg (27.36 mol) of sodium acetate with stirring, followed by 1.9 Kg of hydroxylamine hydrochloride (27.36 mol). To this slurry at room temperature, 12 L of ethanol was added followed by 1.994 Kg (13.68 mol) of 1-tetralone. Additional ethanol (1.7 L) was used to rinse off the funnel and added to the reaction mixture. The resulting light orange slurry was heated to 75° C. over 40 minutes and maintained at 75–85° C. for another 75 minutes. The reaction mixture was cooled with the aid of ice packed around the flask. When the internal temperature reached 32° C., the reaction mixture was pumped over 15 minutes into 60 L of ice contained in a 200 L vessel. The reaction vessel was washed with an additional 2 L of water which was added to the 200 L vessel. When the ice melted, the mixture was filtered through a filter pad and the wet cake washed with 4 L of water. The wet cake was suction dried for 1 hour then transferred to two trays and dried under vacuum at 40° C. for 2 days to give 2.094 Kg (13.01 mol, 95%) of product. $^1$H NMR (250 MHz, CDCl$_3$): δ 1.90 (m, 2H), 2.80 (t, 6 Hz, 2H), 2.88 (t, 6 Hz, 2H), 7.15–7.35 (m, 3H), 7.90 (d, 8 Hz, 1H), 8.9 (br s, 1H).

Step B:

2,3,4,5-Tetrahydro-1H-1-benzazepin-2-one

To 10 L of methanesulfonic acid in a 22 L 3-neck flask equipped with an overhead stirrer, a temperature probe, nitrogen inlet and reflux condenser, was added 2.6 Kg (18.61 mol) of phosphorus pentoxide. An additional 1.6 L of methanesulfonic acid was used to wash all the phosphorus pentoxide into the vessel. The mixture was heated at 90° C. for 2.5 hours then cooled to 50° C. using an ice bath and treated with 2.00 Kg (12.41 mol) of 1-tetralone oxime in several portions over 15 minutes. The mixture was heated at 63° C. for 10 minutes then slowly heated to 80° C. and kept at 80° C. for 3 hours. The reaction mixture was pumped into 70 L of ice then treated slowly with 11.25 L of 50% aqueous sodium hydroxide over 90 minutes at such a rate so as to maintain the temperature below 28° C. The mixture was filtered and 4 L of the filtrate was used to rinse the vessel. The wet cake (pink) was washed with 8 L of water then suction dried for 45 minutes and transferred to two trays and dried under vacuum at 40° C. for 2 days to give 1.9 Kg (11.79 mol,95%) of product. $^1$H NMR (250 MHz,CDCl$_3$): δ 2.24 (m, 2H), 2.38 (t, 6 Hz, 2H), 2.82 (t, 6 Hz, 2H), 7.03 (d, 8 Hz, 1H), 7.13 (m, 1H), 7.24 (m, 2H), 8.63 (br s, 1H).

Step C:

3-Iodo-2,3,4,5-tetrahydro-1H-1-benzazepin-2-one

A suspension of 1.8 Kg (11.17mol) of 2,3,4,5-tetrahydro-1H-1-benzazepin-2-one in a mixture of 22.33 L of methylene chloride and 11.78 L (55.83 mol) of hexamethyldisilazane was heated at reflux for 10 minutes, then cooled to 30° C. and treated with 8.503 Kg (33.5 mol) of iodine in one portion. The mixture was heated at reflux for 2.5 hours, then cooled to room temperature. Aqueous sodium sulfite containing 4.926 Kg of sodium sulfite in 44 L of water was cooled to 0° C. and into it was poured the reaction mixture in several portions with vigorous stirring while maintaining the temperature below 10° C. The reaction vessel was rinsed with 22.33 L of methylene chloride and the washing transferred to the quenching mixture. The quenching mixture was stirred vigorously and the layers allowed to separate. The aqueous layer was removed and reextracted with 22.33 L of methylene chloride. The combined organic layers were washed with 11 L of water and concentrated under vacuum to a final volume of approximately 5 L. The residue was treated with 55 L of toluene and concentrated under vacuum to a final volume of 10 L. The resulting slurry was isolated by filtration and the filter cake washed with an additional 5 L of toluene and dried under vacuum at ambient temperature for 24 hours to give 1.842 Kg (6.42 mol, 57%) of product. $^1$H NMR (200 MHz, CDCl$_3$): δ 2.6–2.8 (m, 3H), 2.93 (m, 1H), 4.64 (t, 8 Hz, 1H), 6.97 (d, 8 Hz, 1H), 7.10–7.35 (m, 3H), 7.55 (br s, 1H).

Step D:

3(R)-Amino-2,3,4,5-tetrahydro-1H-1-benzazepin-2-one, D-tartaric acid salt

3-Iodo-2,3,4,5-tetrahydro-1H-1-benzazepin-2-one (1.79 Kg, 6.24 mol) was slurried in 6.2 L of methanol and the slurry charged into an autoclave. Condensed ammonia (1.55 L) was added and the autoclave closed, with stirring, and heated to 100° C. over 1 hour. Heating at 100° C. was continued for 2 hours then the autoclave was allowed to cool to room temperature over 1 hour, during which time the internal pressure was 150–155 psi. The reaction mixture was transferred to a polyethylene jug and the autoclave rinsed with 2×8 L of methanol. The washings were concentrated under vacuum at 30° C. then combined with the reaction mixture and concentrated to near dryness under vacuum at 30° C. The resulting residue was dissolved in 4 L of ethyl acetate then concentrated to dryness under vacuum at 30° C.

Sodium chloride (712 g) was dissolved in 2 L of water and 1.0 Kg of sodium carbonate was dissolved in 6 L of water. Two liters of the sodium carbonate solution was added to the concentrated residue and the resulting slurry transferred to an extraction flask. Another 2 L portion of the sodium carbonate solution was added to the residue flask and the solution transferred to the extraction flask. The remaining sodium carbonate solution was used in the same way. The sodium chloride solution was added to the sodium carbonate/aminolactam emulsion and the resulting mixture stirred for 10 minutes then extracted with four 6 L portions of methylene chloride. The combined methylene chloride layers were concentrated to dryness; the residue was treated with 2 L of 200 proof ethanol and the resulting slurry concentrated to dryness under vacuum to give 1.171 Kg of crude product.

The crude product was slurried in 8 L of ethanol and treated with 900 g of D-tartaric acid in one portion. Water (7 L) was added and the mixture heated to 77° C., then additional ethanol (45 L) was added and heating continued. The solution was cooled to 43° C. and treated with the seed slurry. (The seed slurry was prepared by the route described above starting with 10.50 g of crude product and 9.1 g of D-tartaric acid.) The solution was aged at room temperature for 48 hours. The slurry formed was removed by filtration and the wet cake washed with 1.8 L of ethanol. The resulting filter cake was suction dried with nitrogen bleeding for 20 hours, then transferred into a drying tray and dried under vacuum for 24 hours to give 354 g (1.085 mol, 17.4%) of the product. $^1$H NMR (250 MHz, CDCl$_3$): δ 2.13 (m, 1H), 2.51 (m, 2H), 2.73 (m, 2H), 3.68 (t, 6 Hz, 1H), 3.98 (s, 2H), 7.05 (d, 8 Hz, 1H), 7.16 (t, 8 Hz, 1H), 7.30 (m, 2H), 7.6 (br s, 5H), 10.26 (br s, 1H).

Step E:

3(R)-Amino-2,3,4,5-tetrahydro-1H-1-benzazepin-2-one

A solution of 229.23 g (0.700 mol) of 3(R)-amino-2,3,4, 5-tetrahydro-1H-1-benzazepin-2-one, D-tartrate in 4.1 L of water was treated with 194 g (1.40 mol) of potassium carbonate. Subsequent portions of 100 g and 135 g of potassium carbonate were added until the pH was 10.5. The mixture was extracted with four 4 L portions of methylene chloride which were then combined and dried over magnesium sulfate. The aqueous layer was treated with 1.4 Kg of sodium chloride and reextracted with four 4 L portions of methylene chloride which were then combined and dried over magnesium sulfate. The two 16 L batches of extracts were combined, filtered and concentrated to dryness under vacuum to give 115.5 g of product which contained 1.6% of an impurity identified as 7-iodo-3(R)-amino-2,3,4,5-tetrahydro-1H-1-benzazepin-2-one.

A solution of 107.02 g (0.607 mol) of the intermediate obtained above in 1.712 L of ethanol was hydrogenated at room temperature and 40 psi over 4.00 g of 10% palladium on carbon for 4 hours. The catalyst was removed by filtration through solkaflok and the filtrate concentrated to dryness under vacuum to give 101.08 g (0.574 mol, 94.4%) of product.

Step F:

4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step G without purification. $^1$H NMR (200 MHz, CDCl$_3$): δ 1.45 (s, 6H), 2.75 (d, 3 Hz, 2H), 5.9 (br s, 1H).

Step G:

N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step F), 800 mL of methylene chloride, 150 mL of triethylamine (1.08 mol) and 10.9 g (0.089 mol) of 4-dimethylaminopyridine. To the stirred solution, at room temperature was added dropwise over 15 minutes a solution of 235 g (1.077 mol) of di-t-butyldicarbonate in 300 mL of methylene chloride. The reaction mixture was stirred at room temperature overnight, then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step H without purification. $^1$H NMR (200MHz, CDCl$_3$): δ 1.50 (s, 9H), 1.54 (s, 6H), 2.77 (s, 2H).

Step H:

3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0–5° C. and treated dropwise with 890 mL of 1.0 M aqueous lithium hydroxide over 30 minutes. The reaction mixture was stirred at 0–5° C. for 2 hours, then diluted with 1 L of ether and 1 L of water. The layers were allowed to separate and the aqueous layer was reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to give 173 g of a yellow oil that solidified upon standing. The material was slurried with warm hexane, then filtered and dried under high vacuum to afford 168.5 g (0.775 mol, 87%) of product as a white solid. $^1$H NMR (200 MHz, CDCl$_3$): δ 1.39 (s, 6H), 1.44 (s, 9H), 2.72 (s, 2H). FAB-MS: calculated for $C_{10}H_{19}NO_4$ 217; found 218 (M+H,54%).

Step I:

3-t-Butoxycarbonylamino-3-methyl-N-[2,3,4,5-tetrahydro-2-oxo-1H-1-benzazepin-3(R)-yl]-butanamide A solution of 8.70 g (49.4 mmol) of 3(R)-amino-2,3,4,5-tetrahydro-1H-1-benzazepin-2-one (Step E) in 100 mL of methylene chloride was treated with 10.73 g (49.4 mmol) of 3-t-butoxycarbonylamino-3-methylbutanoic acid (Step H) and 13.8 mL of triethylamine (10.0 g, 99 mmol, 2 eq.). The reaction flask was immersed in an ambient temperature water bath then 26 g of benzotriazol-1-yloxytris (dimethylamino)phosphonium hexafluorophosphate (59 mmol, 1.2 eq) was added all at once and the mixture stirred at room temperature for 2 hours. The reaction mixture was added to 300 mL of ethyl acetate and washed three times with 5% aqueous citric acid, twice with saturated aqueous sodium bicarbonate and once with saturated aqueous sodium chloride. The organic layer was removed, dried over magnesium sulfate, filtered and the filtrate concentrated under vacuum.

The residue was purified by preparative high pressure liquid chromatography on silica, eluting with ethyl acetate/hexane (4:1), to afford 17.42 g (46.4 mmol, 94%) of the product as a white solid. $^1$H NMR (200 MHz, CDCl$_3$): δ 1.37 (s, 6H), 1.44 (s, 9H), 1.95 (m, 1H), 2.46 (d, 15 Hz, 1H), 2.59 (d, 15 Hz, 1H), 2.6–3.0, (m, 3H), 4.53 (m, 1H), 5.30 (br s, 1H), 6.72 (d, 7 Hz, 1H), 6.98 (d, 8 Hz, 1H), 7.1–7.3 (m, 3H), 7.82 (br s, 1H). FAB-MS: calculated for $C_{20}H_{29}N_3O_4$ 375; found 376 (M+H,70%).

Step J:

4-Methyl-2'-nitro-1,1'-biphenyl

A vigorously stirred mixture of 4-tolylboronic acid (34 g, 0.25 mol) and 2-bromo-1-nitrobenzene (34 g, 0.168 mol) in a mixture of 5N sodium hydroxide (170 mL), water (57 mL), isopropanol (215 mL) and benzene (1080 mL) under a nitrogen atmosphere was treated with (tetrakis) triphenylphosphine palladium (0) (11.9 g). The stirred bilayer reaction mixture was heated at reflux for 3 hours. The cooled reaction mixture was filtered through Celite and the filter cake washed with fresh benzene. The organic layer was separated and washed with water (3x), dried over magnesium sulfate and filtered. The filtrate was evaporated under vacuum and the residue (46.1 g) purified by preparative high pressure liquid chromatography on silica gel, eluting with hexane/ethyl acetate (20:1) gave 28.05 g of the product. EI-MS: calculated for $C_{13}H_{11}NO_2$ 213; found 213 (M$^+$). $^1$H NMR (400 MHz, CDCl$_3$): δ 2.38 (s, 3H), 7.20 (m, 4H), 7.43 (m, 2H), 7.59 (t, 1H), 7.8 (d, 1H).

Step K:

4-Bromomethyl-2'-nitro-1,1'-biphenyl

A solution of 4-methyl-2'-nitro-1,1'-biphenyl (Step J) (6.0 g, 28.2 mmol), N-bromosuccinimide (4.99 g, 28.2 mmol) and AIBN (653 mg) in 75 mL of carbon tetrachloride was heated at reflux until a negative potassium iodide test was obtained (1.5 h). The reaction mixture was cooled and filtered. The filtrate was evaporated under vacuum to yield 8.41 g of crude product. $^1$H NMR revealed the product composition was approximatly 75% monobromo and 10% dibromo, in addition to 15% of unreacted starting material. $^1$H NMR (200MHz, CDCl$_3$): δ 4.53 (s, 2H), 7.2–7.7 (m, 7H), 7.85 (m, 1H). EI-MS: calculated for $C_{14}H_{10}BrN$ 272; found 272,274 (M$^+$).

Step L:

4-Hydroxymethyl-2'-nitro-1,1'-biphenyl

A solution of 4-bromomethyl-2'-nitro-1,1'-biphenyl (7.27 g, 24.8 mmol) in acetic acid (50 mL) was treated with potassium acetate (4.88 g, 49.1 mmol). The reaction mixture was heated at reflux for 2 hours. After cooling, the reaction mixture was filtered and the precipitate was washed with acetic acid (2x). The filtrate was evaporated under vacuum and the residue was triturated with ethyl ether. The ether layer was washed consecutively with water, saturated aqueous sodium bicarbonate (3x) and water. The organic layer was dried over magnesium sulfate, filtered and evaporated under vacuum. The residue was dissolved in methanol (50 mL) and treated with a 6N methanolic potassium hydroxide solution (5 mL). After stirring for 1 hour at room temperature, thin layer chromatography indicated the absence of starting material. The reaction mixture was acidified with acetic acid and evaporated under vacuum. The residue was washed free of acetic acid by washing an etheral solution with aqueous sodium bicarbonate and water. After drying over magnesium sulfate, the ethereal solution was evaporated under vacuum. The residue was purified by preparative high pressure liquid chromatography on silica gel, eluting with hexane/ethyl acetate (3:1) to give 2'-nitro-1,1'-biphenyl-4-carboxaldehyde (620 mg) followed by 4-hydroxymethyl-2'-nitro-1,1'-biphenyl (3.06 g, 13.4 mmol, 54%).

Step M:

4-(Tetrahydropyranyloxy)methyl-2'-nitro-1,1'-biphenyl

A solution of 4-hydroxymethyl-2'-nitro-1,1'-biphenyl (3.06 g, 13.4 mmol) and 3,4-dihydropyran (1.8 mL, 20.1 mmol) in methylene chloride (50 mL) under a nitrogen atmosphere was treated with pyridinium p-toluenesulfonate (336 mg, 1.34 mmol). After stirring for 3 hours at room temperature, thin layer chromatography indicated that no starting material remained. The reaction mixture was diluted with ethyl ether (300 mL). The ether extracts were washed with saturated aqueous sodium chloride, dried over magnesium sulfate and filtered. The filtrate was evaporated under vacuum and the residue purified by preparative high pressure liquid chromatography on silica gel, eluting with hexane/ethyl acetate (10:1) to give 4.47 g of the product.

Step N:

4-(Tetrahydropyranyloxy)methyl-2'-amino-1,1'-biphenyl

A solution of 4-(tetrahydropyranyloxy)methyl-2'-nitro-1,1'-biphenyl (4.12 g, 13.2 mmol) in 100 mL of methanol was hydrogenated at 40 psi in the presence of 5% palladium on carbon. After 2 hours, uptake of hydrogen was complete. The reaction mixture was filtered through diatomacious earth, and the filter cake washed with methanol. The filtrate was evaporated under vacuum to yield 3.57 g of the product.

Step O:

4-Hydroxymethyl-2'-(methoxycarbonyl)amino-1,1'-biphenyl

A solution of (tetrahydropyranyloxy)methyl-2-amino-1,1'-biphenyl (500 mg, 1.76 mmol) in pyridine (6 mL) was treated with methyl chloroformate (0.41 mL, 5.3 mmol). The reaction mixture was stirred at room temperature for 48 hours. The reaction mixture was evaporated under vacuum. The residue was taken up in ethyl ether and washed with water (3x). The ether layer was dried over magnesium sulfate, filtered and evaporated under vacuum to yield 547 mg of crude 4-(tetrahydropyranyloxy)methyl-2'-(methoxycarbonyl)amino-1,1'-biphenyl.

The crude 4-(tetrahydropyranyloxy)methyl-2'-(methoxycarbonyl)amino-1,1'-biphenyl (250 mg) dissolved in 4 mL of methanol was treated with 1 mL of 10% methanolic p-toluenesulfonic acid. The reaction mixture was stirred at room temperature for 1 hour. The reaction mixture was made basic by the addition of saturated aqueous sodium bicarbonate, then diluted with ethyl acetate. The organic layer was washed with water (2x), dried over magnesium sulfate and evaporated under vacuum. The residue was purified by preparative thin layer chromatography on silica gel, eluting with methylene chloride/methanol (100:3) to give 137 mg of the product. FAB-MS (Li$^+$ spike): calculated for $C_{15}H_{15}NO_3$ (257); found 264 (M+Li). $^1$H NMR (200 MHz,CDCl$_3$): δ3.51 (s, 3H), 4.75 (s, 2H), 6.62 (br s, 11H), 7.14 (dd, 2H), 7.34 (dd, 1H), 7.4 (dd, 4H).

Step P:

4-Bromomethyl-2'-(methoxycarbonyl)amino-1,1'-biphenyl

A solution of 4-hydroxymethyl-2'-(methoxycarbonyl)-amino-1,1'-biphenyl (239 mg, 0.93 mmol) in methylene chloride (4 mL) was treated with bromotrimethylsilane (3.0 mL, 22.7 mmol). The reaction mixture was stirred at room temperature for 18 hours. The reaction mixture was diluted with additional methylene chloride and washed with saturated aqueous sodium chloride. After drying over magnesium sulfate, the filtered organic layer was evaporated under vacuum The residue was purified by preparative thin layer chromatography on silica gel, eluting with methylene chloride-methanol (100:3) to give 190 mg of the product.

Step Q:

N-[1-[[2'-[(Methoxycarbonyl)amino][1,1'-biphenyl]-4-yl]methyl]-2,3,4,5-tetrahydro-2-oxo-1H-1-benzazepin-3 (R)-yl]-3-t-butoxycarbonylamino-3-methylbutanamide A solution of 222 mg (0.594 mmol) of 3-t-butoxycarbonyl-amino-3-methyl-N-[2,3,4,5-tetrahydro-2-oxo-1H-1-benzazepin-3(R)-yl]-butanamide (Step I) in 6 mL of dry dimethylformamide was treated with 30 mg of 60% sodium hydride oil dispersion (18 mg NaH, 0.75 mmol, 1.3 eq). The reaction mixture was stirred at room temperature for 30 minutes. To the solution was added 190 mg (0.594 mmol) of solid 4-bromomethyl-2'-(methoxycarbonyl) amino-1,1'-biphenyl. After stirring at room temperature for 1 hour, the reaction mixture was diluted with ethyl acetate followed by 50 mL of water. The organic layer was washed with water (4×), dried over magnesium sulfate, filtered and evaporated under vacuum. The residue was purified by preparative thin layer chromatography on silica gel, eluting with methylene chloride/methanol (100:3) to give 231 mg (0.376 mmol, 63%) of the product. $^1$H NMR (400 MHz, CDCl$_3$): δ 1.23 (s, 3H), 1.33 (s, 3H), 1.39 (s, 9H), 1.85 (m, 1H), 2.40 (dd, 2H), 2.49 (m, 1H), 2.54 (m, 2H), 3.68 (s, 3H), 4.53 (m, 1H), 4.94 (d, 1H), 5.17 (d, 1H), 6.53 (br s, 1H), 6.66 (d, 1H), 7.2 (m, 12H), 8.09 (d, 1H).

Step R:

N-[1-[[2'-[(Methoxycarbonyl)amino][1,1'-biphenyl]-4-yl]methyl]-2,3,4,5-tetrahydro-2-oxo-1H-1-benzazepin-3 (R)-yl]-3-amino-3-methylbutanamide, trifluoroacetate A solution of 86 mg (0.14 mmol) of the intermediate obtained in Step Q in 2 mL of methylene chloride was treated with 1.0 mL of trifluoroacetic acid. After stirring at room temperature for 1 hour, all volatiles were removed under vacuum and the residue purified by medium pressure liquid chromatography on C8, eluting with methanol/0.1% aqueous trifluoroacetic acid (60:40). The fractions containing the product were combined and solvents removed under vacuum. The residue was lyophilized from water to give 69 mg (0.13 mmol, 96%) of the title compound as a white solid. FAB-MS: calculated for $C_{30}H_{34}N_4O_4$ 514; found 515 (M+H). $^1$H NMR (400 MHz, CD$_3$OD): δ 1.34 (s, 3H), 1.39 (s, 3H), 2.12 (m, 1H), 2.31 (m, 1H), 2.52 (dd, 2H), 2.6 (m, 2H), 3.54 (br s, 3H), 4.40 (dd, 1H), 5.02 (d, 1H), 5.28 (d, 1H), 7.30 (m, 12H), 7.54 (br s, 1H).

EXAMPLE 2

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[(2'-Nitro)[1,1'-biphenyl]-4-yl]methyl]-2,3,4,5-tetrahydro-2-oxo-1H-1-benzazepin-3(R)-yl]amino-3-methylbutanamide Prepared from 4-bromomethyl-2'-nitro-1,1'-biphenyl (Example 1, Step K) and 3-t-butoxycarbonylamino-3-methyl-N-[2,3,4,5-tetrahydro-2-oxo-1H-1-benzazepin-3 (R)-yl]-butanamide (Example 1, Step I) by the procedure described in Example 1, Step Q. $^1$H NMR (400 MHz, CDCl$_3$): δ 1.34 (s, 6H), 1.41 (s, 9H), 1.83 (m, 1H), 2.35–2.70 (m, 5H), 4.50 (m, 1H), 4.84 (d, 15 Hz, 1H), 5.23 (d, 15 Hz, 1H), 5.27 (s, 1H), 6.64 (d, 7 Hz, 1H), 7.1–7.6 (m, 11H), 7.80 (d, 8 Hz, 1H). FAB-MS: calculated for $C_{33}H_{38}N_4O_6$ 586; found 587 (M+H).

Step B:

N-[1-[[(2'-Amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 7.79 g (13.23 mmol) of the intermediate obtained in Step A in 200 mL of methanol containing 0.9 g of 5% palladium on carbon was hydrogenated at 40 psi. When the uptake of hydrogen was complete, the catalyst was removed by filtration through Celite. The filtrate was concentrated under vacuum to yield 6.6 g (11.9 mmol, 90%) of product. FAB-MS: calculated for $C_{33}H_4N_4O_4$ 556; found 557(M+H). $^1$H NMR (400 MHz, CDCl$_3$): δ 1.32 (s, 6H), 1.39 (s, 9H), 1.87 (m, 1H), 2.51 (dd, 1H), 2.59 (m, 1H), 4.51 (m, 1H), 4.89 (d, 1H), 5.15 (d, 1H), 5.32 (br s, 1H), 6.71 (d, 1H), 6.81 (s, 1H), 7.21 (m, 10H).

Step C:

N-[1-[[2'-[(Methylaminocarbonyl)amino][1,1'-biphenyl]-4-yl]methyl]-2,3,4,5-tetrahydro-2-oxo-1H-1-benzazepin-3 (R)-yl]-3-t-butoxycarbonylamino-3-methylbutanamide A solution of 88.4 mg (0.158 mmol) of the intermediate obtained in Step B in 4 mL of methylene chloride at room temperature was treated with 0.5 mL of methyl isocyanate (8.5 mmol). The reaction mixture was stirred at room temperature for 18 hours, when all starting material was consumed as indicated by thin layer chromatography. The reaction was evaporated under vacuum and the residue passed over silica gel. Elution with ethyl acetate/n-hexane (3:1) yielded 66 mg (0.11 mmol, 68%) of product. $^1$H NMR (400 MHz, CDCl$_3$): δ 1.21 (s, 3H), 1.23 (s, 3H), 1.39 (s, 9H), 1.89 (m, 1H), 2.49 (dd, H), 2.60 (m, 2H), 2.69 (s, 3H), 4.50 (m, 1H), 4.95 (d, 1H), 5.06 (d, 1H), 5.26 (br s, 1H), 6.24 (br s, 1H), 6.70 (d, 1H), 7.22 (m, 11H), 7.71 (d, 1H).

Step D:

N-[1-[[2'-[(Methyl aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 66 mg (0.11 mmol) of the intermediate obtained in Step C in 2 mL of methylene chloride was treated with 2 mL of trifluoroacetic acid. The reaction mixture was stirred at room temperature for 1 hour, when thin layer chromatography indicated that no starting material remained. The reaction mixture was evaporated to dryness under vacuum and the residue purified by medium pressure liquid chromatography on C8, eluting with methanol/0.1% aqueous trifluoroacetic acid (60:40). Fractions containing the product were combined and evaporated under vacuum and the residue lyophilized from water to give 26 mg (0.051 mmol, 46%) of the title compound as a white solid. FAB-MS: calculated for $C_{30}H_{35}N_5O_3$ 513; found 536 (M+Na). $^1$H NMR (400 MHz, CD$_3$OD): δ 1.34 (s, 3H), 1.37 (s, 3H), 2.13 (m, 1H), 2.39 (m, 1H), 2.54 (dd, 1H), 2.63 (s, 3H), 3.29 (dd, 1H), 4.95 (d, 1H), 5.11 (d, 1H), 7.22 (m, 10H), 7.60 (d, 1H).

EXAMPLE 3

N-[1-[[2'-[(Ethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[2'-[(Ethylaminocarbonyl)amino][1,1'-biphenyl]-4-yl]methyl]-2,3,4,5-tetrahydro-2-oxo-1H-1-benzazepin-3 (R)-yl]-3-t-butoxycarbonylamino-3-methylbutanamide Prepared from N-[1-[[(2'-amino)[1,1'-biphenyl]-4-yl]-methyl]-2,3,4,5-tetrahydro-2-oxo-1H-1-benzazepin-3(R)- yl]-3-t-butoxycarbonylamino-3-methylbutanamide (Example 2, Step B) and ethyl isocyanate by the procedure described in Example 2, Step C.

Step B:

N-[1-[[2'-[(Ethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step A by the procedure described in Example 2, Step D. FAB-MS: calculated for $C_{31}H_{37}N_5O_3$ 527; found 550(M+Na). $^1$H NMR (400 MHz, $CD_3OD$): δ 1.04 (t, 3H), 1.34 (s, 3H), 1.38 (s, 3H), 2.14 (m, 1H), 2.34 (m, 1H), 2.52 (dd, 2H), 2.62 (m, 2H), 3.09 (q, 2H), 4.41 (dd, 1H), 5.01 (d, 1H), 5.24 (d, 11H), 7.24 (m, 11H), 7.60 (d, 1H).

EXAMPLE 4

N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from N-[1-[[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) and isopropyl isocyanate by the procedure described in Example 2, Step C. $^1$H NMR (400 MHz, $CDCl_3$): δ 1.06 (d, 3H) 1.07 (d, 3H), 1.32 (s, 3H), 1.39 (s, 9H), 1.88 (m, 1H), 2.48 (dd, 1H), 2.50 (m, 1H), 2.62 (m, 2H), 3.80 (m, 1H), 4.52 (m, 1H), 4.98 (d, 1H), 5.10 (d, 1H), 5.28 (br s, 1H), 6.08 (br s, 1H), 6.68 (br s, 1H), 7.22 (m, 11H), 7.70 (d, 1H).

Step B:

N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step A by the procedure described in Example 2, Step D. FAB-MS: calculated for $C_{32}H_{39}N_5O_3$ 541; found 541(M$^+$). $^1$H NMR (400 MHz, $CD_3OD$): δ 1.05 (dd, 6H), 1.34 (s, 3H), 1.37 (s, 3H), 2.5 (m, 1H), 2.34 (m, 1H), 2.5 (m, 1H), 2.64 (m, 2H), 3.73 (m, 1H), 4.41 (dd, 1H), 5.02 (d, 1H), 5.24 (d, 1H), 7.3 (m, 12H), 7.63 (d, 1H).

EXAMPLE 5

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 445 mg (0.80 mmol) of N-[1-[[(2'-amino)-[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) in 3 mL of methylene chloride under a nitrogen atmosphere was treated with 4 mL (29.5 mmol) of trimethylsilyl isocyanate. The reaction mixture was stirred at room temperature for 18 hours. The reaction mixture was evaporated under vacuum and the residue was passed over silica gel. Elution with ethyl acetate/hexanes (4:1) yielded 211 mg (0.35 mmol, 44%) of product. FAB-MS: calculated for $C_{34}H_{41}N_5O_5$ 599: found 622 (M+Na). $^1$H NMR (400 MHz, $CDCl_3$): δ 1.31 (s, 3H), 1.38 (s, 3H), 1.39 (s, 9H), 1.90 (m, 1H), 2.48 (dd, 2H), 2.60 (m, 2H), 4.48 (m, 1H), 4.95 (d, 1H), 5.08 (d, 1H), 5.28 (br s, 1H), 6.66 (br s, 1H), 6.78 (d, 1H), 7.22 (m, 11H), 7.72 (d, 1H).

Step B:

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step A by the procedure described in Example 2, Step D. FAB-MS: calculated for $C_{29}H_{33}N_5O_3$ 499; found 500(M+H). $^1$H NMR (400 MHz, $CD_3OD$): δ 1.34 (s, 3H), 1.37 (s, 3H), 2.14 (m, 2H), 2.34 (m, 1H), 2.50 (dd, 1H), 2.65 (m, 2H), 4.42 (dd, 1H), 5.02 (dd, 1H), 5.25 (d, 1H), 7.27 (m, 10, H), 7.60 (d, 1H).

EXAMPLE 6

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[(2'-Isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 2.0 g (3.6 mmol) of N-[1-[[(2'-amino)[1,1'-biphenyl]-4-yl]methyl]-2,3, 4,5-tetrahydro-2-oxo-1H-1-benzazepin-3(R)-yl-3-t-butoxycarbonylamino-3-methylbutanamide (Example 2, Step B) and 2.0 mL of triethylamine (14 mmol) in 40 mL of methylene chloride under a nitrogen atmosphere was cooled to −10° C. and treated with 2.12 g (7.15 mmol) of triphosgene in one portion. An exotherm occurred. The reaction was stirred at room temperature for 1.5 hours when no starting amine was detected by thin layer chromatography on silica (hexane/ethyl acetate (1:1)). The reaction mixture was diluted with 40 mL of hexane and filtered. The filtrate was passed over 150 g of silica gel and eluted with hexane/ethyl acetate (1:1) to give 1.65 g (2.84 mmol, 79%) of the product. $^1$H NMR (400 MHz, $CDCl_3$): δ 1.34 (s, 6H), 1.39 (s, 9H), 1.84 ((m, 1H), 2.40 (m, 1H), 2.49 (dd, 1H), 2.52 (m, 1H), 4.51 (m, 1H), 4.88 (d, 1H), 5.25 (d, 1H), 5.34 (br s, 1H), 6.71 (d, 1H), 7.20 (m, 12H).

Step B:

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 100 mg (0.17 mmol) of the intermediate obtained in Step A in 2 mL of methylene chloride was treated with 0.017 mL of morpholine (0.19 mmol). The reaction mixture was stirred at room temperature for 1 hour when thin layer chromatography showed no remaining isocyanate. To the reaction mixture was added 1 mL of trifluoroacetic acid. The reaction mixture was stirred at room temperature for 0.5 hours. The reaction mixture was evaporated under vacuum and the residue purified by preparative medium pressure reverse phase liquid chromatography on C8, eluting with methanol/0.1% aqueous trifluoroacetic acid (65:35). The fractions containing the product were combined and evaporated under vacuum and the residue was lyophilized from water to afford 88 mg (0.15 mmol, 88%) of the title compound as a white solid. FAB-MS: calculated for $C_{33}H_{39}N_5O_4$ 569; found 592 (M+Na). $^1$H NMR (400 MHz, CD$_3$OD): δ 1.35 (s, 3H), 1.39 (s, 3H), 2.12 (m, 1H), 2.35 (m, 1H), 2.52 (dd, 2H), 2.60 (m, 2H), 3.25 (m, 4H), 3.54 (m, 4H), 4.40 (dd, 1H), 4.95 (d, 1H), 5.30 (d, 1H), 7.3 (m, 12H).

EXAMPLE 7

N-[1-[[2'-[(Piperazinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and piperazine by the methods described in Example 6. FAB-MS: calculated for C$_{33}$H$_{40}$N$_6$O$_3$ 568; found 593 (M+Na). $^1$H NMR (400 MHz, CD$_3$OD): δ 1.27 (s, 3H), 1.30 (s, 3H), 2.07 (m, 1H), 2.30 (m, 1H), 2.4 (dd, 2H), 2.59 (m, 2H), 3.20 (dd, 4H), 3.30 (dd, 4H), 4.40 (dd, 1H), 4.90 (d, 1H), 5.33 (d, 1H), 7.30 (m, 12H).

EXAMPLE 8

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and ethanolamine by the procedure described in Example 6, Step A. FAB-MS: calculated for C$_{36}$H$_{45}$N$_5$O$_6$ 643; found 666 (M+Na). $^1$H NMR (400 MHz, CDCl$_3$): δ 1.29 (s, 3H), 1.31 (s, 3H), 1.38 (s, 9H), 1.90 (m, 1H), 2.5 (dd, 2H), 2.58 (m, 2H), 2.7 (m, 1H), 3.21 (t, 2H), 3.54 (m, 2H), 4.49 (m, 1H), 4.88 (d, 1H), 5.10 (d, 1H), 6.81 (d, 1H), 7.21 (m, 11H), 7.74 (d, 1H).

Step B:

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step A by the procedure described in Example 6, Step B. FAB-MS: calculated for C$_{31}$H37N$_5$O$_4$ 543: found 545. $^1$H NMR (400 MHz, CD3OD): δ 1.34 (s, 3H), 1.37 (s, 3H), 2.14 (m, 1H), 2.34 (m, 1H), 2.52 (dd, 2H), 2.64 (m, 2H), 3.20 (t, 2H), 3.51 (t, 2H), 4.41 (dd, 1H), 5.02 (d, 1H), 5.20 (d, 1H), 7.24 (m, 11H), 7.62 (d, 1H).

EXAMPLE 9

N-[1-[[2'-[[(2-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 1-amino-2-propanol by the procedures described in Example 6. FAB-MS: calculated for C$_{32}$H$_{39}$N$_5$O$_4$ 557; found 580 (M+Na). $^1$H NMR (400 MHz, CD$_3$OD): δ 1.00 (d, 3H), 1.34 (s, 3H), 1.37 (s, 3H), 2.14 (m, 1H), 2.34 (m, 1H), 2.52 (dd, 2H), 2.68 (m, 2H), 3.01 (dd, 1H), 4.41 (dd, 1H), 5.02 (d, 1H), 5.21 (d, 1H), 7.25 (m, 11H), 7.62 (d, 1H).

EXAMPLE 10

N-[1-[[2'-[[(3-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 3-amino-1-propanol by the procedures described in Example 6. FAB-MS: calculated for C$_{32}$H$_{39}$N$_5$O$_4$ 557; found 580 (M+Na). $^1$H NMR (400 MHz, CD$_3$OD): δ 1.34 (s, 3H), 1.38 (s, 3H), 1.60 (m, 2H), 2.18 (m, 1H), 2.35 (m, 1H), 2.52 (dd, 2H), 2.65 (m, 3H), 3.39 (m, 2H), 3.52 (m, 2H), 4.42 (dd, 1H), 5.04 (d, 1H), 5.21 (d, 1H), 7.28 (m, 11H), 7.59 (d, 1H).

EXAMPLE 11

N-[1-[[2'-[[(2,3-Dihydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 3-amino-1,2-propanediol by the procedures described in Example 6. FAB-MS: calculated for C$_{32}$H39N$_5$O$_4$ 557; found 580(M+Na). $^1$H NMR (400 MHz, CD$_3$OD): δ 1.34 (s, 3H), 1.37 (s, 3H), 2.14 (m, 1H), 2.34 (m, 1H), 2.51 (dd, 1H), 2.66 (m, 2H), 3.09 (m, 1H), 3.2 (m, 2H), 3.42 (m, 2H), 3.59 (m, 1H), 4.41 (dd, 1H), 5.05 (d, 1H), 5.17 (d, 1H), 7.25, (m, 10H), 7.59 (d, 1H).

EXAMPLE 12

N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

4-Methylphenyltrimethylstannane 41.4 L of 1.0 M p-tolylmagnesium bromide in diethyl ether (41.4 mol) was added dropwise, maintaining the temperature below −5° C., over 4 hours to a solution of 546 g (2.79 mol) of trimethyltin chloride in tetrahydrofuran (4 L) under nitrogen at −10° C. The suspension was allowed to warm slowly to room temperature over 12 hours then saturated ammonium chloride solution (1 L) was added followed by sufficient water (approximately 1 L) to dissolve the precipitate. The solution was extracted with ether-hexane (1:1) (1×4 L, 3×2 L). The combined organic phases were washed with brine, dried over magnesium sulfate and the solvents removed under vacuum. Purification by flash chromatography on silica gel eluting with hexane/ethyl acetate (95:5) gave a pale yellow oil containing white crystals of 4,4'-dimethylbiphenyl which were removed by filtration to leave 711.3 g (100%) of product. $^1$H NMR (300 MHz, CDCl$_3$): δ 0.30 (s, 9H), 2.34 (s, 3H), 7.19 (d, 7.7 Hz, 2H), 7.40 (d, 7.7 Hz, 2H).

Step B:

4-Methyl-2'-acetyl-1,1'-biphenyl

A vigorously stirred solution of 13.25 g (66 mmol) of 2'-bromoacetophenone and 22.8 g (89 mmol) of 4-methylphenyl-trimethylstannane in 190 mL of dimethylformamide under a nitrogen atmosphere was treated with 8.64 g (12 mmol) of bis(triphenylphosphine)palladium(II) chloride and the resulting mixture heated at 150° C. for 6 hours. The reaction mixture was cooled, poured into water (1000 mL) and the resultant suspension extracted with ethyl ether. The combined extracts were washed with water (4×), dried over magnesium sulfate and evaporated under vacuum. The residue was purified by preparative high pressure liquid chromatography on silica gel, eluting with hexane/ethyl acetate (10:1) to give 9.8 g (47 mmol, 71%) of product as an oil. El-MS: calculated for $C_{15}H_{14}O$ 210: found 210 ($M^+$). $^1$H NMR (200 MHz, $CDCl_3$): δ 1.98 (s, 3H), 2.37 (s, 3H), 7.20 (s, 4H), 7.3–7.5 (m, 4H).

Step C:

4-Methyl-2'-hydroxy-1,1'-biphenyl

A solution of 4.2 g (20.0 mmol) of 4-methyl-2'-acetyl-1-1'-biphenyl (Step B) in methylene chloride under a nitrogen atmosphere was treated with 8.98 g of 85% m-chloroperbenzoic acid. The resultant suspension was cooled to 0° C. and treated dropwise with 1.54 mL of trifluoroacetic acid over a 10 minute period. The reaction mixture was stirred at room temperature for 16 hours. The reaction mixture was diluted with 50 mL of methylene chloride and the solution was washed successively with 50 mL of 10% sodium sulfite, 50 mL of saturated aqueous potassium carbonate and water (3×50 mL). The organic layer was removed and dried over magnesium sulfate, then evaporated under vacuum to yield 4.1 g of an oil. The oil was dissolved in 20 mL of methanol and treated with 2.0 mL of 5N aqueous sodium hydroxide. The reaction mixture was stirred at room temperature for 1 hour. The pH of the solution was adjusted to 5–6 with acetic acid. After the methanol was removed under vacuum, the residue was taken up in ether, washed with water, dried over magnesium sulfate, filtered and evaporated under vacuum to yield 3.0 g of crude product which was purified by preparative high pressure liquid chromatography on silica, eluting with hexane/ethyl acetate (10:1). In this manner, 1.85 g (10.0 mmol, 50%) of the product was obtained as an oil. $^1$H NMR (200 MHz, $CDCl_3$): δ 2.40 (s, 3H), 5.22 (br s, 1H), 6.96 (m, 2H), 7.2–7.4 (m, 6H). EI-MS: calculated for $C_{13}H_{12}O$ 184; found 184 ($M^+$,100%).

Step D:

4-Methyl-2'-acetoxy-1,1'-biphenyl

A solution of 1.0 g (5.4 mmol) of 4-methyl-2'-hydroxy-1,1'-biphenyl in 2.0 mL of pyridine was treated with 2 mL of acetic anhydride. The reaction mixture was stirred at room temperature for 5 hours. The solvent was removed under vacuum to yield 1.11 g (4.9 mmol, 90%) of the product as an oil. $^1$H NMR (200 MHz, $CDCl_3$): δ 2.07 (s, 3H), 2.36 (s, 3H), 7.07 (dd; 3, 8 Hz; 1H), 7.15 (d, 8 Hz, 2H), 7.2–7.4 (m, 5H).

Step E:

4'-Bromomethyl-2-acetoxy-1,1'-biphenyl

Prepared from 4-methyl-2'-acetoxy-1,1'-biphenyl by the procedure described in Example 1, Step K. $^1$H NMR (200 MHz, $CDCl_3$): δ 2.05 (s, 3H), 4.50 (s, 2H), 7.08 (m, 1H), 7.20–7.45 (m, 7H).

Step F:

N-[1-[[(2'-Acetoxy)[1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from 4-bromomethyl-2'-acetoxy-1,1'-biphenyl and 3-t-butoxycarbonylamino-3-methyl-N-[2,3,4,5-tetrahydro-2-oxo-1H-1-benzazepin-3(R)-yl]-butanamide (Example 1, Step I) by the procedure described in Example 1, Step Q. $^1$H NMR (200 MHz, $CDCl_3$): δ 1.38 (s, 6H), 1.45 (s, 9H), 1.85 (m, 1H), 2.02 (s, 3H), 2.35–2.65 (m, 5H), 4.52 (m, 1H), 4.84 (d, 15 Hz, 1H), 5.30 (d, 15 Hz, 1H), 6.71 (d, 7 Hz, 1H), 7.1–7.4 (m, 12H).

Step G:

N-[1-[[(2'-Hydroxy)[1,1'-biphenyl]-4-yl]methyl]-2,3,4,5-tetrahydro-2-oxo-1H-1-benzazepin-3(R) -yl ]-3-t-butoxycarbonylamino-3-methylbutanamide A solution of 469 mg (0.87 mmol) of the intermediate obtained in Step F in 25 mL of methanol at room temperature was treated with 5 mL of aqueous 5N sodium hydroxide. After stirring at room temperature for 1 hour, the reaction mixture was evaporated under vacuum and the residue dissolved in methylene chloride, dried over magnesium sulfate and filtered. The filtrate was evaporated under vacuum to yield 450 mg of crude product which was used in the next step without purification.

Step H:

N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 100 mg (approx. 0.2 mmol) of the crude intermediate obtained in Step G in 5 mL of methylene chloride was treated with 1.0 mL of methyl isocyanate (17 mmol) and 0.1 mL of 1,8-diazabicyclo[5.4.0]undec-7-ene under a nitrogen atmosphere. The reaction mixture was stirred at room temperature for 10 minutes and then evaporated under vacuum to give 146 mg of crude product. $^1$H NMR (400 MHz, $CDCl_3$): δ 1.32 (s, 3H), 1.33 (s, 3H), 1.39 (s, 9H), 2.12 (m, 1H), 2.33 (m, 1H), 2.52 (dd, 1H), 2.57 (m, 2H), 2.59 (s, 3H), 4.38 (dd, 1H), 4.8 (d, 1H), 5.26 (d, 1H), 7.10 (d, 11H), 7.36 (m, 1 1H).

Step I:

N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 72 mg of the crude intermediate obtained in Step H in 3.5 mL of methylene chloride was treated with 1.0 mL of trifluoroacetic acid. After stirring at room temperature for 15 minutes, the reaction mixture was evaporated under vacuum and the residue purified by reverse phase medium pressure liquid chromatography on C8, eluting with methanol/0.1% aqueous trifluoroacetic acid (60:40). Fractions containing the product were combined, solvents removed under vacuum and the residue lyophilized from water to give 34 mg (0.066 mmol) of the title compound as a white solid. FAB-MS: alculated for $C_{30}H_{34}N_4O_4$ 514; found 537 (M+Na). $^1$H NMR (400 MHz, $CD_3OD$): δ 1.34 (s, 3H), 1.38 (s, 3H), 2.12 (m, 1H), 2.33 (m, 1H), 2.52 (dd, 1H), 2.57 (m, 2H), 2.59 (s, 3H), 4.38 (dd, 1H), 4.8 (d, 1H), 5.26 (d, 1H), 7.10 (d, 1H), 7.36 (m, 1H).

EXAMPLE 13

N-[1-[[2'-[(Methylaminothiocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[(2'-Isothiocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide, and N-[1-[[2'-[(methylaminothiocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 300 mg (0.60 mmol) of N-[1-[[(2'-amino)[1,1'-biphenyl]-4-yl]methyl]-2,3,4,5-tetrahydro-2-oxo-1H-

1-benzazepin-3(R)-yl]-3-t-butoxycarbonylamino-3-methylbutanamide (Example 2, Step B) and 1.8 g of methyl isothiocyanate (25 mmol) in 15 mL of benzene under a nitrogen atmosphere was heated at reflux for 24 hours. The reaction mixture was evaporated under vacuum and the residue purified by preparative thin layer chromatography on silica gel, eluting with ethyl acetate/hexane (3:1) to give 69 mg of a faster moving product identified as N-[1-[[(2'-isothiocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide. FAB-MS: calculated for $C_{34}H_{38}N_4O_4S$ 598; found 621 (M+Na). $^1$H NMR (400 MHz, $CDCl_3$): δ 1.35 (s, 3H), 1.36 (s, 3H), 1.40 (s, 9H), 1.84 (m, 1H), 2.48 (dd, 2H), 2.52 (m, 3H), 4.50 (m, 1H), 4.86 (d, 1H), 5.29 (d, 1H), 6.68 (d, 1H), 7.14 (m, 1H), 7.30 (M, 11H).

The slower moving band yielded 122 mg of material identified as N-[1-[[2'-[(methylaminothiocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide. FAB-MS: calculated for $C_{35}H_{43}N_5O_4S$ 629: found 652 (M+Na). $^1$H NMR (400 MHz, $CDCl_3$): δ 1.32 (s, 3H), 1.33 (s, 3H), 1.40 (s, 9H), 1.85 (m, 1H), 2.48 (dd, 2H), 2.55 (m, 3H), 2.95 (s, 3H), 4.50 (m, 1H), 4.88 (s, 1H), 5.20 (s, 1H), 6.68 (d, 1H), 7.22 (m, 12H).

Step B:

N-[1-[[2'-[(Methylaminothiocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 122 mg (0.19 mmol) of N-[1-[[2'-[(methylaminothiocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide in 3 mL of methylene chloride was treated with 1.0 mL of trifluoroacetic acid. After 1 hour thin layer chromatography indicated that no starting material was present. Solvents were removed under vacuum and the residue purified by reverse phase medium pressure liquid chromatography on C8, eluting with methanol/0.1% aqueous trifluoroacetic acid (60:40). The fractions containing the product were combined, solvents evaporated under vacuum and the residue was lyophilized from water to give 84 mg (0.16 mmol, 84%) of the title compound as a white solid. FAB-MS: calculated for $C_{30}H_{35}N_4O_2$ 529; found 531. $^1$H NMR (400 MHz, $CD_3OD$): δ 1.32 (s, 3H), 1.38 (s, 3H), 2.11 (m, 1H), 2.30 (m, 1H), 2.53 (dd, 2H), 2.70 (m, 2H), 2.72 (s, 3H), 4.4 (dd, 1H), 4.89 (d, 1H), 5.81 (d, 1H), 7.3 (m, 12H).

EXAMPLE 14

N-[1-[[2'-[(Aminothiocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 100 mg (0.17 mmol) of N-[1-[[(2'-isothiocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 13, Step A) in 5 mL of methanol was treated with gaseous anhydrous ammonia for 5 minutes. Thin layer chromatography revealed no starting isothiocyanate was present. The reaction mixture was evaporated under vacuum and the residue was dissolved in 3 mL of methylene chloride and treated with 1 mL of trifluoroacetic acid. After 1 hour at room temperature the reaction mixture was evaporated under vacuum and the residue purified by reverse phase medium pressure liquid chromatography on C8, eluting with methanol/0.1% aqueous trifluoroacetic acid (60:40). Fractions containing the product were combined, solvents removed under vacuum and the residue lyophilized from water to give 53 mg of the title compound as a white solid. FAB-MS: calculated for $C_{29}H33N5O_2S$ 515; found 516 (M+H). $^1$H NMR (400 MHz, $CD_3OD$): δ 1.34 (s, 3H), 1.38 (s, 3H), 2.12 (m, 1H), 2.30 (m, 1H), 2.54 (dd, 2H), 2.60 (m, 2H), 4.42 (dd, 1H), 4.92 (d, 1H), 5.26 (d, 1H), 7.30 (m, 12H).

EXAMPLE 15

N-[1-[[2'-[(Dimethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide trifluoroacetate Step A:

4-(Tetrahydropyranyloxy)methyl-2'-isocyanato-1,1'-biphenyl

A solution of 200 mg (0.70 mmol) of 4-(tetrahydropyranyloxy)methyl-2'-amino-1,1'-biphenyl (Example 1, Step N) and 0.40 mL of triethylamine in 10 mL of methylene chloride under a nitrogen atmosphere was treated with triphosgene (420 mg, 0.24 mmol). The reaction mixture was stirred at room temperature for 30 minutes when 1thin layer chromatography on silica (hexane/ethyl acetate; 2:1) revealed no remaining amine. The reaction mixture was evaporated under vacuum to yield the crude product which was used in the next step without purification.

Step B:

4-Hydroxymethyl-2'-(dimethylaminocarbonyl)amino-1,1'-biphenyl

A solution of the crude intermediate from Step A in 4 mL of methanol was treated with 4 mL of 40% aqueous dimethylamine. After stirring at room temperature for 15 minutes, the reaction mixture was evaporated under vacuum and the residue dissolved in 4 mL of methanol and treated with 1 mL of 10% methanolic p-toluenesulfonic acid. After 15 minutes at room temperature, the reaction mixture was treated with saturated aqueous sodium bicarbonate. The mixture was diluted with water then extracted with methylene chloride. The organic layer was dried and evaporated under vacuum; the residue was purified by preparative thin layer chromatography on silica gel, eluting with hexane/ethyl acetate (2:1) to afford 133 mg of product.

Step C:

4-Bromomethyl-2'-(dimethylaminocarbonyl)amino-1,1'-biphenyl

A solution of the intermediate obtained in Step B in 4 ml of methylene chloride was treated with 0.16 mL (1.21 mmol) of trimethylsilylbromide. The reaction mixture was stirred at room temperature for 18 hours. T he reaction mixture was diluted with methylene chloride then washed with aqueous saturated sodium chloride (2×). The organic layer was dried over magnesium sulfate, filtered and evaporated under vacuum to yield 133 mg of crude product. $^1$NMR (400 Hz, $CDCl_3$): δ 2.78 (s, 6H), 4.5 (s, 2H), 6.4 (br s, 1H), 7.08 (t, 1H), 7.16 (dd, 1H), 7.34 (m, 4H), 7.49 (d, 1H), 8.10 (d, 1H).

Step D:

N-[1-[[2'-[(Dimethylaminocarbonyl)amino][1,1'-biphenyl]-4-yl]methyl]-2,3,4,5-tetrahydro-2-oxo-1H-1-benzazepin-3(R)-yl]-3-amino-3-methlbutanamide trifluoroacetate A solution of 147 mg (0.39 mmol) of 3-t-butoxycarbonylamino-3-methyl-N-[2,3,4,5-tetrahydro-2-oxo-1H-1-benzazepin-3(R)-yl]butanamide (Example 1, Step I) in 5 mL of dry dimethylformamide was treated with 20 mg of 60% sodium hydride/oil dispersion (12 mg NaH, 0.5 mmol, 1.3 eq.). The reaction mixture was stirred at room temperature for 30 minutes then 133 mg of 4-bromomethyl-2'-(dimethylaminocarbonyl)amino-1,1'-biphenyl was added. After stirring at room temperature for 2 hours, the reaction mixture was diluted with ethyl acetate. The mixture was washed with water (4×) and the organic layer dried over magnesium sulfate, filtered and evaporated under vacuum. The residue was dissolved in 4 mL of methylene chloride and treated with 1 mL of trifluoroacetic acid. After stirring at room temperature for 1.5 hours, solvents were removed under vacuum and the residue purified by reverse phase medium pressure liquid chromatography on C8, eluting with methanol/0.1% aqueous trifluoroacetic acid (65:35). Fractions containing the product were combined, solvents removed under vacuum and the residue lyophilized from water to give 116 mg of the title compound as a white solid. FAB-MS: calculated for $C_{34}H_{37}N_5O_3$ 527; found 529. $^1$H NMR (400 MHz, $CD_3OD$): δ 1.34 (s, 3H), 1.40 (s, 3H), 2.15 (m, 1H), 2.34 (m, 1H), 2.54 (dd, 2H), 2.59 (m, 2H), 2.78 (s, 6H), 4.44 (dd, 1H), 4.88 (d, 1H), 5.38 (d, 1H), 7.28 (m, 11H), 7.49 (d, 1H).

EXAMPLE 16

N-[1-[[2'-[[(1,3-Dihydroxyprop-2-yl)aminocarbonyl]amino][1,1'-biphenyl]-4-yl]methyl]-2,3,4,5-tetrahydro-2-oxo-1H-1-benzazepin-3(R)-yl]-3-amino-3-methylbutanamide trifluoroacetate Step A:
N-[1-[[2'-[(1,3-Dihydroxyprop-2-yl)aminocarbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 125 mg (0.23 mmol) of N-[1-[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) and 0.10 mL (0.72 mmol) of triethylamine in 5 mL of methylene chloride under a nitrogen atmosphere was cooled to −10° C. and treated with 133 mg (0.45 mmol) of triphosgene. The reaction mixture was allowed to warm to room temperature and stirred for 1 hour. The reaction mixture was recooled to −10° C. and additional triethyl amine (0.30 mL, 0.23 mmol) was added. The reaction mixture was treated with serinol hydrochloride (280 mg, 2.20 mmol) in one portion. The reaction mixture was stirred at room temperature when thin layer chromatography (hexane/ethyl acetate: 1:1) indicated no remaining isocyanate. The reaction mixture was evaporated under vacuum to give the crude product.

Step B:
N-[1-[[2'-[[(1,3-Dihydroxyprop-2-yl)aminocarbonyl]amino][1,1'-biphenyl]-4-yl]methyl]-2,3,4,5-tetrahydro-2-oxo-1H-1-benzazepin-3(R)-yl]-3-amino-3-methylbutanamide trifluoroacetate A solution of the crude intermediate obtained in Step A in 5 mL of methylene chloride was treated with 2 mL of trifluoroacetic acid.

After stirring at room temperature for 1 hour, the reaction mixture was evaporated under vacuum and the residue purified by reverse phase medium pressure liquid chromatography on C8, eluting with methanol/0.1% aqueous trifluoroacetic acid (55:45). Fractions containing the product were combined, solvents removed under vacuum and the residue lyophilized from water to give 66 mg (0.096 mmol, 42% over two steps) of the title compound as a white solid. FAB-MS: calculated for $C_{32}H_{39}N_5O_5$ 573; found 596 (M+Na). $^1$NMR (400 MHz, $CD_3OD$): δ 1.34 (s, 3H), 1.37 (s, 3H), 2.14 (m, 1H), 2.30 (m, 1H), 2.48 (dd, 2H), 2.69 (m, 2H), 3.52 (m, 4H), 3.70 (m, 1H), 4.40 (dd, 1H), 5.05 (d, 1H), 5.20 (d, 1H), 7.25 (m, 11H), 7.62 (d, 1H).

EXAMPLE 17

N-[1-[[2'-[[[2(R)-Hydroxypropylamino]carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and (R)-(−)-1-amino-2-propanol by the methods described in Example 6. FAB-MS: calculated for $C_{32}H_{39}N_5O_4$ 557; found 580 (M+Na). $^1$H NMR (400 MHz, $CD_3OD$): δ 1.09 (d, 31), 1.34 (s, 3H), 1.37 (s, 3H), 2.15 (m, 1H), 2.35 (m, 1H), 2.52 (dd, 2H), 2.65 (m, 2H), 2.95 (dd, 1H), 3.16 (dd, 1H), 3.75 (m, 1H), 4.82 (dd, 1H), 5.02 (d, 1H), 5.20 (d, 1H), 7.27 (m, 11H), 7.61 (d, 1H).

EXAMPLE 18

N-[1-[[2'-[[[2(S)-Hydroxypropylamino]carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and (S)-(+)-1-amino-2-propanol by the methods described in Example 6. FAB-MS: calculated for $C_{32}H_{39}N_5O_4$ 557; found 581 (M+Na). $^1$H NMR (400 MHz, $CD_3OD$): δ 1.09 (d, 3H), 1.34 (s, 3H), 1.37 (s, 3H), 2.15 (m, 1H), 2.45 (m, 1H), 2.55 (dd, 2H), 2.68 (m, 2H), 3.02 (dd, 1H), 3.16 (dd, 1H), 3.75 (m, 1H), 4.41 (dd, 1H), 5.06 (d, 1H), 5.22 (d, 1H), 7.27 (m, 11H), 7.62 (d, 1H).

EXAMPLE 19

N-[1-[[2'-[[[[1-Hydroxyprop-2(R)-yl]amino]carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and (R)-2-amino-1-propanol by the methods described in Example 6. FAB-MS: calculated for $C_{32}H_{39}N_5O_4$ 557; found 580 (M+Na). $^1$H NMR (400 MHz, $CD_3OD$): δ 1.07 (d, 3H), 1.34 (s, 3H), 1.37 (s, 3H), 2.15 (m, 1H), 2.35 (m, 1H), 2.51 (dd, 2H), 3.41 (m, 2H), 3.75 (m, 1H), 4.41 (dd, 1H), 5.03 (d, 1H), 5.21 (d, 1H), 7.25 (m, 11H), 7.64 (d, 1H).

EXAMPLE 20

N-[1-[[2'-[(Hydrazinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]4-yl]methyl]-2,3,4,5-tetrahydro-2-oxo-1H-1-benzazepin-3(R)-yl]-3-t- butoxycarbonylamino-3-methylbutanamide and anhydrous hydrazine by the methods described in Example 6. FAB-MS: calculated for $C_{29}H_{35}N_6O_3$ 514: found 537 (M+Na). $^1$H NMR (400 MHz, $CD_3OD$): δ 1.35 (s, 3H), 1.38 (s, 3H), 2.29 (m, 1H), 2.35 (m, 1H), 2.57 (dd, 1H), 2.62 (m, 2H), 4.46 (dd, 1H), 5.30 (d, 1H), 7.29 (m, 10H), 7.73 (d, 11H).

EXAMPLE 21

N-[1-[[2'-[(2,2-Dimethylhydrazinocarbonyl)amino] [1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 1,1-dimethylhydrazine by the methods described in Example 6. FAB-MS: calculated for $C_{31}H_{38}N_6O_3$ 542; found 565 (M+Na). $^1$H NMR (400 MHz, $CD_3OD$): δ 1.34 (s, 3H), 1.38 (s, 3H), 2.14 (m, 1H), 2.30 (s, 6H), 2.36 (m, 1H), 2.52 (dd, 1H), 2.64 (m, 2H), 4.28 (dd, 1H), 5.00 (dd, 1H), 5.30 (dd, 1H), 7.26 (m, 10H), 7.90 (d, 1H).

EXAMPLE 22

N-[1-[[2'-[[(Carboxymethylamino)carbonyl]amino] [1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:
N-[1-[[2'-[[(t-Butoxycarbonylmethylamino)carbonyl] amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from N-[1-[[(2'-amino)[1,1'-biphenyl]-4-yl] methyl]-2,3,4,5-tetrahydro-2-oxo-1H-1-benzazepin-3(R)-yl]-3-t-butoxycarbonylamino-3-methylbutanamide (Example 2, Step B) and glycine t-butyl ester hydrochloride by the procedure described in Example 16, Step A.

Step B:
N-[1-[[2'-[[(Carboxymethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate, and N-[1-[[2'-[[(Methoxycarbonylmethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of the crude intermediate obtained in Step A in 4 mL of methylene chloride was treated with 2 mL of trifluoroacetic acid. After stirring at room temperature for 1 hour, the reaction mixture was evaporated under vacuum and the residue purified by reverse phase medium pressure liquid chromatography on C8, eluting with methanol/0.1% aqueous trifluoroacetic acid (55:45). The early fractions containing the product were combined, solvents removed under vacuum and the residue was lyophilized from water to give 60 mg of the title compound as a white solid. FAB-MS: calculated for $C_{31}H_{35}N_5O_5$ 557: found 558 (M+H). $^1$H NMR (400 MHz, $CD_3OD$): δ 1.34 (s, 3H), 1.38 (s, 3H), 2.15 (m, 1H), 2.34 (m, 1H), 2.52 (dd, 2H), 2.68 (m, 2H), 3.84 (s, 2H), 4.42 (s, 1H), 5.05 (d, 1H), 5.20 (d, 1H), 7.25 (m, 11H), 7.64 (d, 1H).

Later fractions were combined, solvents removed under vacuum and the residue lyophilized from water to give 18 mg of N-[1-[[2'-[[(methoxycarbonylmethylamino)carbonyl] amino][1,1'-biphenyl]-4-yl]methyl]-2,3,4,5-tetrahydro-2-oxo-1H-1-benzazepin-3(R)-yl]-3-amino-3-methylbutanamide, trifluoroacetate. FAB-MS: calculated for $C_{32}H_{37}N_5O_5$ 571; found 594 (M+Na). $^1$H NMR (400 MHz, $CD_3OD$): δ 1.34 (s, 3H), 1.39 (s, 3H), 2.15 (m, 1H), 2.35 (m, 1H), 2.52 (dd, 2H), 2.66 (m, 2H), 2.71 (s, 3H), 2.87 (s, 2H), 4.42 (dd, 1H), 5.05 (d, 1H), 5.22 (d, 1H), 7.28 (m, 11H), 7.61 (d, 1H).

EXAMPLE 23

N-[1-[[2'-[[(Methoxycarbonylmethylamino) carbonyl]amino][1,1'-biphenyl]-4-yl]methyl]-2,3,4, 5-tetrahydro-2-oxo-1H-1-benzazepin-3(R)-yl]-3-amino-3-methylbutanamide, trifluoroacetate The title compound was prepared from N-[1-[[2'-[(t-butoxycarbonylmethylamino)carbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide by the procedure described in Example 22, Step B. FAB-MS: calculated for $C_{32}H_{37}N_5O_5$ 571; found 594 (M+Na). $^1$H NMR (400 MHz, $CD_3OD$): δ 1.34 (s, 3H), 1.39 (s, 3H), 2.15 (m, 1H), 2.35 (m, 1H), 2.52 (dd, 2H), 2.66 (m, 2H), 2.71 (s, 3H), 2.87 (s, 2H), 4.42 (dd, 1H), 5.05 (d, 1H), 5.22 (d, 1H), 7.28 (m, 11H), 7.61 (d, 1H).

EXAMPLE 24

N-[1-[[2'-[(Benzylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and benzyl amine by the procedures described in Example 6. $^1$H NMR (400 MHz,$CD_3OD$): δ 1.34 (s,3H), 1.37 (s,3H), 2.13 (m,1H), 2.33 (m,1H), 2.45–2.70 (m,4H), 4.28 (s,2H), 4.42 (dd,1H), 5.00 (d,1H), 5.25 (d,1H), 7.1–7.4 (m,16H), 7.62 (d,1H). FAB-MS: calculated for $C_{36}H_{39}N_5O_3$, 589; found 590 (M+H).

EXAMPLE 25

N-[1-[[2'-[(Phenylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and aniline by the procedures described in Example 6. FAB-MS: calculated for $C_{35}H_{37}N_5O_3$, 578; found 598 (M+Na). $^1$H NMR (400 MHz, $CD_3OD$): δ 1.32 (s,3H), 1.35 (s,3H), 2.11 (m,1H), 2.30 (m,1H), 2.52 (m,2H), 2.65 (m,1H), 4.40 (dd,1H), 5.03 (d,1H), 5.21 (d,1H), 6.99 (m,2H), 7.15–7.45 (m,9H), 7.74 (d,1H).

EXAMPLE 26

N-[1-[[2'-[(Hydroxyaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro- 2-oxo-1H-1-benzazepin-3(R)-yl]-3-t-butoxycarbonylamino-3-methylbutanamide and O-(trimethylsilyl)hydroxylamine by the procedures described in Example 6. FAB-MS: calculated for $C_{29}H_{33}N_5O_4$ 515: found 538 (M+Na). $^1$H NMR (400 MHz, $CD_3OD$): δ 1.26 (s, 1H), 1.28 (s, 3H), 2.11 (m, 1H), 2.32 (m, 1H), 2.52 (dd, 2H), 2.60 (m, 2H), 4.40 (dd, 1H), 5.0 (d, 1H), 5.24 (d, 1H), 7.25 (m, 11H), 8.0 (d, 1H).

EXAMPLE 27

N-[1-[[2'-[4-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

4-Methyl-2'-(4-nitrophenoxy)-1,1'-biphenyl

A solution of 184 mg (1.0 mmol) of 4-methyl-2'-hydroxy-1,1'-biphenyl (Example 12, Step C) in 3 mL of dimethylformamide was treated with 55 mg of 60% sodium hydride (33 mg NaH, 1.4 mmol). The reaction mixture was stirred at room temperature for 30 minutes then treated with 169 mg (1.19 mmol) of 1-fluoro-4-nitrobenzene. The reaction mixture was heated at 100° C. for 2 hours. The reaction mixture was cooled, poured into 50 mL of water and the resultant mixture was extracted with ethyl ether. The combined extracts were washed with water, dried over magnesium sulfate, filtered and evaporated under vacuum. The residue was chromatographed on silica, eluting with hexane/ethyl acetate (10:1) to give 271 mg (0.89 mmol,88%) of the product. FAB-MS: calculated for $C_{19}H_{15}NO_2$ 305: found 306 (M+H). $^1$H NMR (200 MHz,$CDCl_3$): δ 2.28 (s,3H), 6.82 (d,2H), 7.19 (d,3H), 7.2–7.5 (m,5H), 8.05 (d,2H).

Step B:

4-Bromomethyl-2'-(4-nitrophenoxy)-1,1'-biphenyl

Prepared from 4-methyl-2'-(4-nitro-phenoxy)-1,1'-biphenyl by the procedure described in Example 1, Step K. $^1$H NMR (200 MHz,$CDCl_3$): δ 4.43 (s,2H), 6.83 (d,8Hz, 2H), 7.09 (d,8 Hz,1H), 7.3–7.5 (m,7H), 8.04 (d,8 Hz,2H).

Step C:

N-[1-[[2'-(4-Nitrophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide Prepared from 4-bromomethyl-2'-(4-nitrophenoxy)-1,1'-biphenyl and 3-t-butoxycarbonylamino-3-methyl-N-[2,3,4,5-tetrahydro-2-oxo-1H-1-benzazepin-3(R)-yl]-butanamide (Example 1, Step I) by the procedure described in Example 1, Step Q. $^1$H NMR (200 MHz,$CDCl_3$): δ 1.32 (s,6H), 1.38 (s,9H), 1.78 (m,1H), 2.3–2.7 (m,5H), 4.47 (m,1H), 4.75 (d,15 Hz,1H), 5.13 (d,15 Hz,1H), 6.63 (d,7 Hz,1H), 6.75 (d,8 Hz,2H), 7.05–7.50 (m,11H), 7.97 (s,1H), 7.98 (d,8 Hz,2H).

Step D:

N-[1-[[2'-(4-Aminophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide A solution of 282 mg (0.415 mmol) of the intermediate obtained in Step C in 30 mL of methanol was hydrogenated at 40 psi in the presence of 5% palladium on carbon. After uptake of hydrogen was complete, the mixture was filtered through Celite and the filtrate was evaporated under vacuum to yield 264 mg of product.

Step E:

N-[1-[[2'-[4-[(Methylaminocarbonyl)amino]phenoxy]-[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 264 mg (0.40 mmol) of the intermediate obtained in Step D in 5 mL of methylene chloride under a nitrogen atmosphere was treated with 0.90 mL (15 mmol) of methyl isocyanate. The reaction mixture was stirred at room temperature for 18 hours, then all volatiles were removed under vacuum and the residue purified by chromatography on silica gel, eluting with ethyl acetate/hexane (3:1) to give 287 mg (0.40 mmol,100%) of product. $^1$H NMR (400 MHz, $CD_3OD$): δ 1.24 (s,3H), 1.31 (s,6H), 1.39 (s,9H), 2.00 (m,1H), 2.30 (m,1H), 2.42 (m,3H), 2.50 (dd,1H), 2.73 (s,3H), 4.32 (dd,1H), 4.82 (d,1H), 5.24 (d,1H), 6.70 (m,2H), 6.95 (d,1H), 7.2 (m,13H).

Step F:

N-[1-[[2'-[4-[(Methylaminocarbonyl)amino]phenoxy]-[1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 287 mg (0.40 mmol) of the intermediate obtained in Step E in 3 mL of methylene chloride was treated with 1.5 mL of trifluoroacetic acid. The reaction mixture was stirred at room temperature for 1 hour then evaporated under vacuum and the residue purified by reverse phase medium pressure liquid chromatography on C8, eluting with methanol/0.1% aqueous trifluoroacetic acid (50:50). Fractions containing the product were combined, solvents removed under vacuum and the residue lyophilized from water to give 165 mg (0.23 mmol,57%) of the title compound as a white solid. FAB-MS: calculated for $C_{36}H_{39}N_5O_4$ 605; found 628 (M+Na). $^1$H NMR (400 MHz, $CD_3OD$): δ 1.33 (s,3H), 1.36 (s,3H), 2.06 (m,1H), 2.26 (m,1H), 2.48 (m,4H), 2.74 (s,3H), 4.36 (dd,1H), 4.8 (d,1H), 5.17 (d,1H).

EXAMPLE 28

N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

4-Methyl-2'-(2-nitrophenoxy)-1,1'-biphenyl

Prepared from 4-methyl-2'-hydroxy-1,1'-biphenyl (Example 12, Step C) and 1-fluoro-2-nitrobenzene by the procedure described in Example 27, Step A. $^1$H NMR (200 MHz,$CDCl_3$): δ 2.30 (s,3H), 6.74 (dd;2,8 Hz;1H), 6.9–7.5 (m,10H), 7.84 (dd;2,8 Hz;1H).

Step B:

4-Bromomethyl-2'-(2-nitrophenoxy)-1,1'-biphenyl

Prepared from 4-methyl-2'-(2-nitrophenoxy)-1,1'-biphenyl by the procedure described in Example 1, Step K. $^1$H NMR (400 MHz,$CD_3OD$): δ 4.52 (s,2H), 7.4 (m,11H), 7.86 (d,1H).

Step C:

N-[1-[[2'-(2-Nitrophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide Prepared from 4-bromomethyl-2'-(2-nitrophenoxy)-1,1'-biphenyl and 3-t-butoxycarbonylamino-3-methyl-N-[2,3,4,5-tetrahydro-2-oxo-1H-1-benzazepin-3(R)-yl]-butanamide (Example 1, Step I) by the procedure described in Example 1, Step Q. $^1$H NMR (200 MHz,$CDCl_3$): δ 1.32 (s,6H), 1.38 (s,9H), 1.78 (m,1H), 2.3–2.7 (m,5H), 4.47 (m,1H), 4.75 (d, 15 Hz,1H), 5.13 (d,15 Hz, 1H), 6.63 (d,7 Hz, 1H), 6.75 (d,8 Hz,2H), 7.05–7.50 (m,/11H), 7.97 (s,1H), 7.98 (d,8 Hz,2H).

Step D:

N-[1-[[2'-(2-Aminophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide Prepared from the intermediate obtained in Step C by the procedure described in Example 27, Step D.

Step E:

N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from the intermediate obtained in Step D by the procedure described in Example 27, Step E.

Step F:

N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step E by the procedure described in Example 27, Step F. FAB-MS: calculated for $C_{36}H_{39}N_5O_4$ 605; found 628 (M+Na). $^1$H NMR (400 MHz,CD$_3$OD): δ 1.38 (s, 3H), 1.42 (s, 3H), 2.08 (m, 1H), 2.38 (m, 3H), 2.54 (dd, 2H), 2.8 (s, 3H), 4.39 (dd, 1H), 4.85 (d, 1H), 5.3 (d, 1H), 6.51 (d, 1H), 5.8 dt, 1H), 6.84 (dt, 1H), 7.00 (dd, 1H), 7.34 (m, 12H), 8.94 (dd, 1H).

EXAMPLE 29

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide, trifluoroacetate Step A:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(R)-benzyloxypropyl]amino-3-methylbutanamide, trifluoroacetate To a solution of 250 mg (0.399 mmol) of N-[1-[[2'-[(methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 2) in 12 mL of methanol was added 1.35 g of powdered 4 Å molecular sieves followed by 713 mg (4.34 mmol) of (R)-2-benzyloxypropanal (prepared from ethyl D-lactate according to the procedure of Hanessian and Kloss, *Tetrahedron Lett.*, 26, 1261–1264 (1985).) in 2 mL of dry methanol. After adjusting the pH of the suspension to 5.5 with glacial acetic acid, the reaction mixture was stirred at room temperature for 3 hours. Dropwise, 2.5 mL of 1.0M sodium cyanoborohydride in tetrahydrofuran was added and the reaction mixture stirred at room temperature for 18 hours. The reaction mixture was filtered and the filtrate treated with 2.0 mL of trifluoroacetic acid (CAUTION! evolution of hydrogen cyanide). After stirring for 10 minutes, all volatiles were removed under vacuum and the residue chromatographed on silica gel, eluting with methylene chloride/methanol/concentrated ammonium hydroxide (90:5:1) to yield 225 mg (0.339 mmol, 85%) of product. FAB-MS with Li: calculated for $C_{40}H_{47}N_5O_4$ 661: found 668 (M+Li), 662 (M+1). $^1$H NMR (400 MHz, CD$_3$OD): δ 1.19 (d, 3H), 1.19 (s, 3H), 1.21 (s, 3H), 2.05 (m, 1H), 2.3 (m, 1H), 2.4 (m, 2H), 2.20 (s, 3H), 2.3 (m, 2H), 3.64 (m, 1H), 4.40 (dd, 1H), 4.58 (s, 1H), 4.62 (d, 1H), 5.05 (d, 1H), 5.14 (d, 1H), 7.23 (m, 16H), 7.66 (d, 1H).

Step B:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(R)-hydroxypropy]amino-3-methylbutanamide, trifluoroacetate A solution of 225 mg (0.339 mmol) of the intermediate obtained in Step A in 5 mL of methanol containing 0.2 mL of trifluoroacetic acid was hydrogenated at ambient temperature and 40 psi for 24 hours over 500 mg of 30% palladium on carbon. The reaction mixture was filtered through Celite and the filtrate was evaporated under vacuum and the residue purified by reverse phase medium pressure liquid chromatography on C8, eluting with methanol/0.1% aqueous trifluoroacetic acid (65:35). Fractions containing the product were combined, solvents removed under vacuum and the residue lyophilized from water to give 160 mg (0.23 mmol, 69%) of the title compound as a white solid. FAB-MS: calculated for $C_{33}H_{41}N_5O_4$ 571: found 572 (M+H). $^1$H NMR (400 MHz, CDCl$_3$): δ 1.20 (d, 1H), 1.36 (s, 3H), 1.37 (s, 3H), 2.15 (m, 1H), 2.34 (m, 1H), 2.34 (m, 1H), 2.62 (dd, 2H), 2.63 (s, 3H), 2.68 (m, 2H), 2.80 (dd, 1H), 3.09 (dd, 1H), 3.90 (m, 1H), 4.40 (dd, 1H), 5.08 (d, 1H), 5.16 (d, 1H), 7.22 (m, 11H), 7.62 (d, 1H).

EXAMPLE 30

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide, trifluoroacetate Prepared from N-[1-[[2'-[(morpholinocarbonyl)-amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 6) and (R)-2-benzyloxypropanal by the procedure described in Example 29. FAB-MS: calculated for $C_{36}H_{45}N_5O_5$ 627: found 650 (M+Na). $^1$H NMR (400 MHz,CDCl$_3$): δ 1.20 (d,3H), 1.36 (s,3H), 1.39 (s,3H), 2.14 (m,1H), 2.34 (m,1H), 2.62 (dd,2H), 2.66 (m,2H, 2.7 (dd,1H), 3.09 (dd,1H), 3.25 (m,4H), 3.63 (m,4H), 3.83 (m,1H), 4.39 (m,1H), 5.05 (d,1H), 5.20 (d,1H), 7.29 (m,12H).

EXAMPLE 31

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(R)-hydroxypropyl]amino-3-methylbutanamide, trifluoroacetate Prepared from N-[1-[[2'-[[(2-hydroxyethylamino)-carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 8) and (R)-2-benzyloxypropanal by the procedure described in Example 29. FAB-MS: calculated for $C_{34}H_{43}N_5O_5$ 601: found 602 (M+H). $^1$H NMR (400 MHz,CD$_3$OD): δ 1.20 (d,3H), 1.36 (s,3H), 1.38 (s,3H), 2.18 (m,1H), 2.35 (m,1H), 2.62 (dd,2H), 2.68 (m,2H), 2.78 (dd,1H), 3.09 (dd,1H), 3.2 (t,2H), 3.52 (t,2H), 3.93 (m,1H), 4.40 (dd,1H), 5.12 (d,1H), 5.18 (d,1H), 7.28 (m,11H), 7.65 (d,1H).

EXAMPLE 32

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide, trifluoroacetate To a stirred solution of 368 mg (0.716 mmol) of N-[1-[[2'-[(methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 2) in 12 mL of dry methanol under nitrogen was added 1.35 g of powdered 4A molecular sieves followed by a solution of 0.4 g of D-glyceraldehyde acetonide (used crude as prepared according to the procedure of L. W. Hertel, C. S.

Grossman and J. S. Kroin, Synth. Comm., 21, 151–154 (1991).) in 1 mL of dry methanol. The pH of the mixture was carefully adjusted to 5.5 with glacial acetic acid and triethylamine. The reaction was stirred at room temperature for 2 hours at which time 3.0 mL of a 1.0 M solution of sodium cyanoborohydride in tetrahydrofuran was added dropwise by syringe. The reaction mixture was stirred at room temperature for 18 hours, then filtered and the filtrate treated with 9 mL of trifluoroacetic acid and 9 mL of water. After 1 hour, the reaction mixture was evaporated under vacuum and the residue purified by reverse phase medium pressure liquid chromatography on C8, eluting with methanol/0.1% aqueous trifluoroacetic acid (60:40). Fractions containing the product were combined, solvents removed under vacuum and the residue lyophilized from water to give 167 mg of the title compound as a white solid. FAB-MS: calculated for $C_{33}H_{41}N_5O_5$ 587: found 589. $^1$H NMR (400 MHz, $CD_3OD$): δ 1.37 (s,3H), 1.39 (s,3H), 2.15 (m,1H), 2.35 (m,1H), 2.55–2.75 (m,4H), 2.64 (s,3H), 2.95 (dd,1H), 3.18 (dd,1H), 3.54 (m,2H), 3.83 (m,1H), 4.42 (dd,1H), 5.08 (d,1H), 5.16 (d,1H), 7.1–7.4 (m,11H), 7.61 (d,1H).

EXAMPLE 33

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide, trifluoroacetate The title compound was prepared from N-[1-[[2'-[(aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 5) and D-glyceraldehyde acetamide according to the procedure described in Example 32. FAB-MS: calculated for $C_{32}H_{41}N_5O_4$ 559: found 561. $^1$H NMR (400 MHz, $CD_3OD$): δ 1.36 (s, 1H), 1.38 (s, 3H), 2.15 (m, 1H), 2.34 (m, 1H), 2.62 (dd, 2H), 2.68 (m, 2H), 2.95 (dd, 1H), 3.18 (dd, 1H), 3.52 (m, 2H), 3.82 (m, 1H), 4.40 (dd, 1H), 5.05 (d, 1H), 5.06 (d, 1H), 7.25 (m, 11H), 7.60 (d, 1H).

EXAMPLE 34

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide, trifluoroacetate The title compound was prepared from N-[1-[[2'-[[(2-hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 8) and D-glyceraldehyde acetonide according to the procedure described in Example 32.

EXAMPLE 35

2-Amino-2-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]propanamide, hydrochloride Step A:
2-Benzyloxycarbonylamino-2-methyl-N-[2,3,4,5-tetrahydro-2-oxo-1H-benzazepin-3(R)-yl]propanamide Prepared from N-carbobenzyloxy-2-methylalanine and 3(R)-amino-2,3,4,5-tetrahydro-1H-benzazepin-2-one (Example 1, Step E) substituting benzotriazol-1-yloxytripyrrolidinophosphonium hexafluorophosphate for benzotriazol-1-yloxytris(dimethylamino)-phosphonium hexafluorophosphate according to the procedure described in Example 1, Step I. $^1$H NMR (200 MHz, $CDCl_3$): δ 1.47 (s, 3H), 1.52 (s, 3H), 1.82 (m, 1H), 2.50–3.00 (m, 3H), 4.45 (m, 1H), 5.05 (s, 2H), 5.37 (s, 1H), 6.80–7.40 (m, 10H), 8.65 (s, 1H). FAB-MS: calculated for $C_{22}H_{25}N_3O_4$ 395; found 396 (M+H,100%).

Step B:
4-Bromobenzyl-t-butyldiphenylsilyl ether

To a solution of 28.2 g (0.150 mol) of 4-bromobenzylalcohol in 470 mL of dry dimethylformamide under nitrogen atmosphere was added 31.4 mL (0.225 mol) of triethylamine. The reaction mixture was cooled to 0° C. and 43 mL (0.17 mol) of t-butyl-chlorodiphenylsilane was added dropwise by addition funnel. The reaction mixture was stirred at ambient temperature overnight then poured into a separatory funnel containing 1 L of diethyl ether and 500 mL of water. To this mixture was added 125 mL of 2N aqueous hydrochloric acid. The layers were separated and the aqueous layer was extracted with diethyl ether (2×350 mL). The organic extracts were combined, washed with water (2×250 mL) and dried over magnesium sulfate. The solids were removed by filtration and the solvent removed under vacuum to give an oil which crystallized on standing. The flask containing the crude product was placed in the freezer overnight then triturated with a minimal amount of methanol and filtered. The solid was air dried for several hours then dried under vaccuum overnight to afford 59.5 g (93%) of product as an off-white solid (mp 44–47° C.). $^1$H NMR (200 MHz, $CDCl_3$): δ 1.15 (s, 9H), 4.76 (s, 2H), 7.25 (d, 8 Hz, 2H), 7.45 (m, 8H), 7.75 (m, 4H). FAB-MS: calculated for $C_{23}H_{25}BrOSi$ 424; found 425 (M+H, 7%).

Step C:
4-(t-Butyldiphenylsiloxymethyl)phenylboronic acid

To a solution of 20 g (47 mmol) of 4-bromobenzyl-t-butyldiphenyl silyl ether (Step B) in 200 mL of dry tetrahydrofuran under a nitrogen atmosphere at –78° C. was added dropwise by syringe 19.74 mL (49.35 mmol) of a 2.5M solution of n-butyl lithium in hexanes over twenty minutes. The resulting mixture was stirred for thirty minutes, then 11.6 mL (50.3 mmol) of triisopropyl borate was added by syringe. The reaction mixture was stirred at –78° C. for thirty minutes then slowly warmed to room temperature and stirred for an additional two hours. The reaction mixture was then quenched by the addition of 750 mL of water containing 100 mL of concentrated hydrochloric acid and 500 mL of diethyl ether. The mixture was stirred for one hour and then the organic layer was separated. The aqueous layer was extracted with diethyl ether (2×400 mL). The combined ether extracts were washed with saturated aqueous sodium chloride (4×100 mL), dried over magnesium sulfate and filtered. The solvent was removed under vacuum to give an oil which was crystallized by dissolving in hexanes and evaporation of the solvent under vacuum to afford 15.6 g (85%) of product as a white solid (mp 171–174° C.). $^1$H NMR (200 MHz, $CDCl_3$): δ 1.11 (s, 9H), 4.86 (s, 2H), 7.40 (m, 6H), 7.58 (d, 8 Hz, 2H), 7.70 (m, 4H), 8.22 (d, 8 Hz, 2H). FAB-MS: calculated for $C_{23}H_{27}BrO_3Si$ 390; found 372 (M–$H_2O$).

Step D:
N-(t-Butoxycarbonyl)-2-bromobenzylamine

To a slurry of 8.88 g (39.9 mmol) of 2-bromobenzylamine hydrochloride in 100 mL of dry methylene chloride under a nitrogen atmosphere was added by syringe 12.24 mL (87.80 mmol) of triethylamine. The resulting solution was stirred at 0° C. for five minutes then treated with 9.6 g (44 mmol) of di-t-butyldicarbonate. The reaction was stirred at room temperature for two hours then diluted with 350 mL of methylene chloride. The solution was washed with water (2×150 mL), saturated aqueous ammonium chloride (150 mL), saturated aqueous sodium bicarbonate (4×150 mL) and saturated aqueous sodium chloride (150 mL), dried over sodium sulfate and filtered. The solvent was removed under vacuum to give an oil which was crystallized by dissolving in hot hexanes, filtering and cooling the solution. The product was filtered and dried under vacuum to afford 8.66 g (90%) of the product as a white solid (mp 51–53° C.). $^1$H NMR (200 MHz, CDCl$_3$): δ 1.41 (s, 9H), 4.37 (d, 5 Hz, 2H), 5.00 (s, 1H), 7.10 (m, 1H), 7.25 (m, 1H), 7.35 (m, 1H), 7.40 (d, 6 Hz, 1H). FAB-MS: calculated for C$_{12}$H$_{16}$BrNO$_2$ 285; found 286 (M+H).

Step E:

2'-[(t-Butoxycarbonylamino)methyl]-4-[(t-butyldiphenylsiloxy)methyl]-1,1'-biphenyl To a solution of 3.2 g (8.2 mmol) of 4-(t-butyldiphenylsilyoxymethyl)phenylboronic acid (Step C) in 64 mL of benzene was added 2.2 mL of water, 6.4 mL of 5N aqueous sodium hydroxide, and 8.3 mL of isopropanol. To this mixture was added 180 mg (0.16 mmol) of tetrakis(triphenylphosphine) palladium and 2.20 g (7.81 mmol) of N-(t-butoxycarbonyl)-2-bromobenzylamine (Step D). The resulting mixture was heated under nitrogen at reflux for 2 hours then cooled to room temperature. The reaction mixture was diluted with 100 mL of water, transferred to a separatory funnel and extracted with ether (3×150 mL). The combined ether extracts were washed with saturated aqueous sodium bicarbonate (100 mL) and saturated aqueous sodium chloride (100 mL), dried over magnesium sulfate and filtered. The solvent was removed under vacuum to give a crude product which was purified by column chromatography on silica gel eluting with hexanes/ethyl acetate (9:1) to afford 4.31 g (100%) of the product as a clear oil. $^1$H NMR (200 MHz, CDCl$_3$): δ 1.11 (s, 9H), 1.41 (s, 9H), 4.27 (d, 6 Hz, 2H), 4.45 (m, 1H), 4.81 (s, 2H), 7.20–7.49 (m, 14H), 8.72 (m, 4H). FAB-MS: calculated for C$_{35}$H$_{41}$NO$_3$Si 551; found 552 (M+H).

Step F:

2'-[(t-Butoxycarbonylamino)methyl]-1,1'-biphenyl-4-methanol

To a solution of 3.85 g (7.00 mmol) of 2'-[(t-butoxycarbonylamino)methyl]-4-[(t-butyldiphenylsiloxy)methyl]-1,1'-biphenyl (Step E) in 25 mL of dry tetrahydrofuran under a nitrogen atmosphere was added by syringe 10.5 mL (0.530 mmol) of a 1.0M solution of tetra-n-butylammonium fluoride in tetrahydrofuran. The reaction mixture was stirred for two hours then diluted with 700 mL of diethyl ether. The mixture was washed with water (3×150 mL), saturated aqueous sodium bicarbonate (50 mL), saturated aqueous sodium chloride (50 mL), then dried over magnesium sulfate and filtered. The solvent was removed under vacuum to give an oil which was purified by column chromatography on silica gel eluting with hexanes/ethyl acetate (55:45) to afford 2.02 g (92%) of the product as a white solid (mp 89–93° C.). $^1$H NMR (200 MHz, CDCl$_3$): δ 1.40 (s, 9H), 2.50 (s, 2H), 4.20 (s, 2H), 4.70 (s, 2H), 7.18–7.45 (m, 8H). FAB-MS: calculated for C$_{19}$H$_{23}$NO$_3$ 313; found 314 (M+H).

Step G:

2'-[(t-Butoxycarbonylamino)methyl]-1,1'-biphenyl-4-methanol, methanesulfonate ester To solution of 53 mg (0.17 mmol) of 2'-[(t-butoxycarbonylamino)methyl]-1,1'-biphenyl-4-methanol (Step E) in 1 mL of dry methylene chloride under nitrogen atmosphere at 0° C. was added by syringe 0.035 mL (0.25 mmol) of triethylamine followed by 0.016 mL (0.20 mmol) of methanesulfonyl chloride. The reaction mixture was stirred for 2 hours at 0° C. then diluted with 75 mL of methylene chloride, washed with water, saturated aqueous sodium bicarbonate, saturated aqueous sodium chloride, dried over sodium sulfate and filtered. The solvent was removed under vacuum to give 61 mg (97%) of the product as a white solid which was used in the next step without further purification. $^1$H NMR (200 MHz, CDCl$_3$): δ 1.38 (s, 9H), 2.95 (s, 3H), 4.20 (d, 5 Hz, 2H), 4.65 (s, 1H), 5.25 (s, 2H), 7.18–7.50 (m, 8H). FAB-MS: calculated for C$_{20}$H$_{25}$NO$_5$S 391; found 392 (M+H).

Step H:

2-Benzyloxycarbonylamino-2-methyl-N-[2,3,4,5-tetrahydro-2-oxo-1-[[2'-[(t-butoxycarbonylamino)methyl]-[1,1'-biphenyl]-4-yl]methyl]-1H-benzazepin-3(R)-yl]-propanamide To a solution of 819 mg (2.07 mmol) of 2-benzyloxycarbonylamino-2-methyl-N-[2,3,4,5-tetrahydro-2-oxo-1H-benzazepin-3(R)-yl]propanamide (Step A) in 7.0 mL of dry dimethylformamide under nitrogen at 0° C. was added 83 mg (2.1 mmol) of 60% sodium hydride/oil dispersion. After stirring for 15 minutes, a solution of 810 mg (2.1 mmol) of 2'-[(t-butoxycarbonylamino)methyl]-1,1'-biphenyl-4-methanol, methanesulfonate ester (Step F) in 2.0 mL of dimethylformamide was added by cannula. The flask which originally contained the methanesulfonate ester was rinsed with 1.0 mL of dimethylformamide which was added to the reaction mixture. After stirring at 0° C. for 15 minutes, the reaction mixture was diluted with 400 mL of ethyl acetate and 50% saturated ammonium chloride. The mixture was transferred to a separatory funnel and the aqueous layer was separated. The organic layer was washed with 100 mL of saturated aqueous sodium bicarbonate and saturated aqueous sodium chloride. The organic layer was dried over magnesium sulfate, filtered and the solvent removed under vacuum. The residue was purified by flash chromatography on silica gel eluting with ethyl acetate/hexane (55:45) to afford 1.2 g (84%) of the product as a white foam. $^1$H NMR (200 MHz, CDCl$_3$): δ 1.38 (s, 9H), 1.48 (s, 3H), 1.52 (s, 3H), 1.78 (s, 1H), 2.35–2.70 (m, 3H), 4.18 (d, 6 Hz, 2H), 4.38–4.62 (m, 2H), 4.82 (d, 16 Hz, 1H), 5.05 (s, 2H), 5.25 (d, 16 Hz, 1H), 5.32 (s, 1H), 7.08 (d, 6 Hz, 1H), 7.12–7.43 (m, 18H). FAB-MS: calculated for C$_{41}$H$_{46}$N$_4$O$_6$ 690; found 691(M+H).

Step I:

2-Benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl]propanamide, hydrochloride To a solution of 9.83 g (0.55 mmol) of 2-benzyloxycarbonylamino-2-methyl-N-[2,3,4,5-tetrahydro-2-oxo-1-[[2'-[(t-butoxycarbonylamino)methyl][1,1'-biphenyl]-4-yl]methyl]-1H-benzazepin-3(R)-yl]propanamide (Step H) in 170 mL of methanol was added 120 mL of 9N aqueous hydrochloric acid. Periodically 10 mL portions of methanol were added to the reaction mixture to dissolve precipitates which form during the reaction (50 mL total). The reaction mixture was stirred overnight at room temperature then the solvent was removed under vacuum. The resulting oil was dissolved in methanol and the solvent was removed under vacuum to afford 8.57 g (96%) of the title compound as an off-white foam. $^1$H NMR (200 MHz, CD$_3$OD): δ 1.40 (s, 6H), 1.90 (m, 1H), 2.20–2.65 (m, 3H), 4.02 (s, 2H), 4.32 (m, 1H), 4.96 (d, 16 Hz, 1H), 5.00 (s, 2H), 5.25(d, 16 Hz, 1H), 7.08–7.65 (m, 17H). FAB-MS: calculated for C$_{36}$H$_{38}$N$_4$O$_4$ 590; found 591(M+H, 100%).

Step J:

2-Benzyloxycarbonylamino-2-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]-propanamide To a solution of 8.57 g (13.7 mmol) of 2-benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl]-propanamide, hydrochloride (Step I) in 75 mL of dry methylene chloride under nitrogen atmosphere was added 2.28 mL (16.4 mmol) of triethylamine followed by 0.89 mL (15 mmol) of methyl isocyanate. After stirring at room temperature for 45 minutes the solvent was removed under vacuum. The resulting material was dissolved in methylene chloride and purified by flash column chromatography on silica gel eluting with ethyl acetate/methanol (96:4) to afford 7.73 g (87%) of product as a white foam. $^1$H NMR (200 MHz, CD$_3$OD): δ 1.39 (s, 6H), 1.82 (m, 1H), 2.15–2.60 (m, 3H), 2.63 (s, 3H), 4.13 (s, 2H), 4.36 (m, 1H), 4.86 (d, 15 Hz, 1H), 4.85 (s, 2H), 5.32 (d, 15 Hz, 1H), 7.08–7.43 (m, 17H). FAB-MS: calculated for C$_{38}$H$_{41}$N$_5$O$_5$ 647; found 648(M+H, 80%).

Step K:

2-Amino-2-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]propanamide, hydrochloride To a solution of 5.00 g (7.72 mmol) of 2-benzyloxycarbonylamino-2-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]propanamide (Step J) in 100 mL of dry methanol was added 0.50 g (0.1 equiv. by weight) of palladium hydroxide. The mixture was stirred under hydrogen atmosphere for 2 hours. The mixture was filtered through Celite. The filter pad was washed with 50 mL of methanol. The filtrate was combined and the solvent was removed under vacuum. The resulting oil was dissolved in 50 mL of methanol and treated with 17 mL (8.5 mmol) of a 0.499N aqueous hydrochloric acid solution. The solvent was removed under vacuum to give a solid which was crystallized by refluxing in 480 mL of acetonitrile/ethanol (7:1). The mixture was cooled to room temperature with gentle stirring. After 3 hours the solids were filtered and washed with 80 mL of ice cold acetonitrile/ethanol (7:1) and then air dried for 3 hours. The resulting solid was dissolved in 40 mL of water, filtered and lyophilized overnight to afford 3.78 g (89%) of the title compound as a white solid. $^1$H NMR (400 MHz, CD$_3$OD): δ 1.55 (s, 3H), 1.64 (s, 3H), 2.28 (m, 2H), 2.62 (m, 2H), 2.67 (s, 3H), 4.16 (dd; 16, 14 Hz; 2H), 4.39 (dd; 12, 8 Hz; 1H), 5.00 (d, 15 Hz, 1H), 5.22 (d, 15 Hz, 1H), 7.14 (d, 7 Hz, 1H), 7.20–7.41 (m, 11H). FAB-MS: calculated for C$_{30}$H$_{35}$N$_5$O$_3$ 513; found 514 (M+H, 100%).

EXAMPLE 36

2-Amino-2-methyl-N-[2,3,4,5-tetrahydro-1-[[2'-[[[((2-hydroxyethyl)amino)carbonyl]amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl]propanamide, trifluoroacetate To a solution of 380 mg (0.55 mmol) of 2-benzyloxycarbonylamino-2-methyl-N-[2,3,4,5-tetrahydro-2-oxo-1-[[2'-[(t-butoxycarbonylamino)methyl][1,1'-biphenyl]-4-yl]methyl]-1H-benzazepin-3(R)-yl] propanamide (Example 35, Step H) in 2 mL of dry methylene chloride was added 5 drops of anisole followed by 2 mL of trifluoroacetic acid. The reaction mixture was stirred for 1.5 hours at room temperature at which time the solvent was removed under vacuum. The resulting oil was dissolved in 5 mL of carbon tetrachloride and the solvent was removed under vacuum. The process was repeated with 5 mL of chloroform followed by 5 mL of methylene chloride to give 427 mg (>100%) of the product containing minor amount of anisole) as an off-white foam. $^1$H NMR (200 MHz, CDCl$_3$): δ 1.45 (s, 6H), 1.90 (m, 1H), 2.25–2.65 (m, 3H), 4.12 (s, 2H), 4.38 (m, 1H), 4.85 (d, 16 Hz, 1H), 4.96 (s, 2H), 5.05 (d, 16 Hz, 1H), 5.55 (s, 1H), 6.91 (m, 1H), 7.05–7.60 (m, 19H). FAB-MS: calculated for C$_{36}$H$_{38}$N$_4$O$_4$ 590; found 591(M+H, 100%).

Step B:

2-Benzyloxycarbonylamino-2-methyl-N-[2,3,4,5-tetrahydro-1-[[2'-[[[((2-hydroxyethyl)amino)carbonyl]amino]-methyl][1,1'-biphenyl]-4-yl]methyl]-2-oxo-1H-benzazepin-3(R)-yl]propanamide To a solution of 160 mg (0.23 mmol) of 2-benzyloxycarbonylamino-2-methyl-N-[2,3,4,5-tetrahydro-2-oxo-1-[[2'-(aminomethyl)[1,1'-biphenyl]4-yl]methyl]-1H-benzazepin-3(R)-yl]-propanamide, trifluoroacetate (Step A) in 1 mL of dry methylene chloride under nitrogen atmosphere was added 0.063 mL (0.45 mmol) of triethylamine followed by 0.039 mL (0.25 mmol) of 2-isocyanatoethyl methacrylate. The reaction mixture was stirred at room temperature for 30 minutes then the solvent was removed under vacuum.

The residue was dissolved in 2 mL of tetrahydrofuran/water (3:1) and to the resulting solution was added 42 mg (1.0 mmol) of lithium hydroxide monohydrate. After stirring at room temperature for 3 hours the reaction mixture was diluted with 100 mL of ethyl acetate and washed with 50 mL of brine. The organic layer was dried over magnesium sulfate, filtered and the solvent removed under vacuum to afford 149 mg (97%) of the product as a white foam. $^1$H NMR (200 MHz, CDCl$_3$): δ 1.48 (m, 9H), 1.82 (m, 1H), 2.10–2.70 (m, 3H), 3.05 (m, 2H), 3.15 (t, 4 Hz, 2H), 2.55 (t, 4 Hz, 2H), 4.20 (s, 2H), 4.45 (m, 1H), 4.68 (s, 1H), 5.03 (s, 2H), 5.38 (s, 1H), 7.05–7.43 (m, 19H). FAB-MS: calculated for C$_{39}$H$_{43}$N$_5$O$_6$ 677; found 678(M+H, 60%).

Step C:

2-Amino-2-methyl-N-[2,3,4,5-tetrahydro-1-[[2'-[[[((2-hydroxyethyl)amino)carbonyl]amino]methyl][1,1'-biphenyl]-4-yl]methyl]-2-oxo-1H-benzazepin-3(R)-yl]-propanamide, trifluoroacetate To a solution of 149 mg (0.22 mmol) of 2-benzyloxycarbonylamino-2-methyl-N-[2,3,4,5-tetrahydro-1-[[2'-[[[((2-hydroxyethyl)amino)carbonyl]amino]methyl][1,1'-biphenyl]-4-yl]methyl]-2-oxo-1H-benzazepin-3(R)-yl]propanamide (Step B) in 3 mL of dry methanol was added 30 mg (0.2 equiv. by weight) of palladium hydroxide. The mixture was stirred under hydrogen atmosphere for 2 hours. The mixture was filtered through Celite. To the filtrate was added 3 drops of trifluoroacetic acid and the solvent was removed under vacuum to give a solid which was purified by reverse phase medium pressure liquid chromatography on C-8 eluting with methanol/0.1% aqueous trifluoroacetic acid (60:40) to afford 87 mg (60%) of the title compound as a white solid. $^1$H NMR (200 MHz, CD$_3$OD): δ 1.53 (s, 3H), 1.62 (s, 3H), 2.28 (m, 2H), 2.60 (m, 2H), 3.19 (t, 6 Hz, 2H), 3.53 (t, 6 Hz, 2H), 4.15 (s, 2H), 4.39 (dd, 12, 8 Hz; 1H), 4.99 (d, 15 Hz, 1H), 5.20 (d, 15 Hz, 1H), 7.10–7.41 (m, 12R). FAB-MS: calculated for C$_{31}$H$_{37}$N$_5$O$_4$ 543; found 544(M+H, 80%).

EXAMPLE 37

2-Amino-2-methyl-N-[2,3,4,5-tetrahydro-1-[[2'-[[[((2-methoxyphenyl)amino)carbonyl]amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[[((2-methoxyphenyl)amino)carbonyl]amino]methyl][1,1'-biphenyl]-4-yl]methyl]-2-oxo-1H-benzazepin-3(R)-yl]propanamide To a solution of 100 mg (0.142 mmol) of 2-benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl]-propanamide, trifluoroacetate (Example 36, Step A) in 2 mL of dry methylene chloride under nitrogen atmosphere was added 0.040 mL (0.28 mmol) of triethylamine followed by 0.021 mL (0.16 mmol) of 2-methoxyphenyl isocyanate. The reaction mixture was stirred at room temperature for 30 minutes, diluted with 100 mL of ethyl acetate, washed with 25 mL of saturated aqueous ammonium chloride, 25 mL of saturated aqueous sodium bicarbonate and 25 mL of brine. The organic layer was dried over magnesium sulfate, filtered and the solvent removed under vacuum to afford 102 mg (97%) of the product as a white foam. $^1$H NMR (200 MHz, CD$_3$OD): δ 1.38 (s, 6H), 1.80 (m, 1H), 2.15–2.50 (m, 3H), 3.80 (s, 3H), 4.19 (s, 2H), 4.27 (m, 1H), 4.68 (d, 16 Hz, 1H), 5.00 (s, 2H), 5.30 (d, 16 Hz, 1H), 6.90 (m, 3H), 7.10–7.45 (m, 17H), 7.92 (m, 1H). FAB-MS: calculated for C$_{44}$H$_{45}$N$_5$O$_6$ 739; found 740 (M+H, 60%).

Step B:

2-Amino-2-methyl-N-[2,3,4,5-tetrahydro-1-[[2'-[[[((2-methoxyphenyl)amino)carbonyl]amino]methyl][1,1'-biphenyl]-4-yl]methyl]-2-oxo-1H-benzazepin-3(R)-yl]-propanamide, trifluoroacetate The title compound was prepared from 2-benzyloxycarbonylamino-2-methyl-N-[2,3,4,5-tetrahydro-1-[[2'-[[[((2-methoxyphenyl)amino)carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 1.52 (s, 3H), 1.61 (s, 3H), 2.22 (m, 2H), 2.65 (m, 2H), 3.82 (s, 3H), 4.21 (s, 2H), 4.36 (dd; 12, 8 Hz; 1H), 4.93 (d, 15 Hz, 1H), 5.20 (d, 15 Hz, 1H), 6.78–6.95 (m, 3H), 7.12–7.45 (m, 12H) 7.91 (dd, 4, 1 Hz; 1H). FAB-MS: calculated for C$_{36}$H$_{39}$N$_5$O$_4$ 605; found 606(M+H, 100%).

EXAMPLE 38

2-Amino-2-methyl-N-[2,3,4,5-tetrahydro-1-[[2'-[[[((2-hydroxyphenyl)amino)carbonyl]amino]methyl][1,1'-biphenyl]-4-yl]methyl]-2-oxo-1H-benzazepin-3(R)-yl]propanamide, trifluoroacetate Step A:

2-Amino-2-methyl-N-[2,3,4,5-tetrahydro-1-[[2'-[[[((2-hydroxyphenyl)amino)carbonyl]amino]methyl][1,1'-biphenyl]-4-yl]methyl]-2-oxo-1H-benzazepin-3(R)-yl]-propanamide, trifluoroacetate To a solution of 48 mg (0.067 mmol) of 2-amino-2-methyl-N-[2,3,4,5-tetrahydro-1-[[2'-[[[((2-methoxyphenyl)amino)carbonyl]-amino]methyl][1,1'-biphenyl]-4-yl]methyl]-2-oxo-1H-benzazepin-3(R)-yl]propanamide, trifluoroacetate (Example 37, Step B) in 2 mL of dry methylene chloride under nitrogen atmosphere was added 0.33 mL (0.33 mmol) of a 1.0M solution of boron tribromide in methylene chloride. The reaction mixture was stirred at room temperature for one hour and then quenched by the addition of 1 mL of water. The solvent was removed under vacuum and the residue was dissolved in 2 mL of methanol and treated with 2 drops of trifluoroacetic acid. The solvent was removed under vacuum and the residue was purified by reverse phase medium pressure liquid chromatography on C-8, eluting with methanol/0.1% aqueous trifluoroacetic acid (60:40), to afford 37 mg (60%) of the title compound as a white solid. $^1$H NMR (200 MHz, CD$_3$OD): δ 1.52 (s, 3H), 1.61 (s, 3H), 2.22 (m, 2H), 2.58 (m, 2H), 4.22 (s, 2H), 4.36 (dd; 12, 8 Hz; 1H), 4.93 (d, 15 Hz, 1H), 5.20 (d, 15 Hz, 1H), 6.67–6.85 (m, 3H), 7.12–7.48 (m, 12H) 7.62 (m, 1H). FAB-MS: calculated for C$_{35}$H$_{37}$N$_5$O$_4$ 591; found 592 (M+H, 60%).

EXAMPLE 39

2-Amino-2-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]-propanamide Prepared from 2-benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl]propanamide, trifluoroacetate (Example 36, Step A) and trimeffłylsilyl isocyanate according to the procedure described in Example 37, Step A. $^1$H NMR (200 MHz, CD$_3$OD): δ 1.40 (s, 6H), 1.82 (m, 1H), 2.15–2.60 (m, 3H), 4.12 (s, 2H), 4.32 (m, 1H), 4.85 (d, 15 Hz, 1H), 5.00 (s, 2H), 5.32 (d, 15 Hz, 1H), 7.05–7.43 (m, 17H). FAB-MS: calculated for C$_{37}$H$_{39}$N$_5$O$_5$ 633; found 644(M+H, 100%).

Step B:

2-Amino-2-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[(aminocarbonyl)amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 1.53 (s, 3H), 1.62 (s, 3H), 2.25 (m, 2H), 2.58 (m, 2H), 4.13 (s, 2H), 4.37 (dd, 12, 8 Hz; 1H), 4.97 (d, 15 Hz, 1H), 5.20 (d, 15 Hz,1H), 7.10–7.41 (m, 12H). FAB-MS: calculated for C$_{29}$H$_{33}$N$_5$O$_3$ 499; found 500 (M+H, 100%).

EXAMPLE 40

2-Amino-2-methyl-N-[2,3,4,5-tetrahydro-1-[[2'-[[[(benzylamino)carbonyl]amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[[(benzylamino)carbonyl]amino]methyl][1,1'-biphenyl]-4-yl]methyl]-2-oxo-1H-benzazepin-3(R)-yl]propanamide Prepared from 2-benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl]propanamide, trifluoroacetate (Example 36, Step A) and benzyl isocyanate according to the procedure described in Example 37, Step A. $^1$H NMR (200 MHz, CD$_3$OD): δ 1.38

(s, 6H), 1.82 (m, 1H), 2.15–2.55 (m, 3H), 4.14 (s, 2H), 4.24 (s, 2H), 4.32 (m, 1H), 4.85 (d, 15 Hz, 1H), 5.00 (s, 2H), 5.32 (d, 15 Hz, 1H), 7.05–7.42 (m, 22H). FAB-MS: calculated for $C_{44}H_{45}N_5O_5$ 723; found 724 (M+H, 100%).

Step B:

2-Amino-2-methyl-N-[2,3,4,5-tetrahydro-1-[[2'-[[[(benzylamino)carbonyl]amino]methyl][1,1'-biphenyl]-4-yl]methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[[(benzylamino)carbonyl]amino]methyl][1,1'-biphenyl])4-yl]methyl]-2-oxo-1H-benzazepin-3(R)-yl]propanamide (Step A) according to the procedure described in Example 36, Step C. $^1$H NMR (200 MHz, $CD_3OD$): δ 1.53 (s, 3H), 1.62 (s, 3H), 2.25 (m, 2H), 2.58 (m, 2H), 4.17 (s, 2H), 4.26 (s, 2H), 4.37 (dd, 11, 8 Hz; 1H), 4.96 (d, 15 Hz, 1H), 5.20 (d, 15 Hz, 1H), 7.10–7.41 (m, 17H). FAB-MS: calculated for $C_{36}H_{39}N_5O_3$ 589; found 590 (M+H, 80%).

EXAMPLE 41

2-Amino-2-methyl-N-[2,3,4,5-tetrahydro-1-[[2'-[[[(1-propylamino)carbonyl]amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[[(1-propylamino)carbonyl]amino]methyl]-[1,1'-biphenyl]-4-yl]methyl]-2-oxo-1H-benzazepin-3(R)-yl]propanamide Prepared from 2-benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl]propanamide, trifluoroacetate (Example 36, Step A) and 1-propyl isocyanate according to the procedure described in Example 37, Step A. $^1$H NMR (200 MHz, $CD_3OD$): δ 0.86 (t, 7.5 Hz, 3H), 1.39 (s, 6H), 1.42 (m, 2H), 1.82 (m, 1H), 2.19–2.55 (m, 3H), 3.01 (t, 7 Hz, 2H), 4.12 (s, 2H), 4.32 (m, 1H), 4.85 (d, 15 Hz, 1H), 5.00 (s, 2H), 5.31 (d, 15 Hz, 1H), 7.08–7.40 (m, 17H), 7.63 (d, 8 Hz, 1H). FAB-MS: calculated for $C_{40}H_{45}N_5O_5$ 675; found 676 (M+H, 85%).

Step B:

2-Amino-2-methyl-N-[2,3,4,5-tetrahydro-1-[[2'-[[[(1-propylamino)carbonyl]amino]methyl][1,1'-biphenyl]-4-yl]-methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[[(1-propylamino)carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, $CD_3OD$): δ 0.87 (t, 7 Hz, 3H), 1.44 (dd; 16, 8 Hz; 2H), 1.53 (s, 3H), 1.62 (s, 3H), 2.25 (m, 2H), 2.58 (m, 2H), 3.08 (t, 7 Hz, 2H), 4.14 (s, 2H), 4.37 (dd; 12, 9 Hz; 1H), 4.97 (d, 15 Hz, 1H), 5.20 (d, 15 Hz, 1H), 7.10–7.41 (m, 12H). FAB-MS: calculated for $C_{32}H_{39}N_5O_3$ 541; found 542 (M+H, 100%).

EXAMPLE 42

2-Amino-2-methyl-N-[2,3,4,5-tetrahydro-1-[[2'-[[[[(1-methylethyl)amino]carbonyl]-amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[[[(1-methylethyl)amino]carbonyl]amino]methyl][1,1'-biphenyl]-4-yl]methyl]-2-oxo-1H-benzazepin-3(R)-yl]propanamide Prepared from 2-benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl]propanamide, trifluoroacetate (Example 36, Step A) and isopropyl isocyanate according to the procedure described in Example 37, Step A. $^1$H NMR (200 MHz, $CD_3OD$): δ 1.06 (d, 6.5 Hz, 6H), 1.39 (s, 6H), 1.82 (m, 1H), 2.19–2.58 (m, 3H), 3.74 (m, 1H), 4.12 (s, 2H), 4.32 (m, 1H), 4.87 (d, 15 Hz, 1H), 5.01 (s, 2H), 5.31 (d, 15 Hz, 1H), 7.08–7.40 (m, 17H). FAB-MS: calculated for $C_{40}H_{45}N_5O_5$ 675; found 676(M+H, 80%).

Step B:

2-Amino-2-methyl-N-[2,3,4,5-tetrahydro-1-[[2'-[[[[(1-methylethyl)amino]carbonyl]amino]methyl][1,1'-biphenyl]yl]methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[[[(1-methylethyl)amino]carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, $CD_3OD$): δ 1.06 (d, 6.5 Hz, 6H), 1.53 (s, 3H), 1.62 (s, 3H), 2.25 (m, 2H), 2.58 (m, 2H), 3.74 (m, 1H), 4.14 (s, 2H), 4.37 (dd, 12, 8 Hz; 1H), 4.97 (d, 15 Hz, 1H), 5.20 (d, 15 Hz, 1H), 7.10–7.41 (m, 12H). FAB-MS: calculated for $C_{32}H_{39}N_5O_3$ 541; found 542 (M+H, 100%).

EXAMPLE 43

2-Amino-2-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[[(ethylamino)carbonyl]amino]methyl][1,1'-biphenyl]-4-yl]methyl]-2-oxo-1H-benzazepin-3(R)-yl]-propanamide Prepared from 2-benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl]propanamide, trifluoroacetate (Example 36, Step A) and ethyl isocyanate according to the procedure described in Example 37, Step A. $^1$H NMR (200 MHz, $CD_3OD$): δ 1.03 (t, 7 Hz, 3H), 1.39 (s, 6H), 1.82 (m, 1H), 2.18–2.58 (m, 3H), 3.07 (q, 2H), 4.12 (s, 2H), 4.32 (m, 1H), 4.87 (d, 15 Hz, 1H), 5.00 (s, 2H), 5.31 (d, 15 Hz, 1H), 7.08–7.40 (m, 17H). FAB-MS: calculated for $C_{39}H_{43}N_5O_5$ 661; found 662 (M+H, 100%).

Step B:

2-Amino-2-methyl-N-[2,3,4,5-tetrahydro-1-[[2'-[[[(1-ethylamino)carbonyl]amino]methyl][1,1'-biphenyl]-4-yl] methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[[(1-ethylamino)carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, $CD_3OD$): δ 1.05 (t, 7 Hz, 3H), 1.53 (s, 3H), 1.62 (s, 3H), 2.25 (m, 2H), 2.58 (m, 2H), 3.09 (q, 2H), 4.14 (s, 2H), 4.37 (dd, 11, 8 Hz; 1H), 4.97 (d, 15 Hz, 1H), 5.20 (d, 15 Hz, 1H), 7.10–7.41 (m, 12H). FAB-MS: calculated for $C_{31}H_{37}N_5O_3$ 527; found 528 (M+H, 100%).

EXAMPLE 44

2-Amino-2-methyl-N-[2,3,4,5-tetrahydro-1-[[2'-[[[(N,N-dimethylamino)carbonyl]amino]methyl][1,1'-biphenyl]-4-yl]methyl]-2-oxo-1H-benzazepin-3(R)-yl]propanamide, trifluoroacetate Step A:
2-Benzyloxycarbonylamino-2-methyl-N-[2,3,4,5-tetrahydro-1-[[2'-[[[(N,N-dimethylamino)carbonyl]amino]methyl][1,1'-biphenyl]-4-yl]methyl]-2-oxo-1H-benzazepin-3(R)-yl]propanamide Prepared from 2-benzyloxycarbonylamino-2-methyl-N-[2,3,4,5-tetrahydro-2-oxo-1-[[2'-(aminomethyl)[1,1'-biphenyl]-4-yl]-methyl]-1H-benzazepin-3(R)-yl] propanamide, hydrochloride (Example 35, Step I) and dimethylcarbamyl chloride according to the procedure described in Example 37, Step A. $^1$H NMR (200 MHz, CD$_3$OD): δ 1.39 (s, 6H), 1.82 (m, 1H), 2.18–2.58 (m, 3H), 2.81 (s, 6H), 4.20 (d, 5 Hz, 2H), 4.32 (m, 1H), 4.86 (d, 15 Hz, 1H), 5.01 (s, 2H), 5.31 (d, 15 Hz, 1H), 6.40 (t, 5 Hz, 1H), 7.06–7.40 (m, 17H). FAB-MS: calculated for C$_{39}$H$_{43}$N$_5$O$_5$ 661; found 662 (M+H, 80%).

Step B:
2-Amino-2-methyl-N-[2,3,4,5-tetrahydro-1-[[2'-[[[(N,N-dimethylamino)carbonyl]amino]methyl][1,1'-biphenyl]-4-yl]methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[[(N,N-dimethylamino)carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 1.53 (s, 3H), 1.62 (s, 3H), 2.25 (m, 2H), 2.58 (m, 2H), 2.83 (s, 6H), 4.22 (s, 2H), 4.38 (dd, 11, 9 Hz; 1H), 4.98 (d, 15 Hz, 1H), 5.20 (d, 15 Hz, 1H), 7.10 (m, 1H), 7.17–7.37 (m, 11H). FAB-MS: calculated for C$_{31}$H$_{37}$N$_5$O$_3$ 527; found 528 (M+H, 100%).

EXAMPLE 45

2-Amino-2-methyl-N-[2,3,4,5-tetrahydro-1-[[2'-[[[(4-morpholino)carbonyl]amino]methyl][1,1'-biphenyl]-4-yl]methyl]-2-oxo-1H-benzazepin-3(R)-yl]propanamide, trifluoroacetate Step A:
2-Benzyloxycarbonylamino-2-methyl-N-[2,3,4,5-tetrahydro-1-[[2'-[[[(4-morpholino)carbonyl]amino]methyl][1,1'-biphenyl]-4-yl]methyl]-2-oxo-1H-benzazepin-3(R)-yl]propanamide Prepared from 2-benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl]propanamide, hydrochloride (Example 35, Step I) and 4-morpholinocarbonyl chloride according to the procedure described in Example 37, Step A. $^1$H NMR (200 MHz, CDCl$_3$): δ 1.45 (s, 3H), 1.47 (s, 3H), 1.80 (m, 1H), 2.35–2.68 (m, 3H), 3.14 (t, 5 Hz, 2H), 3.58 (t, 5 Hz, 2H), 4.32 (d, 5 Hz, 2H), 4.45 (dd; 12, 7 Hz; 1H), 4.86 (d, 15 Hz, 1H), 5.03 (s, 2H), 5.20 (d, 15 Hz, 1H), 5.43 (s, 1H), 6.40 (t, 5 Hz, 1H), 7.05–7.42 (m, 19H). FAB-MS: calculated for C$_{41}$H$_{45}$N$_5$O$_6$ 703; found 704 (M+H, 80%).

Step B:
2-Amino-2-methyl-N-[2,3,4,5-tetrahydro-1-[[2'-[[[(4-morpholino)carbonyl]amino]methyl][1,1'-biphenyl]-4-yl]methyl]-2-oxo-1H-benzazepin-3(R)-yl]propanamide, trifluoroacetate The title compound was prepared from 2-benzyloxycarbonylamino-2-methyl-N-[2,3,4,5-tetrahydro-1-[[2'-[[[(4-morpholino)carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 1.53 (s, 3H), 1.62 (s, 3H), 2.25 (m, 2H), 2.58 (m, 2H), 3.27 (t, 5 Hz, 2H), 3.58 (t, 5 Hz, 2H), 4.24 (s, 2H), 4.37 (dd; 11, 8 Hz; 1H), 4.99 (d, 15 Hz, 1H), 5.19 (d, 15 Hz, 1H), 7.10 (m, 1H), 7.17–7.40 (m, 11H). FAB-MS: calculated for C$_{33}$H$_{39}$N$_5$O$_4$ 569; found 570 (M+H, 100%).

EXAMPLE 46

2-Amino-2-methyl-N-[2,3,4,5-tetrahydro-1-[[2'-[[[[(ethoxycarbonyl)methylamino]carbonyl]amino]methyl][1,1'-biphenyl]-4-yl]methyl]-2-oxo-1H-benzazepin-3(R)-yl]propanamide, trifluoroacetate Step A: 2-Benzyloxycarbonylamino-2-methyl-N-[2,3,4,5-tetrahydro-1-[[2'-[[[[(ethoxycarbonyl)methylamino]carbonyl]amino]methyl][1,1'-biphenyl]-4-yl]methyl]-2-oxo-1H-benzazepin-3(R)-yl]propanamide To a slurry of 200 mg (0.284 mmol) of 2-benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl]propanamide, trifluoroacetate (Example 36, Step A) in 1.0 mL of dry methylene chloride under a nitrogen atmosphere was added 0.080 mL (0.57 mmol) of triethylamine. The mixture was stirred at room temperature for 30 minutes (mixture A).

In a separate flask was placed 59.4 mg (0.426 mmol) of glycine ethyl ester hydrochloride in 2.0 mL of dry methylene chloride under a nitrogen atmosphere. To this slurry was added 0.080 mL (0.57 mmol) of triethylamine. After 5 minutes, 69 mg (0.43 mmol) of 1,1'-carbonyldiimidazole was added. The resulting mixture was stirred at room temperature for 15 minutes then the previously prepared amine solution (mixture A) was added via cannula to the reaction mixture. After stirring for 24 hours at room temperature, the reaction mixture was diluted with 100 mL of ethyl acetate, washed with 25 mL of saturated aqueous ammonium chloride, 25 mL of saturated sodium bicarbonate and 25 mL of brine. The organic layer was removed, dried over magnesium sulfate, filtered and the solvent removed under vacuum. The resulting material was purified by flash column chromatography on silica gel eluting with ethyl acetate/hexanes (90:10) to afford 149 mg (73%) of the product as a white foam. $^1$H NMR (200 MHz, CD$_3$OD): δ 1.22 (t, 7 Hz, 3H), 1.39 (s, 6H), 1.82 (m, 1H), 2.15–2.55 (m, 3H), 3.81 (s, 2H), 4.13 (m, 4H), 4.32 (m, 1H), 4.86 (d, 15 Hz, 1H), 5.01 (s, 2H), 5.32 (d, 15 Hz, 1H), 7.08–7.43 (m, 17H). FAB-MS: calculated for C$_{41}$H$_{45}$N$_5$O$_7$ 719; found 720 (M+H, 50%).

Step B:
2-Amino-2-methyl-N-[2,3,4,5-tetrahydro-1-[[2'-[[[[(ethoxycarbonyl)methylamino]carbonyl]amino]methyl][1,1'-biphenyl]-4-yl]methyl]-2-oxo-1H-benzazepin-3(R)-yl]-propanamide, trifluoroacetate The title compound was prepared from 2-benzyloxycarbonylamino-2-methyl-N-[2,3,4,5- tetrahydro-1-[[2'-[[[[(ethoxycarbonyl)methylamino] carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 1.22 (t, 7 Hz, 3H), 1.53 (s, 3H), 1.62 (s, 3H), 2.25 (m, 2H), 2.58 (m, 2H), 3.82 (s, 2H), 4.24 (m, 4H), 4.38 (dd; 12, 9 Hz; 1H), 4.97 (d, 15 Hz, 1H), 5.20 (d, 15 Hz, 1H), 7.10–7.40 (m, 12H). FAB-MS: calculated for C$_{33}$H$_{39}$N$_5$O$_5$ 585; found 586 (M+H, 100%).

EXAMPLE 47

2-Amino-2-methyl-N-[2,3,4,5-tetrahydro-1-[[2'-[[[[(carboxymethyl)amino]carbonyl]amino]methyl] [1,1'-biphenyl]-4-yl]methyl]-2-oxo-1H-benzazepin-3 (R)-yl]propanamide, trifluoroacetate Step A:
2-Benzyloxycarbonylamino-2-methyl-N-[2,3,4,5-tetrahydro-1-[[2'-[[[[(benzyloxycarbonyl)methylamino] carbonyl]amino]methyl][1,1'-biphenyl]-4-yl]methyl]-2-oxo-1H-benzazepin-3(R)-yl]propanamide Prepared from 2-benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl] propanamide, trifluoroacetate (Example 36, Step A) and glycine benzyl ester hydrochloride according to the procedure described in Example 46, Step A. $^1$H NMR (200 MHz, CD$_3$OD): δ 1.38 (s, 6H), 1.82 (m, 1H), 2.18–2.60 (m, 3H), 3.86 (s, 2H), 4.13 (s, 2H), 4.32 (m, 1H), 4.84 (d, 15 Hz, 1H), 4.99 (s, 2H), 5.11 (s, 2H), 5.30 (d, 15 Hz, 1H), 7.05–7.41 (m, 22H). FAB-MS: calculated for C$_{46}$H$_{47}$N$_5$O$_7$ 781; found 782 (M+H, 90%).

Step B:
2-Amino-2-methyl-N-[2,3,4,5-tetrahydro-1-[[2'-[[[[(carboxymethyl)amino]carbonyl]amino]methyl][1,1'-biphenyl]-4-yl]methyl]-2-oxo-1H-benzazepin-3(R)-yl] propanamide, trifluoroacetate The title compound was prepared from 2-benzyloxycarbonylamino-2-methyl-N-[2,3,4,5-tetrahydro-1-[[2'-[[[[(benzyloxycarbonyl)methylamino] carbonyl]amino]methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 1.53 (s, 3H), 1.62 (s, 3H), 2.25 (m, 2H), 2.59 (m, 2H), 3.82 (s, 2H), 4.15 (s, 2H), 4.38 (dd; 12, 9 Hz; 1H), 4.97 (d, 15 Hz, 1H), 5.19 (d, 15 Hz, 1H), 7.10–7.43 (m, 12H). FAB-MS: calculated for C$_{31}$H$_{35}$N$_5$O$_5$ 557; found 558 (M+H, 25%).

EXAMPLE 48

3-Amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide, trifluoroacetate Step A:
2,2-Dimethylbutanedioic acid, 4-methyl ester
2,2-Dimethylsuccinic acid (20 g, 140 mmol) dissolved in 200 mL of absolute methanol at 0° was treated dropwise with 2 mL of concentrated sulfuric acid. After the addition was complete, the mixture was allowed to warm to room temperature and stirred for 16 hours.

The mixture was concentrated under vacuum to 50 mL and slowly treated with 200 mL of saturated aqueous sodium bicarbonate. The mixture was washed with hexane (3×) and the aqueous layer removed and cooled in an ice bath. The mixture was acidified to pH 2 by slow addition of 6N HCl then extracted with ether (8×). The combined extracts were washed with brine, dried over magnesium sulfate, filtered and solvents removed under vacuum. The residue was dried at room temperature under vacuum to afford 14.7 g (91.8 mmol, 67%) of a viscous oil that slowly solidified upon standing. $^1$H NMR analysis indicates the product is a mixture of the desired compound and 15% of the isomeric 2,2-dimethylbutanedioic acid, 1-methyl ester. NMR (200 MHz, CDCl$_3$) of desired compound: δ 1.29 (s, 6H), 2.60 (s, 2H), 3.66 (s, 3H). NMR (200 MHz, CDCl$_3$) isomer: δ 1.28 (s, 6H), 2.63 (s, 2H), 3.68 (s, 3H).

Step B:
3-[Benzyloxycarbonylamino]-3-methylbutanoic acid, methyl ester

To 14.7 g (91.8 mmol) of 2,2-dimethylbutanedioic acid-4-methyl ester (Step A), containing 15% of the isomeric 1-methyl ester compound, in 150 mL of benzene was added 13 mL of triethylamine (9.4 g, 93 mmol, 1.01 eq) followed by 21.8 mL of diphenylphosphoryl azide (27.8 g, 101 mmol, 1.1 eq). The mixture was heated under nitrogen at reflux for 45 minutes then 19 mL (19.9 g, 184 mmol, 2 eq) of benzyl alcohol was added and refluxing continued for 16 hours.

The mixture was cooled, filtered and the filtrate concentrated to a minimum volume under vacuum. The residue was redissolved in 250 mL of ethyl acetate, washed with water, saturated aqueous sodium bicarbonate (2×) and brine. The organic layer was removed, dried over magnesium sulfate, filtered and the filtrate concentrated to a minimum volume under vacuum. The crude product was purified by medium pressure liquid chromatography on silica, eluting with hexane/ethyl acetate (4:1), to afford 18.3 g (68.9 mmol, 75%) of the product as a pale yellow liquid in addition to a small amount of pure 3-[benzyloxycarbonylamino]-2,2-dimethylpropanoic acid, methyl ester. $^1$H NMR (200 MHz, CDCl$_3$) of major product: δ 1.40 (s, 6H), 2.69 (s, 2H), 3.63 (s, 3H), 5.05 (s, 2H), 5.22 (br s, 1H), 7.32 (s, 5H). $^1$H NMR (200 MHz, CDCl$_3$) of 3-[benzyloxycarbonylamino]-2,2-dimethylpropanoic acid, methyl ester (200 MHz, CDCl$_3$): δ 1.19 (s, 6H), 3.30 (d, 7 Hz, 2H; resonance collapses to singlet in CD$_3$OD), 3.67 (s, 3H), 5.09 (s, 2H), 5.22 (br s, 1H; resonance absent in CD$_3$OD), 7.3 (br s,5H).

Step C:
3-Benzyloxycarbonylamino-3-methylbutanoic acid

A solution of 18.3 g (68.9 mmol) of methyl 3-benzyloxycarbonylamino-3-methylbutanoate (Step B) in 20 mL of methanol at room temperature was treated dropwise with 51 mL of 2N NaOH (102 mmol, 1.5 eq). The mixture was stirred at room temperature for 16 hours then transferred to a separatory funnel and washed with hexane (3×). The aqueous layer was removed, cooled to 0° and slowly acidified to pH 2 (paper) by dropwise addition of 6N HCl. This mixture was extracted with ether (6×); combined extracts were washed with 1N HCl and brine, then dried over magnesium sulfate, filtered and solvent removed under vacuum to afford 17.3 g (68.7 mmol, 99%) of the product. $^1$H NMR (200 MHz, CDCl$_3$): δ 1.42 (s, 6H), 2.77 (s, 2H), 5.06 (s, 2H), 5.2 (br s, 1H), 7.3 (s, 5H).

Step D:
3-Benzyloxycarbonylamino-3-methyl-N-[2,3,4,5-tetrahydro-2-oxo-1H-benzazepin-3(R)-yl]butanamide Prepared from 3-benzyloxycarbonylamino-3-methylbutanoic acid (Step C) and 3(R)-amino-2,3,4,5-tetrahydro-1H-benzazepin-2-one (Example 1, Step E) substituting benzotriazol-1-yloxytripyrrolidinophosphonium hexafluorophosphate for benzotriazol-1-yloxytris (dimethylamino)phosphonium hexafluorophosphate according to the procedure described in Example 1, Step I. $^1$H NMR (200 MHz, CDCl₃): δ 1.37 (s, 6H), 1.82 (m, 1H), 2.45–2.75 (m, 4H), 2.86 (m, 1H), 4.49 (m, 1H), 5.05 (dd; 10, 6 Hz; 2H), 5.55 (s, 1H), 6.73 (s, 1H), 6.96 (d, 4 Hz, 1H), 7.10–7.40 (m, 8H) and 8.68 (s, 1H). FAB-MS: calculated for C₂₃H₂₇N₃O₄ 409; found 410 (M+H, 100%).

Step E:

2'-[(t-Butoxycarbonylamino)methyl]-1,1'-biphenyl-4-methanol, acetate ester

To solution of 500 mg (1.60 mmol) of 2'-[(t-butoxycarbonylamino)methyl]-1,1'-biphenyl-4-methanol (Example 35, Step E) in 1 mL of dry methylene chloride under a nitrogen atmosphere at room temperature was added by syringe 0.267 mL (1.91 mmol) of triethylamine followed by 0.165 mL (1.76 mmol) of acetic anhydride. The reaction mixture was stirred for 1 hour then diluted with 150 mL of ethyl acetate, washed with saturated aqueous ammonium chloride, saturated aqueous sodium bicarbonate, saturated aqueous sodium chloride, dried over magnesium sulfate and filtered. The solvent was removed under vacuum to give 583 mg (>100%, containing a minor amount of ethyl acetate) of the product as a white solid which was used in the next step without further purification. ¹H NMR (200 MHz, CDCl₃): δ 1.39 (s, 9H), 2.10 (s, 3H), 4.22 (d, 6 Hz, 2H), 4.65 (s, 1H), 5.12 (s, 2H), 7.18–7.48 (m, 8H). FAB-MS: calculated for C₂₁H₂₅NO₄ 355; found 356 (M+H).

Step F:

2'-Aminomethyl-1,1'-biphenyl-4-methanol, acetate ester, trifluoroacetate

Prepared from 2'-[(t-butoxycarbonylamino)methyl]-1,1'-biphenyl-4-methanol, acetate ester (Step E) according to the procedure described in Example 36, Step A. ¹H NMR (200 MHz, CDCl₃): δ 2.03 (s, 3H), 3.98 (s, 2H), 5.07 (s, 2H), 7.18–7.48 (m, 8H), 7.75 (s, 3H). FAB-MS: calculated for C₁₆H₁₇NO₂ 255; found 256 (M+H, 80%).

Step G:

2'-[[(Methylamino)carbonyl]amino]methyl-1,1'-biphenyl-4-methanol, acetate ester

Prepared from 2'-aminomethyl-1,1'-biphenyl-4-methanol, acetate ester, trifluoroacetate (Step F) according to the procedure described in Example 37, Step A. ¹H NMR (200 MHz, CDCl₃): δ 2.10 (s, 3H), 2.65 (d, 4.8 Hz, 3H), 4.27 (d, 4.8 Hz, 2H), 4.52 (m, 1H), 5.12 (s, 2H), 7.18–7.48 (m, 8H). FAB-MS: calculated for C₁₈H₂₀N₂O₃ 312; found 313 (M+H, 100%).

Step H:

2'-[[(Methylamino)carbonyl]amino]methyl-1,1'-biphenyl-4-methanol

To a solution of 498 mg (1.60 mmol) of 2'-[[(methylamino)carbonyl]amino]methyl-1,1'-biphenyl-4-methanol, acetate ester (Step G) in 10 mL of THF/water (3:1) was added 335 mg (7.98 mmol) of lithium hydroxide monohydrate. After stirring at room temperature for 16 hours the reaction mixture was diluted with 150 mL of ethyl acetate and washed with brine (3×50 mL). The organic layer was dried over magnesium sulfate, filtered and the solvent removed under vacuum to afford 411 mg (95%) of the product as a white solid. ¹H NMR (200 MHz, CD₃OD): δ 2.64 (s, 3H), 4.20 (s, 2H), 4.62 (s, 2H), 7.12–7.45 (m, 8H). FAB-MS: calculated for C₁₆H₁₈N₂O₂ 270; found 271 (M+H, 100%).

Step I:

2'-[[(Methylamino)carbonyl]amino]methyl-1,1'-biphenyl-4-methanol, methanesulfonate ester To solution of 100 mg (0.17 mmol) of 2'-[[(methylamino)carbonyl]amino]methyl-1,1'-biphenyl-4-methanol (Step H) in 5 mL of dry methylene chloride and 1 mL dry dimethylformamide under a nitrogen atmosphere at 0° C. was added by syringe 0.077 mL (0.56 mmol) of triethylamine followed by 0.034 mL (0.44 mmol) of methanesulfonyl chloride. The reaction mixture was stirred for 30 minutes at 0° C. then diluted with 75 mL of methylene chloride, washed with water, saturated aqueous sodium bicarbonate, saturated aqueous sodium chloride then dried over sodium sulfate and filtered. The solvent was removed under vacuum to give 128 mg (100%) of the product as a white solid which was used in the next step without further purification. ¹H NMR (200 MHz, CDCl₃): δ 2.66 (d, 4 Hz, 3H), 2.97 (s, 3H), 4.26 (d, 5 Hz, 2H), 4.42 (m, 1H), 5.26 (s, 2H), 7.18–7.48 (m, 8H). FAB-MS: calculated for C₁₇H₂₀N₂O₄S 348; found 349 (M+H, 100%).

Step J:

3-Benzyloxycarbonylamino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]-butanamide Prepared from 3-benzyloxycarbonylamino-3-methyl-N-[2,3,4,5-tetrahydro-2-oxo-1H-benzazepin-3(R)-yl]butanamide (Step D) and 2'-[[(methylamino)carbonyl]amino]methyl-1,1'-biphenyl-4-methanol, methanesulfonate ester (Step I) according to the procedure described in Example 35, Step H. ¹H NMR (200 MHz, CDCl₃): δ 1.33 (s,6H), 1.78 (m, 1H), 2.37–2.63 (m, 3H), 2.60 (d, 5 Hz, 3H), 4.20 (d, 6 Hz, 2H), 4.52 (m, 2H), 4.72 (t, 6 Hz, 1H), 4.86 (d, 16 Hz, 1H), 4.89 (s, 2H), 5.10 (d, 15 Hz, 1H), 5.69 (s, 1H), 6.73 (d, 7.5 Hz, 1H), 7.08–7.35 (m, 16H) 7.40 (m, 1H). FAB-MS: calculated for C₃₉H₄₃N₅O₅ 661; found 662 (M+H, 40%).

Step K:

3-Amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide, trifluoroacetate The title compound was prepared from 3-benzyloxycarbonylamino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide (Step J) according to the procedure described in Example 36, Step C. ¹H NMR (200 MHz, CD₃OD): δ 1.32 (s, 3H), 1.35 (s, 3H), 2.0–2.35 (m, 2H), 2.40–2.62 (m, 4H), 2.65 (s, 3H), 4.14 (dd; 17, 15 Hz; 2H), 4.40 (dd; 12, 8 Hz; 1H), 4.97 (d, 15 Hz, 1H), 5.21 (d, 15 Hz, 1H), 7.10–7.41 (m, 12H). FAB-MS: calculated for C₃₁H₃₇N₅O₃ 527; found 528 (M+H, 100%).

EXAMPLE 49

3-[2(R)-Hydroxypropyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide, trifluoroacetate Step A:

3-Amino-3-methyl-N-[2,3,4,5-tetrahydro-2-oxo-1H-benzazepin-3(R)-yl]-butanamide, trifluoroacetate To a solution of 150 mg (0.40 mmol) of 3-t-butoxycarbonylamino-3-methyl-N-[2,3,4,5-tetrahydro-2-oxo-1H-benzazepin-3(R)-yl]butanamide (Example 1, Step I) in 2 mL of methylene chloride at 0° C. was added 2 mL of trifluoroacetic acid and the mixture stirred at room temperature for 1 hour. All volatiles were removed under vacuum to give 130 mg (0.33 mmol, 84%) of the product. ¹H NMR (200 MHz, CD₃OD): δ 1.33 (s, 3H), 1.37 (s, 3H), 2.12 (m, 1H), 2.3–2.6 (m, 3H), 2.6–3.0 (m, 2H), 4.37 (dd; 8, 12 Hz; 1H), 7.02 (d, 8 Hz, 1H), 25 7.1–7.3 (m, 3H). FAB-MS: calculated for C₁₅H₂₁N₃O₂ 275; found 276 (M+H, 100%).

Step B:

3-[2(R)-Benzyloxypropyl]amino-3-methyl-N-[2,3,4,5-tetrahydro-2-oxo-1H-benzazepin-3(R)-yl]butanamide, trifluoroacetate To a solution of 1.0 g (2.6 mmol) of 3-amino-3-methyl-N-[2,3,4,5-tetrahydro-2-oxo-1H-benzazepin-3(R)-yl]butanamide, trifluoroacetate (Step A) in 25 mL of dry methanol was added 3.0 g of dry 3 Å powdered molecular sieves followed by a solution of 2.5 g (17 mmol) of (R)-2-benzyloxypropanol (prepared from methyl D-lactate according to the procedure of Hanessian and Kloss, *Tetrahedron Lett.*, 26, 1261–1264 (1985).) in 5 mL of dry methanol. The pH of the mixture was carefully adjusted to 6 by the addition of trifluoroacetic acid. The reaction was stirred for 2 hours at room temperature at which time 15.4 mL (15.4 mmol) of a 1.0 M solution of sodium cyanoborohydride in tetrahydrofuran was added by syringe. The reaction was stirred for 72 hours then filtered through a pad of Celite. To the filtrate was added 5 mL of trifluoroacetic acid (CAUTION! evolution of hydrogen cyanide) and the resulting mixture was stirred for three hours. The solvent was removed under vacuum to afford a clear oil which was purified by reverse phase medium pressure liquid chromatography on C-8, eluting with methanol/0.1% aqueous trifluoroacetic acid (60:40), to afford 1.27 g (2.36 mmol, 92%) of the product as a white solid. $^1$H NMR (200 MHz, CD$_3$OD): δ 1.31 (d, 6 Hz, 3H), 1.40 (s, 3H), 1.43 (s, 3H), 2.17 (m, 1H), 2.30 (m, 1H), 2.6–3.1 (m, 5H), 3.22 (dd; 3, 12 Hz; 1H), 3.86 (m, 1H), 4.48 (dd; J, 12 Hz; 1H), 4.50 (d, 12 Hz, 1H), 4.70 (d, 12 Hz, 1H), 7.11 (d, 8 Hz, 1H), 7.15–7.45 (m, 8H). FAB-MS: calculated for C$_{25}$H$_{33}$N$_3$O$_3$ 423; found 424 (M+H, 100%).

Step C:

3-[2(R)-Benzyloxypropyl]amino-3-methyl-N-[2,3,4,5-tetrahydro-2-oxo-1H-benzazepin-3(R)-yl]butanamide To a solution of 2.034 g (3.788 mmol) of the intermediate obtained in Step B in 40 mL of methylene chloride was added 40 mL of water. The mixture was stirred vigorously while sufficient solid potassium carbonate was added to adjust the pH of the aqueous layer to 10–11. Stirring was discontinued and the layers allowed to separate. The organic layer was removed and the aqueous layer extracted twice more with methylene chloride. The combined extracts were dried over potassium carbonate, filtered and solvents removed under vacuum to afford 1.53 g (3.62 mmol, 95%) of the product as a white solid.

Step D:

3-[2(R)-Benzyloxypropyl]amino-3-methyl-N-[2,3,4,5-tetrahydro-1-[[2'-[[[(methylamino)carbonyl]amino]-methyl][1,1'-biphenyl]-4-yl]methyl]-2-oxo-1H-benzazepin-3(R)-yl]butanamide Prepared from 3-[2(R)-benzyloxypropyl]amino-3-methyl-N-[2,3,4,5-tetrahydro-2-oxo-1H-benzazepin-3(R)-yl]butanamide (Step C) and 2'-[[(methylamino)carbonyl]aminomethyl-1,1'-biphenyl-4-methanol, methanesulfonate ester (Example 48, Step I) according to the procedure described in Example 35, Step H. $^1$H NMR (200 MHz, CD$_3$OD): δ 1.10 (s, 3H), 1.12 (s, 3H), 1.18 (d, 6 Hz, 3H), 1.95 (m, 1H), 2.12–2.39 (m, 3H), 2.40–2.63 (m, 3H), 2.63 (s, 3H), 3.70 (m, 1H), 4.13 (s, 2H), 4.42 (dd; 12, 8 Hz; 1H), 4.46 (d, 12 Hz, 1H), 4.59 (d, 12 Hz, 1H), 4.93 (d, 15 Hz, 1H), 5.23 (d, 15 Hz, 1H), 7.02–7.40 (m, 17H). FAB-MS: calculated for C$_{41}$H$_{49}$N$_5$O$_4$ 675; found 676 (M+H, 100%).

Step E:

3-[2(R)-Hydroxypropyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]-butanamide, trifluoroacetate To a solution of 233 mg (0.345 mmol) of 3-[2(R)-benzyloxypropyl]amino-3-methyl-N-[2,3,4,5-tetrahydro-1-[[2'-[[[(methylamino)carbonyl]amino]methyl][1,1'-biphenyl]-4-yl]methyl]-2-oxo-1H-benzazepin-3(R)-yl]butanamide (Step D) in 5 mL methanol was added 5 drops of concentrated hydrochloric acid. The resulting mixture was hydrogenated at ambient temperature over 50 mg of 30% palladium on carbon catalyst at 50 psi for 24 hours. The mixture was filtered through Celite. To the filtrate was added 3 drops of trifluoroacetic acid and the solvent was removed under vacuum to give a solid which was purified by reverse phase medium pressure liquid chromatography on C-8, eluting with methanol/0.1% aqueous trifluoroacetic acid (55:45), to afford 157 mg (65%) of the title compound as a white solid. $^1$H NMR (200 MHz, CD$_3$OD): δ 1.18 (d, 6 Hz, 3H), 1.34 (s, 3H), 1.36 (s, 3H), 2.02–2.22 (m, 1H), 2.22–2.43 (m, 1H), 2.48–2.65 (m, 5H), 2.65 (s, 3H), 2.78 (m, 1H), 3.90 (m, 1H), 4.16 (s, 2H), 4.38 (dd; 12, 8 Hz; 1H), 5.03 (d, 15 Hz, 1H), 5.17 (d, 15 Hz, 1H), 7.10–7.40 (m, 12H). FAB-MS: calculated for C$_{34}$H$_{43}$N$_5$O$_4$ 585; found 586(M+H, 40%).

EXAMPLE 50

3-[2(S),3-Dihydroxypropyl]amino-3-methyl-N-[2,3,4,5-tetrahydro-1-[[2'-[[[(methylamino)carbonyl]amino]methyl][1,1'-biphenyl]-4-yl]-methyl]-2-oxo-1H-benzazepin-3(R)-yl]butanamide, trifluoroacetate Step A:

3-Amino-3-methyl-N-[2,3,4,5-tetrahydro-2-oxo-1H-benzazepin-3(R)-yl]butanamide,

To a solution of 502 mg (1.34 mmol) of 3-t-butoxycarbonylamino-3-methyl-N-[2,3,4,5-tetrahydro-2-oxo-1H-benzazepin-3(R)-yl]butanamide (Example 1, Step I) in 3 mL of methylene chloride at 0° C. was added 0.160 mL (1.47 mmol) of anisole followed by 3 mL of trifluoroacetic acid. The mixture stirred at room temperature for 3 hours. All volatiles were removed under vacuum to give an oil which was dissolved in 10 mL of water. To this solution was added 268 mg (6.7 mmol) of sodium hydroxide and the resulting mixture was stirred until all the solids were dissolved. The solution was transferred to a separatory funnel and the aqueous layer was extracted with chloroform (3×50 mL). The combined organic extracts were washed with brine, dried over sodium sulfate and filtered. The solvent was removed under vacuum to afford 368 mg (100%) of the product as a white solid. $^1$H NMR (200 MHz, CDCl$_3$): δ 1.27 (s, 6H), 1.95–2.30 (m, 2H), 2.37–2.75 (m, 3H), 2.80–3.02 (m, 1H), 3.48 (s, 2H), 4.52 (m, 1H), 6.97 (m, 1H), 7.1–7.27 (m, 3H), 7.98 (s, 1H), 8.29 (d, 7 Hz, 1H). FAB-MS: calculated for C$_{15}$H$_{21}$N$_3$O$_2$ 275; found 276 (M+H, 100%).

Step B:

3-[[2,2-Dimethyl-1,3-dioxolan-4(S)-yl]methyl]amino-3-methyl-N-[2,3,4,5-tetrahydro-2-oxo-1H-benzazepin-3(R)-yl]butanamide, To a solution of 368 mg (1.34 mmol) of 3-amino-3-methyl-N-[2,3,4,5-tetrahydro-2-oxo-1H-benzazepin-3(R)-yl]butanamide (Step A) in 10 mL of dry methanol was added 1.5 g of dry 4 Å powdered molecular sieves followed by a solution of 520 mg (4.0 mmol) of D-glyceraldehyde acetonide (used crude as prepared according to the procedure of L. W. Hertel, C. S. Grossman and J. S. Kroin, *Syn. Comm.* 1991, 21, 151–154.) in 5 mL of dry methanol. The pH of the mixture was carefully adjusted to 6 by the addition of 3 drops of acetic acid. The reaction was stirred for 5 hours at room temperature at which time 4.0 mL (4.0 mmol) of a 1.0 M solution of sodium cyanoborohydride in tetrahydrofuran was added by syringe. The reaction was stirred for 16 hours then filtered through a pad of Celite. The solvent was removed under vacuum to afford a clear oil which was purified by flash column chromatography on silica gel eluting with chloroform/10% aqueous ammonium hydroxide (33%) in methanol (92:8) to afford 387 mg (78%) of the product as a white solid. $^1$H NMR (200 MHz, CD$_3$OD): δ 1.10 (s, 6H), 1.28 (s, 3H), 1.34 (s, 3H), 2.08 (m, 1H), 2.26 (dd; 16, 15 Hz; 2H), 2.44 (m, 1H), 2.58–2.75 (m, 3H), 2.87 (m, 1H), 3.63 (dd; 8, 7 Hz; 1H), 4.05 (dd; 8, 7 Hz; 1H), 4.20 (m, 1H), 4.38 (dd; 12, 8 Hz; 1H), 4.84 (s, 1H), 7.00–7.40 (m, 4H). FAB-MS: calculated for C$_{21}$H$_{31}$N$_3$O$_4$ 389; found 390 (M+H, 100%).

Step C:

3-[[2,2-Dimethyl-1,3-dioxolan-4(S)-yl]methyl]amino-3-methyl-N-[2,3,4,5-tetrahydro-1-[[2'-[[[(methylamino) carbonyl]amino]methyl][1,1'-biphenyl]-4-yl]methyl]-2-oxo-1H-benzazepin-3(R)-yl]butanamide Prepared from 3-[[2,2-dimethyl-1,3-dioxolan-4(S)-yl]methyl]amino-3-methyl-N-[2,3,4,5-tetrahydro-2-oxo-1H-benzazepin-3(R)-yl]butanamide (Step B) and 2'-[[(methylamino)carbonyl]amino]methyl-1,1'-biphenyl-4-methanol, methanesulfonate ester (Example 48, Step I) according to the procedure described in Example 35, Step H.$^1$H NMR (200 MHz, CD$_3$OD): δ 1.14 (s, 6H), 1.28 (s, 3H), 1.34 (s, 3H), 2.07 (m, 1H), 2.20–2.42 (m, 3H), 2.48–2.76 (m, 4H), 2.64 (s, 3H), 3.64 dd; 8, 6 Hz; 1H), 4.05 (dd; 8, 6 Hz; 1H), 4.14 (s, 2H), 4.20 (m, 1H), 4.40 (dd; 12, 8 Hz; 1H), 4.94 (d, 15 Hz, 1H), 5.27 (d, 15 Hz, 1H), 7.10–7.40 (m, 12H). FAB-MS: calculated for C$_{37}$H$_{46}$N$_5$O$_5$ 641; found 642 (M+H, 80%).

Step D:

3-[2(S),3-Dihydroxypropyl]amino-3-methyl-N-[2,3,4,5-tetrahydro-1-[[2'-[[[(methyl-amino)carbonyl]amino]methyl][1,1'-biphenyl]-4-yl]methyl]-2-oxo-1H-benzazepin-3(R)-yl] butanamide. trifluoroacetate To a solution of 137 mg (0.213 mmol) of 3-[[2,2-dimethyl-1,3-dioxolan-4(S)-yl]methyl]amino-3-methyl-N-[2,3,4,5-tetrahydro-1-[[2'-[[[(methylamino)carbonyl]amino] methyl][1,1'-biphenyl]-4-yl]-methyl]-2-oxo-1H-benzazepin-3(R)-yl]butanamide (Step C) in 2 mL of methanol was added 2.0 mL of 50% aqueous trifluoroacetic acid. The resulting solution was stirred at room temperature for 3 hours at which time the solvent was removed under vacuum to give a solid which was purified by reverse phase medium pressure liquid chromatography on C-8, eluting with methanol/0.1% aqueous trifluoroacetic acid (55:45), to afford 108 mg (70%) of the title compound as a white solid. $^1$H NMR (200 MHz, CD$_3$OD): δ 1.35 (s, 3H), 1.37 (s, 3H), 2.02–2.22 (m, 1H), 2.22–2.43 (m, 1H), 2.50–2.70 (m,4H), 2.64 (s,3H), 2.94 (dd, 12, 9 Hz; 1H), 3.17 (dd, 12, 3 Hz; 1H), 3.51 (m, 2H), 3.82 (m, 1H), 4.16 (s, 2H), 4.38 (dd, 12, 8 Hz; 1H), 5.03 (d, 15 Hz, 1H), 5.14 (d, 15 Hz, 1H), 7.10–7.40 (m, 12H). FAB-MS: calculated for C$_{34}$H$_{43}$N$_5$O$_5$ 601; found 602 (M+H, 40%).

EXAMPLE 51

2-Amino-2-methyl -N-[2,3,4,5-tetrahydro-1-[[2'-[[[(cyclopropylamino)carbonyl]amino]methyl][1,1'-biphenyl]-4-yl]methyl]-2-oxo-1H-benzazepin-3(R)-yl]propanamide, trifluoroacetate Step A:

2-Benzyloxycarbonylamino-2-methyl-N-[2,3,4,5-tetrahydro-1-[[2'-[[[(cyclopropylamino)carbonyl]amino] methyl][1,1'-biphenyl]-4-yl]methyl]-2-oxo-1H-benzazepin-3(R)-yl]-propanamide Prepared from 2-benzyloxycarbonylamino-2-methyl-N-[2,3,4,5-tetrahydro-2-oxo-1-[[2'-(aminomethyl)[1,1'-biphenyl]-4-yl]methyl]-1H-benzazepin-3(R)-yl] propanamide, hydrochloride (Example 35, Step I) and cyclopropyl amine according to the procedure described in Example 46, Step A. $^1$H NMR (200 MHz, CD$_3$OD): δ 0.39 (m, 2H), 0.61 (m, 2H), 1.38 (s, 6H), 1.82 (m, 1H), 2.18–2.58 (m, 4H), 4.18 (s, 2H), 4.32 (m, 1H), 4.86 (d, 15 Hz, 1H), 5.00 (s, 2H), 5.21 (d, 15 Hz, 1H), 7.10 (m, 1H), 7.14–7.40 (m, 16H). FAB-MS: calculated for C$_{40}$H$_{43}$N$_5$O$_5$ 673; found 674 (M+H, 70%).

Step B:

2-Amino-2-methyl-N-[2,3,4,5-tetrahydro-1-[[2'-[[[(cyclopropylamino)carbonyl]amino]methyl][1,1'-biphenyl]-4-yl]methyl]-2-oxo-1H-benzazepin-3(R)-yl] propanamide, trifluoroacetate The title compound was prepared from 2-benzyloxycarbonylamino-2-methyl-N-[2,3,4,5-tetrahydro-1-[[2'-[[[(cyclopropylamino)carbonyl]amino] methyl][1,1'-biphenyl]-4-yl]methyl]-2-oxo-1H-benzazepin-3(R)-yl]propanamide (Step A) according to the procedure described in Example 36, Step C. $^1$H NMR (200 MHz, CD$_3$OD): δ 0.39 (m, 2H), 0.62 (m, 2H), 1.53 (s, 3H), 1.62 (s, 3H), 2.10–2.45 (m, 3H), 2.58 (m, 2H), 4.19 (s, 2H), 4.37 (m, 1H), 4.98 (d, 15 Hz, 1H), 5.20 (d, 15 Hz, 1H), 7.08–7.40 (m, 12H). FAB-MS: calculated for C$_{32}$H$_{37}$N$_5$O$_3$ 539; found 540 (M+H, 80%).

EXAMPLE 52

2-Amino-2-methyl-N-[2,3,4,5-tetrahydro-1-[[2'-[[[(methylamino)carbonyl]amino]methyl]-3-bromo-[1,1'-biphenyl]-4-yl]methyl]-2-oxo-1H-benzazepin-3(R)-yl]propanamide Step A:

4-Methylphenyltrimethylstannane

To a solution of 546 g (2.74 mol) of trimethyltin chloride in tetrahydrofuran (4L) under nitrogen at −10° C. was added dropwise, maintaining the temperature below −5° C. over 4 hours, 4.14 L of 1.0 M p-tolylmagnesium bromide in diethyl ether (4.14 mol, 1.5 eq.). The suspension was allowed to warm slowly to room temperature over 12 hours then saturated ammonium chloride solution (1 L) was added followed by sufficient water (approximately 1 L) to dissolve the precipitate. The solution was extracted with ether-hexane (1:1) (1×4 L, 3×2 L). The combined organic phases were washed with brine, dried over magnesium sulfate and the solvents removed under vacuum. Purification by flash chromatography on silica gel eluting with hexane/ethyl acetate (95:5) gave a pale yellow oil containing white crystals of 4,4'-dimethylbiphenyl which were removed by filtration to leave 698 g (100%) of product. $^1$H NMR (300 MHz, CDCl$_3$): δ 0.30 (s, 9H), 2.34 (s, 3H), 7.19 (d, 7.7 Hz, 2H), 7.40 (d, 7.7 Hz, 2H).

Step B:

4'-Methyl-1'-biphenyl-2-nitrile

A solution of 2.00 g (11.0 mmol) of 2-bromobenzonitrile, 2.93 g (11.5 mmol) of 4-methylphenyltrimethylstannane (Step A) and 0.385 g (0.550 mmol) of bis-triphenylphosphine palladium (II) chloride in 50 mL of dry dimethylformamide under nitrogen was heated at 100° C. for 5.5 hours. The reaction was cooled to room temperature, poured into 150 mL of water and extracted with ether (3×150 mL). The combined ether extracts were washed with water (4×100 mL) and brine (100 mL), dried over magnesium sulfate, filtered and the solvents removed under vacuum. Purification by flash chromatography on silica gel, eluting with hexane/ether (85:15), afforded 1.69 g (80%) of the product contaminated with about 10% of 2-methylbenzonitrile. $^1$H NMR (200 MHz, CDCl$_3$): δ 2.40

(s, 3H), 7.27 (d, 7 Hz, 2H), 7.30–7.65 (m, 5H), 7.72 (d, 6 Hz, 1H). EI-MS: calculated for $C_{14}H_{11}N$ 193; found 193 ($M^+$, 100%).

Step C:

3'-Bromo-4'-methyl-1,1'-biphenyl-2-nitrile

A solution of 5.2 g (27 mmol) of 4'-methyl-1,1'-biphenyl-2-nitrile (Step B) in 60 mL of methylene chloride at 0° C. was treated with 6.7 g of silver trifluoroacetate (30 mmol). When all the silver trifluoroacetate was dissolved, 1.6 mL of bromine was added dropwise (4.95 g, 31 mmol) with vigorous stirring. After two hours, the reaction mixture was filtered and the solid washed with methylene chloride. The combined organic layers were washed once with dilute (<1N) aqueous sodium hydroxide and once with brine. The organic layer was removed, dried over magnesium sulfate, filtered and concentrated under vacuum. The residue was purified by preparative high pressure liquid chromatography on silica, eluting with 10% ether/hexane to give 3 g (41%) of product. $^1$H NMR (200 MHz, $CDCl_3$): δ 2.46 (s, 3H), 7.2–7.8 (m, 7H).

Step D:

3'-Bromo-4'-bromomethyl-1,1'-biphenyl-2-nitrile

A solution of 1.0 g (3.7 mmol) of 3'-bromo-4'methyl-1,1'-biphenyl-2-nitrile (Step C) in 15 mL of carbon tetrachloride under a nitrogen atmosphere was treated with 0.720 g (4.04 mmol) of N-bromosuccinimide followed by 60 mg (0.37 mmol) of azobisisobutyronitrile (AIBN). The reaction mixture was heated at reflux for four hours, cooled to room temperature and filtered through Celite. The solvent was removed under vacuum and the residue was dissolved in methylene chloride and treated with decolorizing carbon. The solids were filtered through Celite and the solvent removed under vacuum. The resulting solid was triturated with cold ether, filtered and air dried to afford 920 mg (71%) of the product as an off-white solid. $^1$H NMR (200 MHz, $CDCl_3$): δ 4.64 (s, 2H), 7.4–7.8 (m, 7H). EI-MS: calculated for $C_{14}H_9Br_2N$ 351; found 351 ($M^+$, 20%); 271 (M–Br, 100%).

Step E:

3'-Bromo-4'-acetoxymethyl-1,1'-biphenyl-2-nitrile

To a solution of 662 mg (1.89 mmol) of 3'-bromo-4'-bromomethyl-1,1'-biphenyl-2-nitrile (Step D) in 10 mL of dry dimethyl formamide was added 925 mg (9.43 mmol) of potassium acetate. The reaction mixture was heated at 50° C. for 2 hours then diluted with 100 mL of water. The mixture was extracted with ethyl acetate (3×100 mL). The organic extracts were combined, washed with water (100 mL), saturated aqueous sodium bicarbonate (100 mL) and brine (100 mL). The solution was dried over magnesium sulfate, filtered and the solvent removed under vacuum to give an oil which was purified by flash column chromatography on silica gel, eluting with hexanes/ethyl acetate (75:25), to afford 400 mg (64%) of the product as a white solid. $^1$H NMR (200 MHz, $CDCl_3$): δ 2.14 (s, 3H), 5.22 (s, 2H), 7.4–7.8 (m, 7H). EI-MS: calculated for $C_{16}H_{12}BrNO_2$ 329; found 329, 331 ($M^+$, 7%); 270, 272 (M–Br, 100%).

Step F:

3'-Bromo-4'-hydroxymethyl-1,1'-biphenyl-2-nitrile

Prepared from 3'-bromo-4'-acetoxymethyl-1,1'-biphenyl-2-nitrile (Step E) according to the procedure described in Example 48, Step H. $^1$H NMR (200 MHz, $CDCl_3$): δ 2.04 (s, 1H), 4.79 (s, 2H), 7.35–7.8 (m, 7H). EI-MS: calculated for $C_{14}H_{10}BrNO$ 287, 289; found 287, 289 ($M^+$, 5%), 269, 271 (M–$H_2O$, 100%).

Step G:

3'-Bromo-4'-t-butyldiphenylsilyloxymethyl-1,1'-biphenyl-2-nitrile

To a solution of 670 mg (2.35 mmol) of 3'-bromo-4'-hydroxymethyl-1,1'-biphenyl-2-nitrile (Step F) in 5 mL of dry dimethylformamide under a nitrogen atmosphere was added 237 mg (3.49 mmol) of imidazole. The reaction mixture was cooled to 0° C. and 0.73 mL (2.8 mmol) of t-butylchlorodiphenylsilane was added dropwise by syringe over 5 minutes. The resulting solution was stirrred at 0° C. for 15 minutes then at room temperature for 2 hours. The reaction mixture was poured into 100 mL of water and extracted with ether (3×75 mL). The combined ether extracts were washed with water (75 mL), saturated aqueous sodium bicarbonate (75 mL) and brine (75 mL). The organic layer was dried over magnesium sulfate, filtered and the solvent removed under vacuum to give an oil which was purified by flash column chromatography on silica gel, eluting with hexanes/ethyl acetate (9:1), to afford 1.24 g (100%) of the product as a clear oil. $^1$H NMR (200 MHz, $CDCl_3$): δ 1.13 (s, 3H), 4.80 (s, 2H), 7.30–7.50 (m, 9H), 7.55–7.80 (m, 7H), 7.86 (d, 8 Hz, 1H). FAB-MS: calculated for $C_{30}H_{28}BrNOSi$ 526; found 527, 528, 271 (60%).

Step H:

2'-Aminomethyl-3-bromo-1,1'-biphenyl-4-methanol

To a solution of 136 mg (0.258 mmol) of 3'-bromo-4'-t-butyldiphenylsilyloxymethyl-1,1'-biphenyl-2-nitrile (Step G) in 3 mL of dry methylene chloride under a nitrogen atmosphere was added 199 mg (0.775 mmol) of tetra-n-butylammonium borohydride. The reaction mixture was heated at reflux for 8 hours, cooled to room temperature, poured into 25 mL of water and extracted with ethyl acetate (3×35 mL). The combined organic extracts were washed with water (25 mL), A saturated aqueous sodium bicarbonate (25 mL) and brine (25 mL). The organic layer was dried over magnesium sulfate, filtered and the solvent removed under vacuum to give an oil which was dissolved in 3 mL of tetrahydrofuran and treated with 1 mL of 6N aqueous hydrochloric acid. The resulting solution was heated at reflux for 4 hours, cooled in an ice bath and quenched with 10 mL of 1N aqueous sodium hydroxide. The mixture was extracted with ethyl acetate (3×35 mL). The organic extracts were washed with water (25 mL), saturated aqueous sodium bicarbonate (25 mL) and brine (25 mL). The organic layer was dried over sodium sulfate, filtered and the solvent removed under vacuum to give an oil which was purified by flash column chromatography on silica gel, eluting with chloroform/10% ammonium hydroxide (33%) in methanol (9:1), to afford 43 mg (57%) of the product as an off-white solid. $^1$H NMR (200 MHz, $CD_3OD$): δ 3.69 (s, 2H), 4.68 (s, 2H), 7.16 (dd; 7, 6 Hz; 1H), 7.21–7.41 (m, 4H), 7.47 (dd; 9, 8 Hz; 1H), 7.58 (d, 8 Hz, 1H). FAB-MS: calculated for $C_{14}H_{14}BrNO$ 292; found 292, 293 (50%).

Step I:

2'-[[(Methylamino)carbonyl]amino]methyl-3-bromo-1,1'-biphenyl-4-methanol

To a solution of 68 mg (0.23 mmol) of 2'-aminomethyl-3-bromo-1,1'-biphenyl-4-methanol (Step H) in 3 mL of dry methylene chloride and 1 mL of dry dimethylformamide under nitrogen atmosphere at 0° C. was added 0.015 mL (0.25 mmol) of methyl isocyanate. The reaction mixture was stirred for 30 minutes at 0° C. then diluted with 100 mL of ethyl acetate, washed with water, saturated aqueous sodium bicarbonate, saturated aqueous sodium chloride, dried over magnesium sulfate and filtered. The solvent was removed under vacuum to give 71 mg (88%) of the product as a white solid which was used in the next step without further purification. $^1$H NMR (200 MHz, CD$_3$OD): δ 2.64 (s, 3H), 4.20 (s, 2H), 4.69 (s, 2H), 7.16 (m, 1H), 7.22–7.43 (m, 4H), 7.50 (d, 2 Hz, 1H), 7.58 (d, 8 Hz, 1H). FAB-MS: calculated for C$_{16}$H$_{17}$BrN$_2$O$_2$ 349; found 349, 351 (80%).

Step J:

2'-[[(Methylamino)carbonyl]amino]methyl-3-bromo-1,1'-biphenyl-4-methanol, methanesulfonate ester Prepared from 2'-[[(methylamino)carbonyl]amino]methyl-3-bromo-1,1'-biphenyl-4-methanol (Step I) according to the procedure described in Example 48, Step I. FAB-MS: calculated for C$_{17}$H$_{19}$BrN$_2$O$_4$S 427; found 427, 429 (40%).

Step K:

2-t-Butoxycarbonylamino-2-methyl-N-[2,3,4,5-tetrahydro-2-oxo-1H-benzazepin-3(R)-yl]propanamide Prepared from N-t-butoxycarbonyl-2-methylalanine and 3(R)-amino-2,3,4,5-tetrahydro-1H-1-benzazepin-2-one (Example 1, Step E) substituting benzotriazol-1-yloxytripyrrolidinophosphonium hexafluorophosphate for benzotriazol-1-yloxytris(dimethylamino)phosphonium hexafluorophosphate according to the procedure described in Example 1, Step I. $^1$H NMR (200 MHz, CDCl$_3$): δ 1.47 (s, 3H), 1.52 (s, 3H), 1.82 (m, 1H), 2.50–3.00 (m, 3H), 4.45 (m, 1H), 5.05 (s, 2H), 5.37 (s, 1H), 6.80–7.40 (m, 10H) and 8.65 (s, 1H). FAB-MS: calculated for C$_{22}$H$_{25}$N$_3$O$_4$ 395; found 396 (M+H, 100%).

Step L:

2-t-Butoxycarbonylamino-2-methyl-N-[2,3,4,5-tetrahydro-1-[[2'-[[[(methylamino)carbonyl]amino)methyl]-3-bromo-[1,1'-biphenyl]-4-yl]methyl]-2-oxo-1H-benzazepin-3(R)-yl]propanamide Prepared from 2-t-butoxycarbonylamino-2-methyl-N-[2,3,4,5-tetrahydro-2-oxo-1H-benzazepin-3(R)-yl]propanamide (Step K) and 2'-[[(methylamino)carbonyl]amino]methyl-3]-bromo-[1,1'-biphenyl-4-methanol, methanesulfonate ester (Step J) according to the procedure described in Example 35, Step H. $^1$H NMR (200 MHz, CDCl$_3$): δ 1.39 (s, 12H), 1.41 (s, 3H), 1.92 (m, 1H), 2.48–2.75 (m, 6H), 4.20 (d, 6 Hz, 2H), 4.52 (m, 2H), 4.70 (m, 1H), 4.92 (m, 2H), 7.08–7.35 (m, 10H) 7.42 (m, 1H).

Step M:

2-Amino-2-methyl-N-[2,3,4,5-tetrahydro-1-[[2'-[[[(methylamino)carbonyl]amino]methyl]-3-bromo-[1,1'-biphenyl]-4-yl]methyl]-2-oxo-1H-benzazepin-3(R)-yl]propanamide, trifluoroacetate To a solution of 146 mg (0.211 mmol) of 2-t-butoxycarbonylamino-2-methyl-N-[2,3,4,5-tetrahydro-1-[[2'-[[[(methylamino)carbonyl]amino]methyl]-3-bromo-[1,1'-biphenyl]-4-yl]methyl]-2-oxo-1H-benzazepin-3(R)-yl] butanamide (Step L) in 5 L of methylene chloride was added 5 drops of anisole followed by 5 mL of trifluoroacetic acid. The reaction mixture was stirred at room temperature for 1 hour then the solvent was removed under vacuum. The residue was purified by reverse phase medium pressure liquid chromatography on C-8, eluting with methanol/0.1% aqueous trifluoroacetic acid (60:40), to afford 87 mg (58%) of the title compound as a white solid. $^1$H NMR (200 MHz, CD$_3$OD): δ 1.52 (s, 3H), 1.59 (s, 3H), 2.32 (m, 2H), 2.60–3.02 (m, 2H), 2.65 (s, 3H), 4.17 (dd; 18, 14 Hz; 2H), 4.43 (dd; 12, 9 Hz; 1H), 4.90 (d, 16 Hz, 4H), 5.34 (d, 16 Hz, 2H), 7.10–7.42 (m, 8H), 7.50 (m, 3H). FAB-MS: calculated for C$_{30}$H$_{34}$BrN$_5$O$_3$ 592; found 593, 595 (100%).

EXAMPLE 53

2-Amino-2-methyl-N-[2,3,4,5-tetrahydro-1-[[2'-[2-[[methylaminocarbonyl]amino]ethyl][1,1'-biphenyl]-4-yl]methyl]-2-oxo-1H-benzazepin-3(R)-yl] propanamide, trifluoroacetate Step A:

2'-(2-cyanoethyl)-1,1'-biphenyl-4-methanol, t-butyldiphenylsilyl ether

To a solution of 1.50 g (3.84 mmol) of 4-(t-Butyldiphenylsiloxymethyl)phenylboronic acid (Example 35, Step C) in 8 mL of dry dimethylformamide was added 220 mg (0.19 mmol) of tetrakis(triphenylphosphine) palladium, 1.2 g (5.8 mmol) of tripotassium phosphate and 0.791 g (4.03 mmol) of 2-bromophenylacetonitrile. The resulting mixture was heated under nitrogen at 100° C. for 3 hours then cooled to room temperature. The reaction mixture was diluted with 100 mL of saturated aqueous ammonium chloride, transferred to a separatory funnel and extracted with ether (3×150 mL). The combined ether extracts were washed with saturated aqueous sodium bicarbonate (100 mL) and saturated aqueous sodium chloride (100 mL), dried over magnesium sulfate and filtered. The solvent was removed under vacuum to give a crude product which was purified by flash column chromatography on silica gel eluting with hexanes/ethyl acetate (9:1) to afford 1.3 g (73%) of the product as a clear oil. $^1$H NMR (200 MHz, CDCl$_3$): δ 1.10 (s, 9H), 3.82 (s, 2H), 4.82 (s, 2H), 7.18–7.47 (m, 11H), 7.50–7.62 (m, 3H), 7.73 (m, 4H). FAB-MS: calculated for C$_{31}$H$_{31}$NOSi 461; found 462 (M+H, 20%).

Step B:

2'-(2-Cyanoethyl)-1,1'-biphenyl-4-methanol

Prepared from 2'-(2-cyanoethyl)-1,1'-biphenyl-4-methanol, t-butyldiphenylsilyl ether (Step A) according to the procedure described in Example 35, Step F. $^1$H NMR (200 MHz, CDCl$_3$): δ 1.93 (s, 1H), 3.60 (s, 2H), 4.73 (d, 4 Hz, 2H), 7.27 (m, 3H), 7.33–7.63 (m, 5H). FAB-MS: calculated for C$_{15}$H$_{13}$NO 223; found 222 (M−H), 205 (M−H$_2$O, 100%).

Step C:

2'-(2-Cyanoethyl)-1,1'-biphenyl-4-methanol, t-butyldimethylsilyl ether

Prepared from 2'-(2-cyanoethyl)-1,1'-biphenyl-4-methanol (Step B) substituting t-butyldimethylsilyl chloride for t-butylchlorodiphenylsilane according to the procedure described in Example 52, Step G. $^1$H NMR (200 MHz, CDCl$_3$): δ 0.94 (s, 9H), 3.60 (s, 2H), 4.77 (s, 2H), 7.24 (m, 3H), 7.40 (m, 4H), 7.52 (m, 1H). FAB-MS: calculated for C$_{21}$H$_{27}$NOSi 337; found 336 (M−H, 10%), 206 (100%).

Step D:

2'-(2-Aminoethyl)-1,1'-biphenyl-4-methanol

Prepared from 2'-(2-cyanoethyl)-1,1'-biphenyl-4-methanol, t-butyldimethylsilyl ether (Step C) according to the procedure described in Example 52, Step H. $^1$H NMR (200 MHz, CD$_3$OD): δ 2.63 (m, 2H), 2.75 (m, 2H), 4.63 (s, 2H), 7.10–7.32 (m, 6H), 7.39 (d, 8 Hz, 2H). FAB-MS: calculated for $C_{15}H_{17}NO$ 227; found 242 (M+2Li, 100%).

Step E:

2'-[2-[Methylaminocarbonyl]amino]ethyl-1,1'-biphenyl-4-methanol

Prepared from 2'-(2-aminoethyl)-1,1'-biphenyl-4-methanol (Step D) according to the procedure described in Example 52, Step I. $^1$H NMR (200 MHz, CDCl$_3$): δ 2.56 (d, 5 Hz, 3H), 2.70 (t, 8 Hz, 2H), 2.89 (t, 5 Hz, 1H), 3.10 (m, 2H), 4.37 (m, 1H), 4.52 (t, 6 Hz, 1H), 4.67 (d, 5 Hz, 2H), 7.12–7.30 (m, 6H), 7.35 (d, 8 Hz, 1H). FAB-MS: calculated for $C_{17}H_{20}N_2O_2$ 284; found 285 (M+H, 100%).

Step F:

2'-[2-[Methylaminocarbonyl]amino]ethyl-1,1'-biphenyl-4-methanol, methanesulfonate ester Prepared from 2'-[2-[methylaminocarbonyl]amino]ethyl-1,1'-biphenyl-4-methanol (Step E) according to the procedure described in Example 48, Step I.

Step G:

2-t-Butoxycarbonylamino-2-methyl-N-[2,3,4,5-tetrahydro-1-[[2'-[2-[[methylaminocarbonyl]amino]ethyl][1,1'-biphenyl]-4-yl]methyl]-2-oxo-1H-benzazepin-3(R)-yl]propanamide Prepared from 2-t-butoxycarbonylamino-2-methyl-N-[2,3,4,5-tetrahydro-2-oxo-1H-benzazepin-3(R)-yl]propanamide (Example 52, Step K) and 2'-[2-[methylaminocarbonyl]amino]ethyl-1,1'-biphenyl-4-methanol, methanesulfonate ester (Step F) according to the procedure described in Example 35, Step H. $^1$H NMR (200 MHz, CDCl$_3$): δ 1.39 (s, 12H), 1.41 (s, 3H), 1.85 (m, 1H), 2.40–2.80 (m, 8H), 3.13 (m, 2H), 4.25 (m, 2H), 4.47 (m, 1H), 4.94 (d, 16 Hz, 1H), 4.96 (s, 1H), 5.11 (d, 16 Hz, 1H), 7.08–7.20 (m, 12H). FAB-MS: calculated for $C_{36}H_{45}N_5O_5$ 627; found 628 (M+H, 20%), 528 (100%).

Step H:

2-Amino-2-methyl-N-[2,3,4,5-tetrahydro-1-[[2'-[2-[[methylaminocarbonyl]amino]ethyl][1,1'-biphenyl]-4-yl]methyl]-2-oxo-1H-benzazepin-3(R)-yl]propanamide, trifluoroacetate The title compound was prepared from 2-t-butoxycarbonylamino-2-methyl-N-[2,3,4,5-tetrahydro-1-[[2'-[2-[[methylaminocarbonyl]amino]ethyl][1,1'-biphenyl]-4-yl]methyl]-2-oxo-1H-benzazepin-3(R)-yl]propanamide (Step G) according to the procedure described in Example 52, Step M. $^1$H NMR (200 MHz, CD$_3$OD): δ 1.53 (s, 3H), 1.62 (s, 3H), 2.25 (m, 2H), 2.59 (m, 5H), 2.67 (t, 7 Hz, 2H), 4.37 (dd; 12, 9 Hz; 1H), 4.96 (d, 15 Hz,1H), 5.21 (d, 15 Hz, 1H), 7.08–7.38 (m, 12H). FAB-MS: calculated for $C_{31}H_{37}N_5O_3$ 527; found 528 (M+H, 100%).

EXAMPLE 54

2-Amino-2-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]propanamide, trifluoroacetate Step A:

2-t-Butoxycarbonylamino-2-methyl-N-[2,3,4,5-tetrahydro-4-oxo-5H-1,5-benzothiazepin-3(S)-yl]propanamide Prepared from 3(S)-amino-2,3,4,5-tetrahydro-1,5-benzothiazepin-4(5H)-one (prepared from D-cysteine (S-cysteine) and 2-fluoro-1-nitrobenzene by the method of Slade, et al, *J. Med. Chem.*, 28, 1517–1521 (1985)) and N-t-butoxycarbonyl-2-methylaniline by the procedure described in Example 1, Step I. $^1$H NMR (200 MHz, CDCl$_3$): δ 1.22 (s, 15H), 2.86 (t, 12 Hz, 1H), 3.85 (dd; 11, 7 Hz; 1H), 4.65 (m, 1H), 4.93 (s, 1H), 7.07 (dd; 8, 6 Hz; 1H), 7.10–7.40 (m, 3H), 7.60 (dd; 8, 6 Hz; 1H), 8.0 (br s, 1H). FAB-MS: calculated for $C_{18}H_{25}N_3O_4S$ 379; found 380 (M+H, 45%).

Step B:

2-t-Butoxycarbonylamino-2-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]propanamide Prepared from 2-t-butoxycarbonylamino-2-methyl-N-[2,3,4,5-tetrahydro-4-oxo-5H-1,5-benzothiazepin-3(S)-yl]propanamide (Step A) and 2'-[[(methylamino)carbonyl]amino]methyl-1,1'-biphenyl-4-methanol, methanesulfonate ester (Example 48, Step I) according to the procedure described in Example 35, Step H. $^1$H NMR (200 MHz, CDCl$_3$): δ 1.34 (s, 15H), 2.60 (d, 5 Hz, 3H), 2.78 (t, 12 Hz, 1H), 3.77 (dd; 11, 7 Hz; 1H), 4.20 (d, 4 Hz, 2H), 4.62 (m, 1H), 4.93 (s, 1H), 4.98 (d, 16 Hz, 1H), 5.15 (d, 16 Hz, 1H), 7.10–7.47 (m, 11H), 7.58 (dd; 8, 6 Hz; 1H). FAB-MS: calculated for $C_{34}H_{41}N_5O_5S$ 631; found 632 (M+H, 20%).

Step C:

2-Amino-2-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]propanamide The title compound was prepared from 2-t-butoxycarbonylamino-2-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]propanamide (Step B) according to the procedure described in Example 52, Step M. $^1$H NMR (200 MHz, CD$_3$OD): δ 1.52 (s, 3H), 1.59 (s, 3H), 2.64 (s, 3H), 3.17 (t, 12 Hz, 1H), 3.56 (dd; 12, 8 Hz; 1H), 4.14 (s, 2H), 4.57 (dd; 12, 8 Hz; 1H), 5.05 (d, 16 Hz, 1H), 5.20 (d, 16 Hz, 1H), 7.08–7.50 (m, 11H), 7.62 (d, 7 Hz; 1H). FAB-MS: calculated for $C_{29}H_{33}N_5O_3S$ 531; found 532 (M+H, 100%).

EXAMPLE 55

2-Amino-2-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]propanamide, trifluoroacetate Step A:

2-t-Butoxycarbonylamino-2-methyl-N-[2,3,4,5-tetrahydro-8-fluoro-4-oxo-5H-1,5-benzothiazepin-3(S)-yl]propanamide Prepared from 3(S)-amino-8-fluoro-2,3,4,5-tetrahydro-1,5-benzothiazepin-4(5H)-one (prepared from D-cysteine (S-cysteine) and 2,4-difluoro-1-nitrobenzene by the method of Slade, et al, *J. Med. Chem.*, 28, 1517–1521 (1985) used for the preparation of 3(S)-amino-2,3,4,5-tetrahydro-1,5-benzothiazepin-4(5H)-one) and N-t-butoxycarbonyl-2-methylaniline by the procedure described in Example 1, Step I. $^1$H NMR (200 MHz, CDCl$_3$): δ 1.42 (s, 15H), 2.90 (t, 12 Hz, 1H), 3.83 (dd; 11, 7 Hz; 1H), 4.63 (m, 1H), 4.97 (s, 1H), 7.04 (m, 2H), 7.31 (m, 2H), 8.33 (s, 1H). FAB-MS: calculated for $C_{18}H_{25}FN_3O_4S$ 397; found 398 (M+H, 45%).

Step B:

2-t-Butoxycarbonylamino-2-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]propanamide Prepared from 2-t-butoxycarbonylamino-2-methyl-N-[2,3,4,5-tetrahydro-8-fluoro-4-oxo-5H-1,5-benzothiazepin-3(S)-yl]-propanamide (Step A) and 2'-[[(methylamino)carbonyl]amino]methyl-1,1'-biphenyl-4-methanol, methanesulfonate ester (Example 48, Step I) according to the procedure described in Example 35, Step H. $^1$H NMR (200 MHz, CDCl$_3$): δ 1.39 (s, 15H), 2.62 (d, 5 Hz, 3H), 2.80 (t, 12 Hz, 1H), 3.75 (dd; 11, 7 Hz; 1H), 4.22 (d, 4 Hz, 2H), 4.48 (m, 1H), 4.68 (m, 1H), 4.92 (s, 1H), 4.96 (d, 16 Hz, 1H), 5.08 (d, 16 Hz, 1H), 7.10–7.47 (m, 11H). FAB-MS: calculated for C$_{34}$H$_{40}$FN$_5$O$_5$S 649; found 650 (M+H, 15%).

Step C:

2-Amino-2-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]propanamide, trifluoroacetate The title compound was prepared from 2-t-butoxycarbonylamino-2-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]propanamide (Step B) according to the procedure described in Example 52, Step M. $^1$H NMR (200 MHz, CD$_3$OD): δ 1.53 (s, 3H), 1.60 (s, 3H), 2.64 (s, 3H), 3.19 (t, 12 Hz, 1H), 3.59 (dd; 12, 8 Hz; 1H), 4.14 (s, 2H), 4.57 (dd; 12, 8 Hz; 1H), 5.00 (d, 16 Hz, 1H), 5.22 (d, 16 Hz, 1H), 7.08–7.43 (m, 10H), 7.59 (dd; 9, 5 Hz; 1H). FAB-MS: calculated for C$_{29}$H$_{32}$FN$_5$O$_3$S 549; found 550 (M+H, 60%).

EXAMPLE 56

2-Amino-2-methyl-N-[7-fluoro-2,3,4,5-tetrahydro-1-[[2'-[[[(methylamino)carbonyl]amino]methyl][1,1'-biphenyl]-4-yl]methyl]-2-oxo-1H-benzazepin-3(R)-yl]propanamide, hydrochloride Step A:

3(R)-amino-7-nitro-2,3,4,5-tetrahydro-1H-1-benzazepin-2-one

To a solution of 440 mg (2.50 mmol) of 3(R)-amino-2,3,4,5-tetrahydro-1H-1-benzazepin-2-one (Example 1, Step E) in 5 mL of concentrated sulfuric acid at 0° C. was added 265 mg (2.63 mmol) of potassium nitrate. The resulting yellow solution was stirred for 30 minutes at then at room temperature for 24 hours. The reaction mixture was poured carefully into 100 g of ice and the pH of the resulting mixture was adjusted to 11 by the portionwise addition of sodium carbonate. The mixture was transferred to a separatory funnel and extracted thoroughly with ethyl acetate (4×100 mL). The organic extracts were combined, washed with brine (100 mL), dried over sodium sulfate and filtered. The solvent was removed under vacuum to afford 385 mg (70%) of the product as a yellow solid. $^1$H NMR (200 MHz, CDCl$_3$): δ 1.58 (s, 2H), 1.98 (m, 1H), 2.47–2.70 (m, 1H), 2.72–3.05 (m, 2H), 3.40 (dd; 11, 8 Hz; 1H), 7.07 (d, 8 Hz, 1H), 7.92 (s, 1H), and 8.10 (m, 1H). FAB-MS: calculated for C$_{10}$H$_{11}$N$_3$O$_3$ 221; found 222 (M+H,100%).

Step B:

2-Benzyloxycarbonylamino-2-methyl-N-[7-nitro-2,3,4,5-tetrahydro-2-oxo-1H-1-benzazepin-3(R)-yl]propanamide Prepared from N-carbobenzyloxy-2-methylalanine and 3(R)-amino-7-nitro-2,3,4,5-tetrahydro-1H-1-benzazepin-2-one (Step A) substituting benzotriazol-1-yloxytripyrrolidinophosphonium hexafluorophosphate for benzotriazol-1-yloxytris(dimethylamino)phosphonium hexafluorophosphate according to the procedure described in Example 1, Step I. $^1$H NMR (400 MHz, CDCl$_3$): δ 1.48 (s, 3H), 1.49 (s, 3H), 2.00 (m, 1H), 2.73 (m, 2H), 2.92 (m, 1H), 4.45 (m, 1H), 5.07 (s, 2H), 5.30 (s, 1H), 7.05 (d, 8 Hz, 1H), 7.30 (m, 6H), 8.06 (dd; 8, 6 Hz; 1H), 8.13 (d, 2.5 Hz, 1H), 8.35 (s, 1H). FAB-MS: calculated for C$_{22}$H$_{24}$N$_4$O$_6$ 424; found 425 (M+H, 100%).

Step C:

2-Benzyloxycarbonylamino-2-methyl-N-[7-amino-2,3,4,5-tetrahydro-2-oxo-1H-1-benzazepin-3(R)-yl]propanamide To a solution of 310 mg (0.73 mmol) 2-benzyloxycarbonylamino-2-methyl-N-[7-nitro-2,3,4,5-tetrahydro-2-oxo-1H-1-benzazepin-3(R)-yl]propanamide (Step B) in 20 mL of methanol was added 78 mg (1.5 mmol) of ammonium chloride followed by 669 mg (10.2 mmol) of zinc dust. The resulting mixture was heated at reflux for four hours. The solids were removed by filtration through Celite. The filter pad was washed with 30 mL of hot methanol. The filtrate was combined and the solvent was removed under vacuum. The residue was dissolved in 10 mL of 1N aqueous hydrochloric acid and the solids were filtered away. To the resulting solution was added sufficient 5N aqueous sodium hydroxide until the pH was approximately 12. The solution was extracted with ethyl acetate (3×50 mL). The combined organic extracts were washed with water then brine, dried over magnesium sulfate and filtered. The solvent was removed under vacuum to afford 256 mg (85%) of the product as a white solid. $^1$H NMR (400 MHz, CDCl$_3$): δ 1.48 (s, 3H), 1.50 (s, 3H), 1.78 (m, 1H), 2.47 (m, 1H), 2.71 (m, 1H), 2.82 (m, 1H), 3.67 (s, 2H), 4.44 (m, 1H), 5.05 (s, 2H), 5.39 (s, 1H), 6.50 (m, 2H), 6.74 (d, 8 Hz, 1H), 7.04 (d, 7 Hz, 1H), 7.32 (m, 6H). FAB-MS: calculated for C$_{22}$H$_{26}$N$_4$O$_4$ 410; found 411 (M+H, 100%).

Step D:

2-Amino-2-methyl-N-[7-fluoro-2,3,4,5-tetrahydro-2-oxo-1H-1-benzazepin-3(R)-yl]-propanamide To a solution of 256 mg (0.624 mmol) of 2-benzyloxycarbonylamino-2-methyl-N-[7-amino-2,3,4,5-tetrahydro-2-oxo-1H-1-benzazepin-3(R)-yl]propanamide (Step C) in 1.2 mL of water was added 0.171 mL of concentrated hydrochloric acid. The resulting mixture was stirred until all the solids were dissolved then the solution was cooled to 0° C. To this solution was added a solution of 52 mg (0.75 mmol) of sodium nitrite in a minimal amount of water. After 30 minutes at 0° C., 0.156 mL (1.06 mmol) of 60 weight percent aqueous hexafluorophosphoric acid was added dropwise. Immediately a white precipitate formed. The solids were filtered and washed with ice cold water, then air dried. The resulting solid was dried under vacuum overnight.

The solid was slurried in 5 mL of mesitylene and the flask equipped with a nitrogen purge was placed in a 165° C. oil bath for 5 minutes. Rapid gas evolution was observed. The mixture was cooled to room temperature and diluted with 100 mL of ethyl acetate. The resulting solution was washed with sodium bicarbonate then brine, dried over magnesium sulfate and the solvent was removed under vacuum. The residue was purified by flash column chromatography on silica gel eluting with chloroform/10% ammonium hydroxide (33%) in methanol to afford 33 mg (23%) of the product as an off-white solid. $^1$H NMR (200 MHz, CDCl$_3$): δ 1.30 (s, 6H), 2.10 (m, 1H), 2.50 (m, 1H), 2.73 (m, 1H), 2.89 (m, 1H) 4.32 (dd; 12, 8 Hz; 1H), 5.05 (s, 3H), 7.05 (m, 3H). FAB-MS: calculated for C$_{14}$H$_{18}$FN$_3$O$_2$ 279; found 280 (M+H, 100%).

Step E:

2-Benzyloxycarbonylamino-2-methyl-N-[7-fluoro-2,3,4,5-tetrahydro-2-oxo-1H-1-benzazepin-3(R)-yl]propanamide To a solution of 33 mg (0.12 mmol) of 2-amino-2-methyl-N-[7-fluoro-2,3,4,5-tetrahydro-2-oxo-1H-1-benzazepin-3(R)-yl]propanamide (Step D) in 1 mL of methylene chloride was 32 mg (0.13 mmol) of N-(benzyloxycarbonyloxy)succinimide. The soution was stirred at room temperature for 24 hours then quenched with 5 drops of 33% aqueous ammonium hydroxide. The solvent was removed under vacuum and the residue was purified by flash column chromatography on silica gel eluting with ethyl acetate/ hexanes (75:25) to afford 25 mg (46%) of the product as an off-white solid. $^1$H NMR (400 MHz, CDCl$_3$): δ 1.48 (s, 3H), 1.50 (s, 3H), 1.82 (m, 1H), 2.56 (m, 1H), 2.71 (m, 1H), 2.86 (m, 1H), 4.42 (m, 1H), 5.05 (s, 2H), 5.43 (s, 1H), 6.90 (m, 2H), 7.09 (d, 8 Hz, 1H), 7.30 (m, 5H), 8.09 (s, 1H). FAB-MS: calculated for C$_{22}$H$_{24}$FN$_3$O$_4$ 413; found 414 (M+H, 100%).

Step F:

2-Benzyloxycarbonylamino-2-methyl-N-[7-fluoro-2,3,4, 5-tetrahydro-2-oxo-1-[[2'-[(t-butoxycarbonylamino) methyl]-[1,1'-biphenyl]-4-yl]methyl]-1H-benzazepin-3(R)-yl]-propanamide Prepared from 2-benzyloxycarbonylamino-2-methyl-N-[7-fluoro-2,3,4,5-tetrahydro-2-oxo-1H-1-benzazepin-3(R)-yl]propanamide (Step E) and 2'-[(t-butoxycarbonylamino) methyl]-1,1'-biphenyl-4-methanol, methanesulfonate ester (Example 35, Step G) according to the procedure described in Example 35, Step H. $^1$H NMR (200 MHz, CDCl$_3$): δ 1.39 (s, 9H), 1.48 (s, 3H), 1.51 (s, 3H), 1.78 (m, 1H), 2.35–2.70 (m, 3H), 4.18 (d, 7 Hz, 2H), 4.42 (m, 1H), 4.58 (m, 1H), 4.75 (d, 16 Hz, 1H), 5.05 (s, 2H), 5.27 (d, 16 Hz, 1H), 5.35 (s, 1H), 6.88 (dd; 8, 6 Hz; 1H), 6.98 (m, 1H), 7.09 (d, 6 Hz,1 H), 7.14–7.35 (m, 13H), 7.40 (d, 8HZ, 1H). FAB-MS: calculated for C$_{41}$H$_{45}$FN$_4$O$_6$ 708; found 709 (M+H).

Step G:

2-Benzyloxycarbonylamino-2-methyl-N-[7-fluoro-2,3,4, 5-tetrahydro-2-oxo-1-[[2'-(aminomethyl)[1,1'-biphenyl]-4-yl]methyl]-1H-benzazepin-3(R)-yl]propanamide, trifluoroacetate Prepared from 2-benzyloxycarbonylamino-2-methyl-N-[7-fluoro-2,3,4,5-tetrahydro-2-oxo-1-[[2'-[(t-butoxycarbonylamino)methyl][1,1'-biphenyl]-4-yl]methyl]-1H-benzazepin-3(R)-yl]propanamide (Step F) according to the procedure described in Example 36, Step A. $^1$H NMR (200 MHz, CDCl$_3$): δ 1.40 (s, 6H), 1.90 (m, 1H), 2.25–2.65 (m, 3H), 4.05 (s, 2H), 4.35 (m, 1H), 4.78 (d, 16 Hz, 1H), 4.96 (s, 2H), 5.05 (d, 16 Hz, 1H), 5.55 (s, 1H), 6.90 (m, 3H), 7.00–7.50 (m, 17H), 7.80 (s, 1H). FAB-MS: calculated for C$_{36}$H$_{37}$FN$_4$O$_4$ 608; found 609 (M+H, 100%).

Step H:

2-Benzyloxycarbonylamino-2-methyl-N-[7-fluoro-2,3,4, 5-tetrahydro-1-[[2'-[[[(methylamino)carbonyl]amino] methyl]-[1,1'-biphenyl]-4-yl]methyl]-2-oxo-1H-benzazepin-3(R)-yl]propanamide Prepared from 2-benzyloxycarbonylamino-2-methyl-N-[7-fluoro-2,3,4,5-tetrahydro-2-oxo-1-[[2'-(aminomethyl) [1,1'-biphenyl ]-4-yl]methyl]-1H-benzazepin-3(R)-yl] propanamide, trifluoroacetate (Step G) and methyl isocyanate according to the procedure described in Example 35, Step I. $^1$H NMR (400 MHz, CDCl$_3$): δ 1.44 (s, 3H), 1.45 (s, 3H), 1.78 (m, 1H), 1.85 (s, 1H), 2.30–2.60 (m,3H), 2.57 (d, 4 Hz, 3H), 4.18 (d, 5 Hz, 2H), 4.40 (m, 1H), 4.62 (m, 1H), 4.80 (m, 2H), 5.00 (s, 2H), 5.17 (d, 15 Hz, 1H), 540 (s, 1H), 6.85 (m, 1H), 6.96 (m, 1H), 7.08–7.35 (m, 13H), 7.39 (m, 1H). FAB-MS: calculated for C$_{38}$H$_{40}$FN$_5$O$_5$ 665; found 666 (M+H, 100%).

Step I:

2-Amino-2-methyl-N-[7-fluoro-2,3,4,5-tetrahydro-1-[[2'-[[[[(methylamino)carbonyl]amino]methyl][1,1'-biphenyl]-4-yl]methyl]-2-oxo-1H-benzazepin-3(R)-yl]propanamide, trifluoroacetate 2-Benzyloxycarbonylamino-2-methyl-N-[7-fluoro-2,3,4, 5-tetrahydro-1-[[2'-[[[(methylamino)carbonyl]-amino] methyl][1,1'-biphenyl]-4-yl]methyl]-2-oxo-1H-benzazepin-3(R)-yl]propanamide (30 mg, 0.045 mmol) (Step H) was dissolved in 1 mL of 30% hydrobromic acid in acetic acid. The mixture was stirred at room temperature for 1 hour. The solvent was removed under vacuum to give a solid which was purified by reverse phase medium pressure liquid chromatography on C-8 eluting with methanol/0.1% aqueous trifluoroacetic acid (60:40) to afford 27 mg (93%) of the title compound as an off-white solid. $^1$H NMR (400 MHz, CD$_3$OD): δ 1.55 (s, 3H), 1.64 (s, 3H), 2.28 (m, 2H), 2.62 (m, 2H), 2.67 (s, 3H), 4.16 (s, 2H), 4.39 (dd; 12, 8 Hz; 1H), 4.96 (d, 15 Hz, 1H), 5.25 (d, 15 Hz, 1H), 7.01–7.19 (m, 3H), 7.20–7.39 (m, 6H), 7.40 (m, 2H). FAB-MS: calculated for C$_{30}$H$_{34}$FN$_5$O$_3$ 531; found 532 (M+H, 100%).

EXAMPLE 57

3-[2(R)-Hydroxypropyl]amino-3-methyl-N-[2,3,4,5-tetrahydro-5-[[2'-[[[(methylamino)carbonyl]amino] methyl][1,1'-biphenyl]-4-yl]methyl]4-oxo-1,5-benzothiazepin-3(S)-yl]butanamide Step A:

3-[2(R)-Benzyloxypropyl]amino-3-methyl-N-[2,3,4,5-tetrahydro-5-[[2'-[[[(methylamino)carbonyl]amino]methyl] [1,1'-biphenyl]-4-yl]methyl]-4-oxo-1,5-benzothiazepin-3 (S)-yl]butanamide Prepared from 2-amino-2-methyl-N-[2,3,4,5-tetrahydro-5-[[2 '-[[[(methylamino)carbonyl]amino]methyl][1,1'-biphenyl]-4-yl]methyl]-4-oxo-1,5-benzothiazepin-3(S)-yl] propanamide, trifluoroacetate (Example 54) and (R)-2-benzyloxypropanal (prepared from methyl D-lactate according to the procedure of Hanessian and Kloss, *Tetrahedron Lett.*, 26, 1261–1264 (1985) according to the procedure described in Example 49, Step B.

Step B:

3-[2(R)-Hydroxypropyl]amino-3-methyl-N-[2,3,4,5-tetrahydro-5-[[2'-[[[(methylamino)carbonyl]amino]methyl] [1,1'-biphenyl]-4-yl]methyl]-4-oxo-1,5-benzothiazepin-3 (S)-yl]butanamide The title compound is prepared from 3-[2(R)-benzyloxypropyl]amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl] butanamide (Step A) by the procedure described in Example 49, Step E.

EXAMPLE 58

3-[2(S),3-Dihydroxypropyl]amino-3-methyl-N-[2,3, 4,5-tetrahydro-5-[[2'-[[[(methylamino)carbonyl] amino]methyl][1,1'-biphenyl]-4-yl]-methyl]-4-oxo-1,5-benzothiazepin-3(S)-yl]butanamide Step A:

3-[[2,2-Dimethyl-1,3-dioxolan-4(S)-yl]methyl]amino-3-methyl-N-[2,3,4,5-tetrahydro-5-[[2'-[[[(methylamino) carbonyl]amino]methyl][1,1'-biphenyl]-4-yl]methyl]-4-oxo-1,5-benzothiazepin-3(S)-yl]butanamide Prepared from 2-amino-2-methyl-N-[2,3,4,5-tetrahydro-5-[[2'-[[[(methylamino)carbonyl]amino ]methyl][1,1'-biphenyl]-4-yl]-methyl]-4-oxo-1,5-benzothiazepin-3(S)-yl] propanamide, trifluoroacetate (Example 54) and D-glyceraldehyde acetonide (used crude as prepared according to the procedure of Hertel, L. W.; Grossman, C. S.; Kroin, J. S. *Syn. Comm.*, 1991, 21, 151–154) by the procedure described in Example 50, Step B.

Step B:

3-[2(S),3-Dihydroxypropyl]amino-3-methyl-N-[2,3,4,5-tetrahydro-5-[[2'-[[[(methylamino)carbonyl]amino]methyl] [1,1'-biphenyl]-4-yl]methyl]-4-oxo-1,5-benzothiazepin-3 (S)-yl]butanamide The title compound is prepared from 3-[[2,2-dimethyl-1, 3-dioxolan-4(S)-yl]methyl]amino-3-methyl-N-[2,3,4,5- tetrahydro-5-[[2'-[[[(methylamino)carbonyl]amino]methyl][1,1'-biphenyl]-4-yl]methyl]-4-oxo-1,5-benzothiazepin-3(S)-yl]butanamide (Step A) by the procedure described in Example 50, Step D.

EXAMPLE 59

2-Amino-2-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]propanamide, trifluoroacetate Step A:
3(R)-t-Butoxycarbonylamino-2,3,4,5-tetrahydro-1H-1-benzazepin-2-one To a suspension of 576 mg (3.27 mmol) of 3(R)-amino-2,3,4,5-tetrahydro-1H-1-benzazepin-2-one (Example 1, Step B) in 5 mL methylene chloride at room temperature was added 0.46 mL (334 mg, 3.3 mmol, 1.0 eq.) of triethylamine followed by 0.75 mL (712 mg, 3.27 mmol, 1.1 eq) of di-t-butyldicarbonate. The mixture was stirred for 4 hours at room temperature then added to 50 mL of ethyl acetate and washed with 5% aqueous citric acid (3x), saturated aqueous sodium bicarbonate and saturated aqueous sodium chloride. The organic layer was removed, dried over magnesium sulfate, filtered and solvents removed under vacuum to give 884 mg (3.20 mmol, 98%) of th product as a white solid. $^1$H NMR (200 MHz, CDCl$_3$): δ 1.40 (s, 9H), 2.00 (m, 1H), 2.65 (m, 2H), 2.95 (m, 1H), 4.29 (m, 1H), 5.42 (br d, 8 Hz, 1H), 6.97 (d, 7 Hz, 1H), 7.2 (m, 3H), 7.50 (br s, 1H).

Step B:
3(R)-t-Butoxycarbonylamino-2,3,4,5-tetrahydro-1-[[2'-cyano[1,1'-biphenyl]-4-yl]methyl]-1H-benzazepin-2-one Prepared from 4'-bromomethyl-1,1'-biphenyl-2-nitrile (prepared by the method of M. Fisher, et al, U.S. Pat. No. 5,206,235) and 3(R)-t-butoxycarbonylamino-2,3,4,5-tetrahydro-1H-1-benzazepin-2-one (Step A) by the procedure described in Example 1, Step Q. $^1$H NMR (400 MHz, CDCl$_3$): δ 1.39 (s, 9H), 1.90 (m, 1H), 2.40–2.60 (m, 3H), 4.28 (m, 1H), 4.94 (d, 15 Hz, 1H), 5.20 (d, 15 Hz, 1H), 5.43 (d, 7 Hz, 1H), 7.1–7.3 (m, 4H), 7.33 (d, 8 Hz, 2H), 7.35–7.50 (m, 4H), 7.60 (t, 8 Hz, 1H), 7.72 (d, 8 Hz, 1H). FAB-MS: calculated for C$_{29}$H$_{29}$N$_3$O$_3$ 467; found 468 (M+H, 15%), 368 (M−BOC, 100%).

Step C:
3(R)-t-Butoxycarbonylamino-2,3,4,5-tetrahydro-1-[[2'-aminomethyl[1,1'-biphenyl]-4-yl]methyl]-1H-benzazepin-2-one To a solution of 200 mg (0.43 mmol) of the intermediate obtained in Step B in 5 mL of ethanol was added 5 mL of liquid ammonia and the resulting mixture hydrogenated at 200–400 psi and 80° C. for 6 hours over 60 mg of Raney nickel. The reaction mixture was cautiously vented and all volatiles removed by a steady stream of nitrogen. The residue was redissolved in chloroform, filtered through Celite and the filtrate concentrated under vacuum to give 149 mg (0.32 mmol, 74%) of the product as a white foam which was used without purification.

Step D:
3(R)-t-Butoxycarbonylamino-2,3,4,5-tetrahydro-1-[[2'-[[(methoxycarbonyl)amino]methyl][1,1'-biphenyl]-4-yl]methyl]-1H-benzazepin-2-one A solution of 31 mg (0.066 mmol) of the intermediate obtained in Step C in 1 mL of methylene chloride at room temperature was treated with 1 drop of triethylamine followed by 5 μL (6 mg, 0.067 mmol, 1 eq.) of methyl chloroformate. The mixture was stirred at room temperature for 1 hour then diluted into 10 mL of ethyl acetate and washed with 5% aqueous citric acid and saturated aqueous sodium chloride. The organic layer was removed, dried over magnesium sulfate, filtered and solvents removed under vacuum. The residue was purified by medium pressure liquid chromatography on silica, eluting with 5% methanol in ethyl acetate, to give 33 mg (0.062 mmol, 95%) of the product as a colorless glass. H NMR (400 MHz, CDCl$_3$): δ 1.38 (s, 9H), 1.91 (m, 1H), 2.43–2.60 (m, 3H), 3.62 (s, 3H), 4.26 (m, 3H), 4.68 (br t, 1H), 4.93 (d, 15 Hz, 1H), 5.18 (d, 15 Hz, 1H), 5.45 (br d, 7 Hz, 1H), 7.13–7.35 (m, 11H), 7.41 (d, 8 Hz, 1H). FAB-MS: calculated for C$_{31}$H$_{35}$N$_3$O$_5$ 529; found 530 (M+H, 25%), 430 (M−BOC, 100%).

Step E:
2-t-Butoxycarbonylamino-2-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]propanamide A solution of 33 mg (0.062 mmol) of the intermediate obtained in Step D in 2 mL of methanol at room temperature was treated with 0.5 mL of concentrated hydrochloric acid. After 2 hours, solvents were removed under vacuum and the residue further dried under high vacuum for 1 hour.

The amine hydrochloride obtained above was taken up in 1 mL of methylene chloride and treated with 13 mg (0.064 mmol, 1.03 eq.) of N-t-butoxycarbonyl-α-methylalanine, 26 μL of triethylamine (19 mg, 0.19 mmol, 3 eq.) and finally, 49 mg (0.094 mmol, 1.5 eq.) of benzotriazol-1-yloxytripyrrolidinophosphonium hexafluorophosphate. After stirring at room temperature for 1 hour, the reaction mixture was diluted into 10 mL of ethyl actetate and washed with 5% aqueous citric acid, saturated aqueous sodium bicarbonate and saturated aqueous sodium chloride. The organic layer was removed, dried over magnesium sulfate, filtered and solvents removed under vacuum. The residue was purified by medium pressure liquid chromatography on silica, eluting with ethyl acetate, to give 37 mg (0.060 mmol, 96%) of the product as a clear glass. $^1$H NMR (400 MHz, CDCl$_3$): δ 1.41 (s, 9H), 1.42 (s, 3H), 1.44 (s, 3H), 1.84 (m, 1H), 2.40–2.65 (m, 3H), 3.61 (s, 3H), 4.24 (d, 6 Hz, 2H), 4.48 (m, 1H), 4.68 (br t, 1H), 4.89 (d, 15 Hz, 1H), 4.91 (br s, 1H), 5.20 (d, 15 Hz, 1H), 7.15–7.35 (m, 11H), 7.40 (d, 8 Hz, 1H). FAB-MS: calculated for C$_{35}$H$_{42}$N$_4$O$_6$ 614; found 615 (M+H, 5%), 515 (M−BOC, 100%).

Step F:
2-Amino-2-methyl-N-[2,3,4,5-tetrahydro-1-[[2'-[[(methoxycarbonyl)amino]methyl][1,1'-biphenyl]-4-yl]methyl]-2-oxo-1H-benzazepin-3(R)-yl]propanamide, trifluoroacetate A solution of 35 mg (0.057 mmol) of the intermediate obtained in Step E in 1 mL of methanol at room temperature was treated with 0.5 mL of concentrated hydrochloric acid. After 3 hours, solvents were removed under vacuum and the residue purified by medium pressure liquid chromatography on C8, eluting with methanol/0.1% aqueous trifluoroacetic acid (65:35), to give 35 mg (0.055 mmol, 98%) of the title compound as a colorless glass. $^1$H NMR (400 MHz, CD$_3$OD): δ 1.55 (s, 3H), 1.64 (s, 3H), 2.27 (m, 2H), 2.61 (m, 2H), 3.60 (s, 3H), 4.14 (s, 2H), 4.40 (m, 1H), 5.02 (d, 15 Hz, 1H), 5.22 (d, 15 Hz, 1H), 7.14 (d, 8 Hz, 1H), 7.20–7.40 (m, 11H), 8.22 (br d, 8 Hz, 1H). FAB-MS: calculated for $C_{30}H_{34}N_4O_4$ 514; found 515 (M+H, 55%).

EXAMPLE 60

2-Amino-2-methyl-N-[2,3,4,5-tetrahydro-1-[[2'-[[(benzyloxycarbonyl)amino]methyl][1,1'-biphenyl]-4-yl]methyl]-2-oxo-1H-benzazepin-3(R)-yl] propanamide, trifluoroacetate Step A:

3(R)-t-Butoxycarbonylamino-2,3,4,5-tetrahydro-1-[[2'-[[(benzyloxycarbonyl)amino]methyl][1,1'-biphenyl]-4-yl]methyl]-1H-benzazepin-2-one A solution of 64 mg (0.14 mmol) of 3(R)-t-butoxycarbonylamino-2,3,4,5-tetrahydro-1-[[2'-aminomethyl[1,1'-biphenyl]-4-yl]methyl]-1H-benzazepin-2-one (Example 59, Step C) in 1 mL of methylene chloride at room temperature was treated with 1 drop of triethylamine followed by 36 mg (0.14 mmol, 1 eq.) of N-(benzyloxycarbonyloxy)succinimide and 5 mg of N-hydroxybenzotriazole. The mixture was stirred at room temperature for 1 hour then added to 10 mL of ethyl acetate and washed with 5% aqueous citric acid, saturated aqueous sodium bicarbonate and saturated aqueous sodium chloride. The organic layer was removed, dried over magnesium sulfate, filtered and solvents removed under vacuum. The residue was purified by medium pressure liquid chromatography on silica, eluting with ethyl acetate/hexanes (2:1), to give 68 mg (0.11 mmol, 83%) of the product as a white, crusty foam. $^1$H NMR (400 MHz, CDCl$_3$): δ 1.38 (s, 9H), 1.89 (m, 1H), 2.40–2.60 (m, 3H), 4.27 (m, 3H), 4.75 (br t, 1H), 4.92 (d, 15 Hz, 1H), 5.05 (s, 2H), 5.18 (d, 15 Hz, 1H), 5.44 (br d, 7 Hz, 1H), 7.10–7.35 (m, 11H), 7.40 (d, 8 Hz, 1H). FAB-MS: calculated for $C_{37}H_{39}N_3O_5$ 605; found 606 (M+H, 2%), 506 (M-BOC, 100%).

Step B:

2-t-Butoxycarbonylamino-2-methyl-N-[2,3,4,5-tetrahydro-1-[[2'-[[(benzyloxycarbonyl)amino]methyl][1,1'-biphenyl]-4-yl]methyl]-2-oxo-1H-benzazepin-3(R)-yl] propanamide Prepared from the intermediate obtained in Step A and N-t-butoxycarbonyl-x-methylalanine by the procedure described in Example 59, Step E. $^1$H NMR (400 MHz, CDCl$_3$): δ 1.41 (s, 9H), 1.42 (s, 3H), 1.44 (s, 3H), 1.82 (m, 1H), 2.38–2.65 (m, 3H), 4.27 (d, 6 Hz, 2H), 4.47 (m, 1H), 4.74 (br t, 1H), 4.87 (d, 15 Hz, 1H), 4.92 (br s, 1H), 5.05 (s, 2H), 5.21 (d, 15 Hz, 1H), 7.10–7.35 (m, 11H), 7.40 (d, 8 Hz, 1H). FAB-MS: calculated for $C_{41}H_{46}N_4O_6$ 690; found 691 (M+H, 3%), 591 (M-BOC, 100%).

Step C:

2-Amino-2-methyl-N-[2,3,4,5-tetrahydro-1-[[2'-[[(benzyloxycarbonyl)amino]methyl][1,1'-biphenyl]-4-yl]methyl]-2-oxo-1H-benzazepin-3(R)-yl]propanamide, trifluoroacetate The title compound was prepared from the intermediate obtained in Step B by the procedure described in Example 59, Step F. $^1$H NMR (400 MHz, CD$_3$OD): δ 1.54 (s, 3H), 1.64 (s, 3H), 2.27 (m, 2H), 2.60 (m, 2H), 4.16 (s, 2H), 4.39 (dd; 7, 11 Hz; 1H), 5.00 (d, 15 Hz, 1H), 5.05 (s, 2H), 5.22 (d, 15 Hz, 1H), 7.14 (d, 8 Hz, 1H), 7.20–7.40 (m, 11H). FAB-MS: calculated for $C_{36}H_{38}N_4O_4$ 590; found 591 (M+H, 100%).

EXAMPLE 61

Utilizing the procedures described in Examples 1 to 60 and general methods of organic synthesis described in the chemical literature and familiar to one skilled in the art, the following compounds of Formula 1 can be prepared from the appropriately substituted starting materials and reagents.

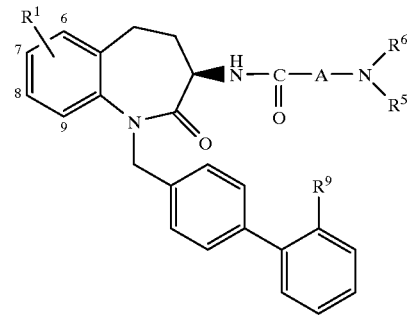

| $R^1$ | $R^9$ | A | $R^4$ | | $R^5$ |
|---|---|---|---|---|---|
| H | H | —NH—C(=O)—NHCH$_3$ | —CH$_2$—C(CH$_3$)(CH$_3$)— | —CH$_2$—CH(OH)—CH(OH)—CH$_2$OH | H |
| H | H | —NH—C(=O)—NHCH$_3$ | —CH$_2$—C(CH$_3$)(CH$_3$)— | —CH$_2$CH$_2$OH | H |
| H | H | —NH—C(=O)—NHCH$_3$ | —CH$_2$—C(CH$_3$)(CH$_3$)— | —CH$_2$C(CH$_3$)$_2$OH | H |

-continued

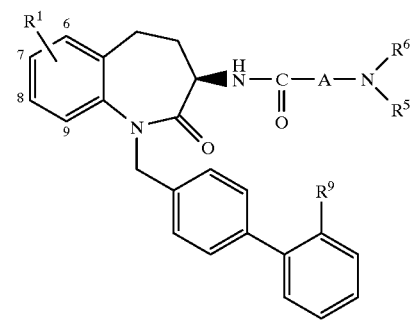

| R[1] | R[9] | A | R[4] | R[5] |
|---|---|---|---|---|
| H | —NH—C(=O)—NHCH₃ | —CH₂—C(CH₃)(CH₃)— | —CH₂CH₂CH(OH)CH₃ | H |
| H | —NH—C(=O)—NHCH₃ | —CH₂—C(CH₃)(CH₃)— | —CH₂—C₆H₅ | H |
| H | —NH—C(=O)—NHCH₃ | —CH₂—C(CH₃)(CH₃)— | —CH₂CH₂CH₃ | H |
| H | —NH—C(=O)—NHCH₃ | —CH₂—C(CH₃)(CH₃)— | —CH₂—CH(OH)—CH₃ | H |
| 6-F | —NH—C(=O)—NHCH₃ | —CH₂—C(CH₃)(CH₃)— | H | H |
| 7-F | —NH—C(=O)—NHCH₃ | —CH₂—C(CH₃)(CH₃)— | H | H |
| 7-CF₃ | —NH—C(=O)—NHCH₃ | —CH₂—C(CH₃)(CH₃)— | H | H |
| 7-OCH₃ | —NH—C(=O)—NHCH₃ | —CH₂—C(CH₃)(CH₃)— | H | H |
| 7-OH | —NH—C(=O)—NHCH₃ | —CH₂—C(CH₃)(CH₃)— | H | H |
| 7-SCH₃ | —NH—C(=O)—NHCH₃ | —CH₂—C(CH₃)(CH₃)— | H | H |
| 7-S(O)CH₃ | —NH—C(=O)—NHCH₃ | —CH₂—C(CH₃)(CH₃)— | H | H |
| 8-OCH₃ | —NH—C(=O)—NHCH₃ | —CH₂—C(CH₃)(CH₃)— | H | H |

-continued

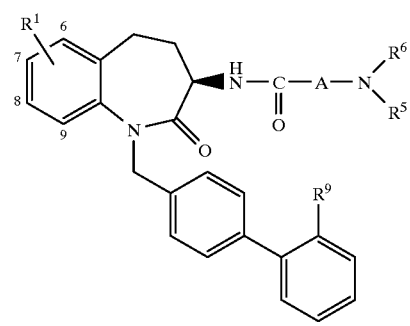

| R¹ | R⁹ | A | R⁴ | R⁵ |
|---|---|---|---|---|
| 8-F | —NH—C(=O)—NHCH₃ | —CH₂—C(CH₃)₂— | H | H |
| 8-Cl | —NH—C(=O)—NHCH₃ | —CH₂—C(CH₃)₂— | H | H |
| 8-I | —NH—C(=O)—NHCH₃ | —CH₂—C(CH₃)₂— | H | H |
| H | —NH—C(=O)—NHCH₃ | —C(CH₃)₂— | H | H |
| H | —NH—C(=O)—NHCH₃ | —C(H)(CH₃)— (R) | H | H |
| H | —NH—C(=O)—NHCH₃ | —C(CH₃)(H)— (S) | H | H |
| H | —NH—C(=O)—NHCH₃ | —C(H)(CH₂OH)— | H | H |
| H | —NH—C(=O)—NHCH₃ | —C(CH₃)(CH₂OH)— | H | H |
| H | —NH—C(=O)—NHCH₃ | —C(H)(CH₃)— | CH₃ | H |
| H | —NH—C(=O)—NHCH₃ | —CH₂—C(CH₃)(CH₂OH)— | H | H |
| H | —NH—C(=O)—NHCH₃ | —CH₂—C(HOCH₂)(CH₃)— | H | H |
| H | —NH—C(=O)—NHCH₃ | —CH₂—C(HOCH₂)(CH₃)— | —CH₂CH(OH)CH₃ | H |
| H | —NH—C(=O)—NHCH₃ | —CH₂—C(HOCH₂)(CH₃)— | —CH₂CH(OH)CH₂OH | H |

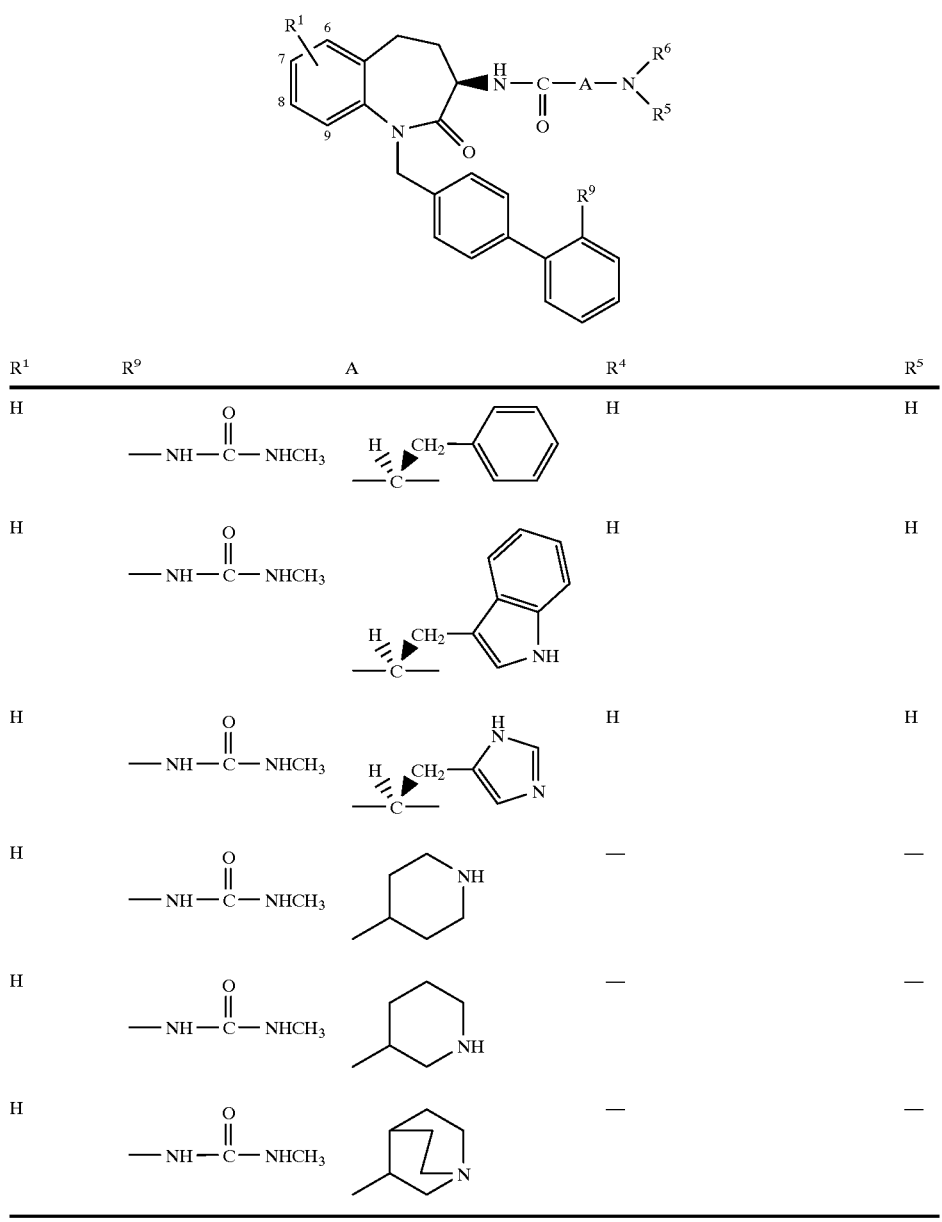
EXAMPLE 62
Utilizing the procedures described in Examples 1 to 60 and general methods of organic synthesis described in the chemical literature and familiar to one skilled in the art, the following compounds of Formula I can be prepared from the appropriately substituted starting materials and reagents.

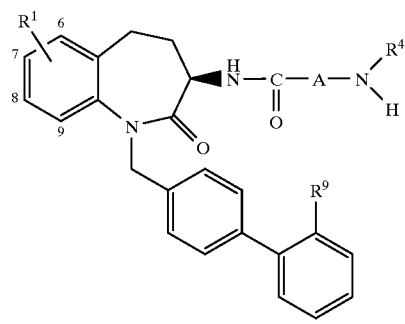

| R¹ | R⁹ | A | R⁴ |
|---|---|---|---|
| H | —NH—C(=O)—NH₂ | —CH₂—C(CH₃)₂— | H |
| H | —NH—C(=O)—NH₂ | —C(CH₃)₂— | H |
| H | —NH—C(=O)—NH₂ | —CH₂—C(CH₃)₂— | —CH₂CH(OH)CH₃ |
| H | —NH—C(=O)—NHCH₃ | —CH₂—C(CH₃)₂— | —CH₂CH(OH)CH₃ |
| H | —NH—C(=O)—NHCH₂CH₂OH | —CH₂—C(CH₃)₂— | —CH₂CH₂CH(OH)CH₃ |
| H | —NH—C(=O)—NHCH₃ | —CH₂—C(CH₃)₂— | —CH₂CH(OH)CH₃ |
| H | —NH—C(=O)—NHCH₃ | —CH₂—C(CH₃)₂— | —CH₂CH(F)CH₃ |
| 7-F | —NH—C(=O)—NHCH₃ | —CH₂—C(CH₃)₂— | —CH₂CH(OH)CH₃ |
| 7-CF₃ | —NH—C(=O)—NHCH₃ | —CH₂—C(CH₃)₂— | —CH₂CH(OH)CH₃ |
| 7-OCH₃ | —NH—C(=O)—NHCH₃ | —CH₂—C(CH₃)₂— | —CH₂CH(OH)CH₃ |
| 7-SCH₃ | —NH—C(=O)—NHCH₃ | —CH₂—C(CH₃)₂— | —CH₂CH(OH)CH₃ |
| 7-F | —NH—C(=O)—NHCH₃ | —CH(CH₃)— | H |
| 7-F | —NH—C(=O)—NHCH₃ | —CH₂—C(H)(CH₂OH)— | H |

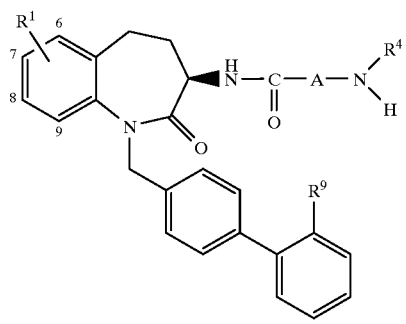

| R₁ | R⁹ | A | R⁴ |
|---|---|---|---|
| 7-F | —NH—C(=O)—NHCH₃ | —CH₂—C(CH₃)≡(CH₂OH)— | H |
| 7-F | —NH—C(=O)—NHCH₃ | —CH₂—C(HOCH₂)≡(CH₃)— | H |
| 7-F | —NH—C(=O)—NHCH₃ | —CH₂—C(HOCH₂)≡(CH₃)— | —CH₂CH(OH)CH₃ |
| 7-CF₃ | —NH—C(=O)—NHCH₃ | —CH₂—C(HOCH₂)≡(CH₃)— | —CH₂CH(OH)CH₂OH |
| 6-F | —NH—C(=O)—NHCH₃ | —CH₂—C(HOCH₂)≡(CH₃)— | —CH₂CH₂CH(OH)CH₃ |

EXAMPLE 63

Utilizing the procedures described in Examples 1 to 60 and general methods of organic synthesis described in the chemical literature and familiar to one skilled in the art, the following compounds of Formula I can be prepared from the appropriately substituted starting materials and reagents.

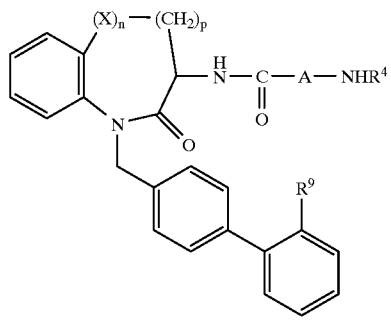

| X | n | p | R⁹ | A | R⁴ |
|---|---|---|---|---|---|
| — | 0 | 3 | —NH—C(=O)—NHCH₃ | —CH₂—C(CH₃)≡(CH₃)— | H |
| — | 0 | 3 | —NH—C(=O)—NHCH₃ | —CH₂—C(CH₃)≡(CH₃)— | —CH₂CH(OH)CH₃ |

-continued

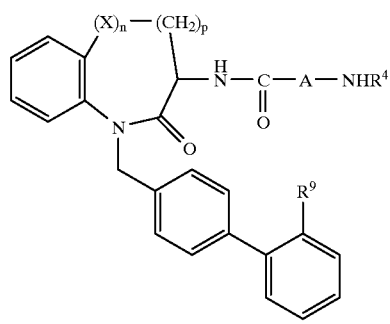

| X | n | p | R⁹ | A | R⁴ |
|---|---|---|---|---|---|
| — | 0 | 1 | —NH—C(=O)—NHCH₃ | —CH₂—C(CH₃)(CH₃)— | H |
| — | 0 | 1 | —NH—C(=O)—NHCH₃ | —CH₂—C(CH₃)(CH₃)— | —CH₂CH(OH)CH₃ |
| — | 0 | 0 | —NH—C(=O)—NHCH₃ | —CH₂—C(CH₃)(CH₃)— | H |
| — | 0 | 0 | —NH—C(=O)—NHCH₃ | —CH₂—C(CH₃)(CH₃)— | —CH₂CH(OH)CH₃ |
| C=O | 1 | 1 | —NH—C(=O)—NHCH₃ | —CH₂—C(CH₃)(CH₃)— | —CH₂CH(OH)CH₃ |
| CHOH | 1 | 1 | —NH—C(=O)—NHCH₃ | —CH₂—C(CH₃)(CH₃)— | —CH₂CH(OH)CH₃ |
| S | 1 | 0 | —NH—C(=O)—NHCH₃ | —CH₂—C(CH₃)(CH₃)— | H |
| S | 1 | 0 | —NH—C(=O)—NHCH₂CH₂OH | —CH₂—C(CH₃)(CH₃)— | H |
| S | 1 | 0 | —NH—C(=O)—NHCH₃ | —CH₂—C(CH₃)(CH₃)— | —CH₂CH(OH)CH₃ |
| SO | 1 | 0 | —NH—C(=O)—NHCH₃ | —CH₂—C(CH₃)(CH₃)— | H |
| SO | 1 | 0 | —NH—C(=O)—NHCH₃ | —C(CH₃)(CH₃)— | H |
| SO | 1 | 0 | —NH—C(=O)—NHCH₃ | —CH₂—C(CH₃)(CH₃)— | —CH₂CH(OH)CH₃ |

-continued

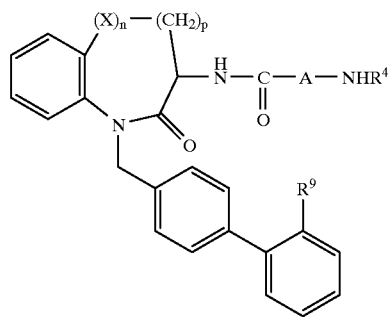

| X | n | p | R⁹ | A | R⁴ |
|---|---|---|---|---|---|
| SO | 1 | 0 | —NH—C(=O)—NHCH₃ | —CH₂—C(CH₃)(CH₃)— | —CH₂CH(OH)CH₂OH |
| S | 1 | 2 | —NH—C(=O)—NHCH₃ | —CH₂—C(CH₃)(CH₃)— | H |
| S | 1 | 2 | —NH—C(=O)—NHCH₃ | —C(CH₃)(CH₃)— | H |
| S | 1 | 2 | —NH—C(=O)—NHCH₃ | —CH₂—C(CH₃)(CH₃)— | —CH₂CH(OH)CH₃ |
| S | 1 | 2 | —NH—C(=O)—NHCH₃ | —CH₂—C(CH₃)(CH₃)— | —CH₂CH(OH)CH₂OH |
| S | 1 | 2 | —NH—C(=O)—NHCH₃ | —CH₂—C(CH₃)(CH₃)— | H |
| S | 1 | 2 | —NH—C(=O)—NHCH₃ | —C(CH₃)(CH₃)— | H |
| S | 1 | 2 | —NH—C(=O)—NHCH₃ | —CH₂—C(CH₃)(CH₃)— | —CH₂CH(OH)CH₃ |
| S | 1 | 2 | —NH—C(=O)—NHCH₃ | —CH₂—C(CH₃)(CH₃)— | —CH₂CH(OH)CH₂OH |
| O | 1 | 1 | —NH—C(=O)—NHCH₃ | —CH₂—C(CH₃)(CH₃)— | H |
| O | 1 | 1 | —NH—C(=O)—NHCH₃ | —C(CH₃)(CH₃)— | H |
| O | 1 | 1 | —NH—C(=O)—NHCH₃ | —CH₂—C(CH₃)(CH₃)— | —CH₂CH(OH)CH₃ |
| O | 1 | 1 | —NH—C(=O)—NHCH₃ | —CH₂—C(CH₃)(CH₃)— | —CH₂CH(OH)CH₂OH |

EXAMPLE 64

Utilizing the procedures described in Examples 1 to 60 and general methods of organic synthesis described in the chemical literature and familiar to one skilled in the art, the following compounds of Formula I can be prepared from the appropriately substituted starting materials and reagents.

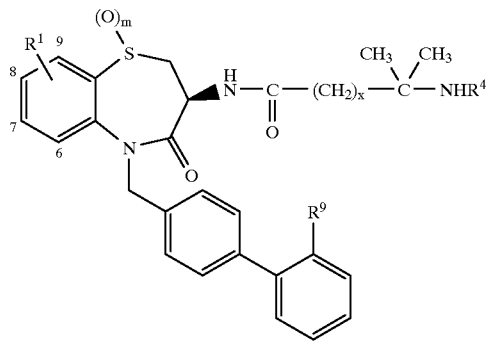

| $R^1$ | X | m | $R^9$ | $R^4$ |
|---|---|---|---|---|
| H | 1 | 0 | —NH—C(=O)—NHCH$_3$ | —CH$_2$CH(OH)CH$_3$ |
| H | 1 | 0 | —NH—C(=O)—NHCH$_3$ | —CH$_2$CH(OH)CH$_3$ |
| H | 1 | 0 | —NH—C(=O)—NHCH$_3$ | —CH$_2$CH(OH)CH$_2$OH |
| H | 0 | 0 | —NH—C(=O)—NHCH$_3$ | H |
| H | 0 | 0 | —NH—C(=O)—NHCH$_3$ | —CH$_2$CH$_2$CH(OH)CH$_3$ |
| H | 1 | 1 | —NH—C(=O)—NHCH$_3$ | —CH$_2$CH(OH)CH$_3$ |
| H | 1 | 1 | —NH—C(=O)—NHCH$_3$ | —CH$_2$CH(OH)CH$_2$OH |
| H | 1 | 1 | —NH—C(=O)—NHCH$_3$ | —CH$_2$CH(OH)CH$_3$ |
| H | 1 | 1 | —NH—C(=O)—NHCH$_3$ | —CH$_2$CH$_2$CH(OH)CH$_3$ |
| H | 1 | 0 | —NH—C(=O)—NHCH$_3$ | —CH$_2$CH(OCH$_3$)CH$_3$ |
| 8-F | 1 | 0 | —NH—C(=O)—NHCH$_3$ | —CH$_2$CH(OH)CH$_3$ |
| 8-CF$_3$ | 1 | 0 | —NH—C(=O)—NHCH$_3$ | —CH$_2$CH(OH)CH$_3$ |

-continued

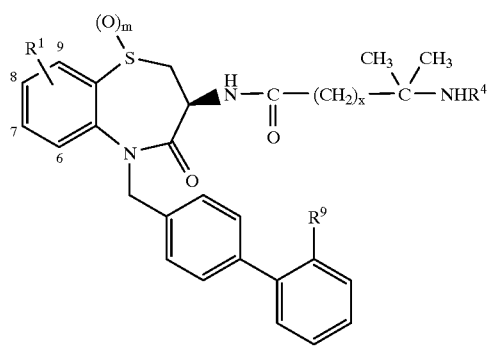

| R¹ | X | m | R⁹ | R⁴ |
|---|---|---|---|---|
| 8-OCH₃ | 1 | 0 | —NH—C(=O)—NHCH₃ | —CH₂CH(OH)CH₃ |
| 8-SCH₃ | 1 | 0 | —NH—C(=O)—NHCH₃ | —CH₂CH(OH)CH₃ |
| 9-F | 1 | 0 | —NH—C(=O)—NHCH₃ | —CH₂CH(OH)CH₃ |
| 8-F | 1 | 0 | —NH—C(=O)—NHCH₃ | —CH₂C(CH₃)₂OH |
| 8-F | 1 | 0 | —NH—C(=O)—NHCH₃ | —CH₂CH(OH)—CH(OH)—CH₃ |
| H | 1 | 0 | —NH—C(=O)—NHCH₂CH₂OH | H |
| H | 1 | 0 | —NH—C(=O)—NHCH₂CH₂OH | —CH₂CH(OH)CH₃ |
| H | 1 | 1 | —NH—C(=O)—NHCH₂CH₂OH | —CH₂CH(OH)CH₃ |
| H | 1 | 0 | —NH—C(=O)—NHCH₂CH₂OH | —CH₂CH(OH)CH₂OH |
| H | 1 | 0 | —NH—C(=O)—NHCH₂CH₂OH | —CH₂CH₂CH(OH)—CH₃ |
| H | 0 | 0 | —NH—C(=O)—NHCH₂CH₂OH | —CH₂CH₂CH(OH)—CH₃ |
| H | 1 | 0 | —NH—C(=O)—NHCH₂CH₂OH | —CH₂CH(OH)—CH(OH)—CH₃ |
| 8-F | 1 | 0 | —NH—C(=O)—NHCH₂CH₂OH | —CH₂CH(OH)CH₃ |

-continued

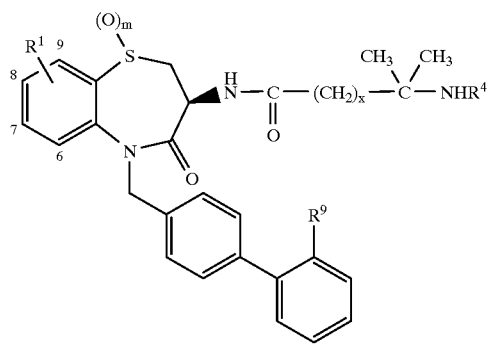

| R¹ | X | m | R⁹ | R⁴ |
|---|---|---|---|---|
| 8-CF₃ | 1 | 0 | —NH—C(=O)—NHCH₂CH₂OH | —CH₂CH(OH)CH₃ |
| 8-OCH₃ | 1 | 0 | —NH—C(=O)—NHCH₂CH₂OH | —CH₂CH(OH)CH₃ |
| 8-F | 1 | 0 | —NH—C(=O)—NHCH₂CH₂OH | —CH₂CH(OH)CH₃ |

EXAMPLE 65

Utilizing the procedures described in Examples 1 to 60 and general methods of organic synthesis described in the chemical literature and familiar to one skilled in the art, the following compounds of Formula I can be prepared from the appropriately substituted starting materials and reagents.

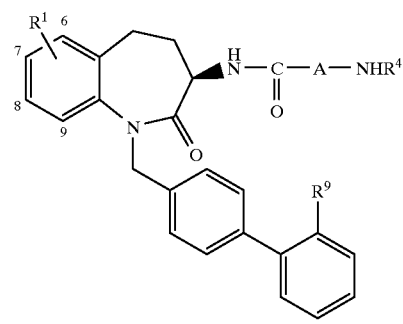

| R₁ | R⁹ | A | R⁴ |
|---|---|---|---|
| H | —CH₂NH—C(=O)—NH₂ | —CH₂—C(CH₃)₂— | —CH₂—CH(OH)—CH(OH)—CH₂OH |
| H | —CH₂NH—C(=O)—NH₂ | —CH₂—C(CH₃)₂— | —CH₂CH₂OH |
| H | —CH₂NH—C(=O)—NH₂ | —CH₂—C(CH₃)₂— | —CH₂C(CH₃)₂(OH) |

-continued

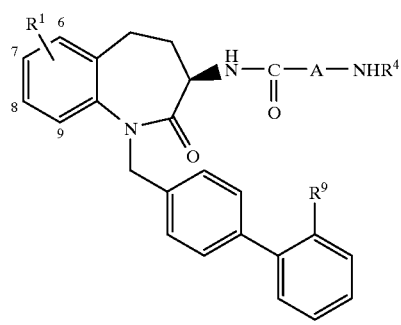

| R¹ | R⁹ | A | R⁴ |
|---|---|---|---|
| H | —CH₂NH—C(=O)—NH₂ | —CH₂—C(CH₃)(CH₃)— | —CH₂CH₂CH(OH)CH₃ |
| H | —CH₂NH—C(=O)—NH₂ | —CH₂—C(CH₃)(CH₃)— | —CH₂—C₆H₅ |
| H | —CH₂NH—C(=O)—NH₂ | —CH₂—C(CH₃)(CH₃)— | —CH₂CH₂CH₃ |
| H | —CH₂NH—C(=O)—NH₂ | —CH₂—C(CH₃)(CH₃)— | —CH₃ |
| H | —CH₂NH—C(=O)—NHCH₃ | —C(H)(CH₃)— | H |
| H | —CH₂NH—C(=O)—NHCH₃ | —C(CH₃)(H)— | H |
| H | —CH₂NH—C(=O)—NHCH₃ | —C(H)(CH₂OH)— | H |
| H | —CH₂NH—C(=O)—NHCH₃ | —C(HOCH₂)(H)— | H |
| H | —CH₂NH—C(=O)—NHCH₃ | —C(CH₃)(CH₂OH)— | H |
| H | —CH₂NH—C(=O)—NHCH₃ | —CH₂—C(CH₃)(CH₂OH)— | H |
| H | —CH₂NH—C(=O)—NHCH₃ | —CH₂—C(HOCH₂)(CH₃)— | H |
| H | —CH₂NH—C(=O)—NHCH₂CH₃ | —C(H)(CH₃)— | —CH₂—CH(OH)—CH₃ |
| H | —CH₂NH—C(=O)—NHCH₂CH₃ | —C(CH₃)(H)— | —CH₂—CH(OH)—CH₃ |

-continued

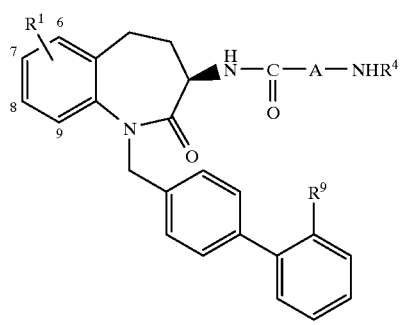

| R¹ | R⁹ | A | R⁴ |
|---|---|---|---|
| H | —CH₂NH—C(=O)—NHCH₂CH₃ | —C(H)(CH₂OH)— | —CH₂—CH(OH)—CH₃ |
| H | —CH₂NH—C(=O)—NHCH₂CH₃ | —C(HOCH₂)(H)— | —CH₂—CH(OH)—CH₃ |
| H | —CH₂NH—C(=O)—NHCH₂CH₃ | —C(CH₃)(CH₂OH)— | —CH₂—CH(OH)—CH₃ |
| H | —CH₂NH—C(=O)—NHCH₂CH₃ | —CH₂—C(CH₃)(CH₂OH)— | —CH₂—CH(OH)—CH₃ |
| H | —CH₂NH—C(=O)—NHCH₂CH₃ | —CH₂—C(HOCH₂)(CH₃)— | —CH₂—CH(OH)—CH₃ |
| H | —CH₂NH—C(=O)—NHCH₂Ph | —C(H)(CH₃)— | —CH₂—CH(OH)—CH₂OH |
| H | —CH₂NH—C(=O)—NHCH₂Ph | —C(CH₃)(H)— | —CH₂—CH(OH)—CH₂OH |
| H | —CH₂NH—C(=O)—NHCH₂Ph | —C(H)(CH₂OH)— | —CH₂—CH(OH)—CH₂OH |
| H | —CH₂NH—C(=O)—NHCH₂Ph | —C(HOCH₂)(H)— | —CH₂—CH(OH)—CH₂OH |
| H | —CH₂NH—C(=O)—NHCH₂Ph | —C(CH₃)(CH₂OH)— | —CH₂—CH(OH)—CH₂OH |
| H | —CH₂NH—C(=O)—NHCH₂Ph | —CH₂—C(CH₃)(CH₂OH)— | —CH₂—CH(OH)—CH₂OH |
| H | —CH₂NH—C(=O)—NHCH₂Ph | —CH₂—C(HOCH₂)(CH₃)— | —CH₂—CH(OH)—CH₂OH |
| 6-F | —CH₂NH—C(=O)—NH₂ | —CH₂—C(CH₃)(CH₃)— | H |

-continued

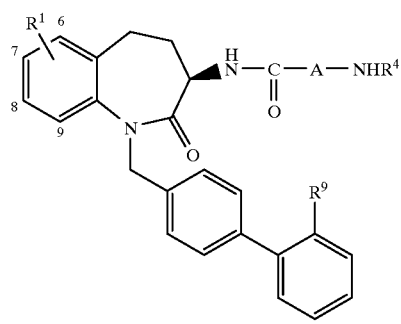

| R¹ | R⁹ | A | R⁴ |
|---|---|---|---|
| 6-OCH₃ | —CH₂NH—C(=O)—NH₂ | —CH₂—C(CH₃)₂— | H |
| 7-Br | —CH₂NH—C(=O)—NH₂ | —CH₂—C(CH₃)₂— | H |
| 7-Cl | —CH₂NH—C(=O)—NH₂ | —CH₂—C(CH₃)₂— | H |
| 7-CH₃ | —CH₂NH—C(=O)—NH₂ | —CH₂—C(CH₃)₂— | H |
| 8-Cl | —CH₂NH—C(=O)—NH₂ | —CH₂—C(CH₃)₂— | H |
| 8-I | —CH₂NH—C(=O)—NH₂ | —CH₂—C(CH₃)₂— | H |
| H | —CH₂NH—C(=O)—N(CH₃)₂ | —CH₂—C(CH₃)₂— | H |
| H | —CH₂NH—C(=O)—NHCH(CH₃)₂ | —CH₂—C(CH₃)₂— | H |
| H | —CH₂N(CH₃)—C(=O)—NHCH₃ | —CH₂—C(CH₃)₂— | H |
| H | —CH₂NH—C(=O)—NHCH₂Ph | —CH₂—C(CH₃)₂— | H |
| H | —CH₂NH—C(=O)—N(pyrrolidinyl) | —CH₂—C(CH₃)₂— | H |
| H | —CH₂NH—C(=O)—N(morpholinyl) | —CH₂—C(CH₃)₂— | H |

-continued

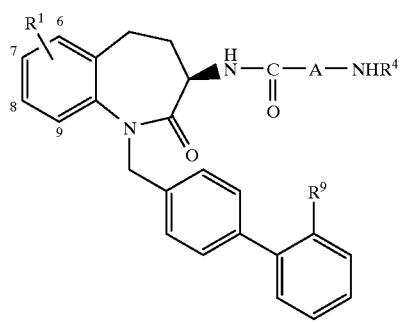

| R¹ | R⁹ | A | R⁴ |
|---|---|---|---|
| H | —CH₂NH—C(=O)—N(piperazine)NH | —CH₂—C(CH₃)(CH₃)— | H |

EXAMPLE 66

Utilizing the procedures described in Examples 1 to 60 and general methods of organic synthesis described in the chemical literature and familiar to one skilled in the art, the following compounds of Formula I can be prepared from the appropriately substituted starting materials and reagents.

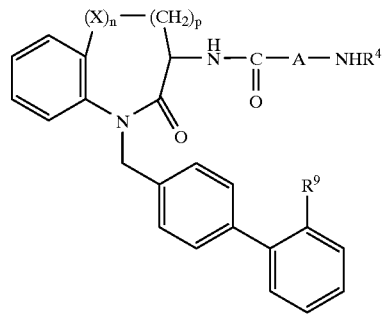

| X | n | p | R⁹ | A | R⁴ |
|---|---|---|---|---|---|
| — | 0 | 3 | —CH₂NH—C(=O)—NHCH₃ | —C(CH₃)(CH₃)— | H |
| — | 0 | 3 | —CH₂NH—C(=O)—NHCH₃ | —CH₂—C(CH₃)(CH₃)— | —CH₂CH(OH)CH₃ |
| — | 0 | 3 | —CH₂NH—C(=O)—NHCH₃ | —CH₂—C(CH₃)(CH₃)— | —CH₂CH(OH)CH₂OH |
| — | 0 | 1 | —CH₂NH—C(=O)—NHCH₃ | —C(CH₃)(CH₃)— | H |
| — | 0 | 1 | —CH₂NH—C(=O)—NHCH₃ | —CH₂—C(CH₃)(CH₃)— | —CH₂CH(OH)CH₃ |

-continued

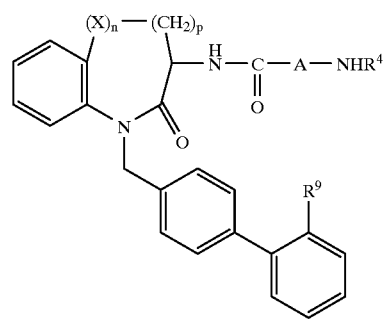

| X | n | p | R⁹ | A | R⁴ |
|---|---|---|----|---|----|
| — | 0 | 1 | —CH₂NH—C(=O)—NHCH₃ | —CH₂—C(CH₃)(CH₃)— | —CH₂CH(OH)CH₂OH |
| — | 0 | 0 | —CH₂NH—C(=O)—NHCH₃ | —C(CH₃)(CH₃)— | H |
| — | 0 | 0 | —CH₂NH—C(=O)—NHCH₃ | —CH₂—C(CH₃)(CH₃)— | —CH₂CH(OH)CH₃ |
| — | 0 | 0 | —CH₂NH—C(=O)—NHCH₃ | —CH₂—C(CH₃)(CH₃)— | —CH₂CH(OH)CH₂OH |
| C=O | 1 | 1 | —CH₂NH—C(=O)—NHCH₃ | —CH₂—C(CH₃)(CH₃)— | —CH₂CH(OH)CH₃ |
| CHOH | 1 | 1 | —CH₂NH—C(=O)—NHCH₃ | —CH₂—C(CH₃)(CH₃)— | —CH₂CH(OH)CH₃ |
| S | 1 | 0 | —CH₂NH—C(=O)—NHC₂H₅ | —CH₂—C(CH₃)(CH₃)— | H |
| S | 1 | 0 | —CH₂NH—C(=O)—NHCH₂CH₂OH | —C(CH₃)(CH₃)— | H |
| S | 1 | 0 | —CH₂NH—C(=O)—NHCH₃ | —CH₂—C(CH₃)(CH₃)— | —CH₂CH(OH)CH₃ |
| SO | 1 | 0 | —CH₂NH—C(=O)—NHCH₃ | —CH₂—C(CH₃)(CH₃)— | H |
| SO | 1 | 0 | —CH₂NH—C(=O)—NH₂ | —C(CH₃)(CH₃)— | H |
| SO | 1 | 0 | —CH₂NH—C(=O)—NH₂ | —CH₂—C(CH₃)(CH₃)— | —CH₂CH(OH)CH₃ |

-continued

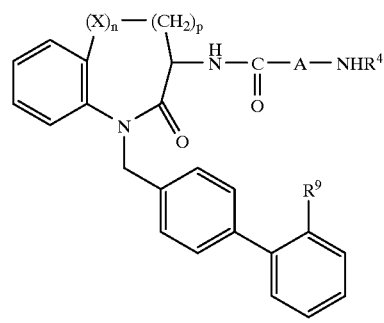

| X | n | p | R⁹ | A | R⁴ |
|---|---|---|---|---|---|
| SO | 1 | 0 | —CH₂NH—C(=O)—NH₂ | —CH₂—C(CH₃)(CH₃)— | —CH₂CH(OH)CH₂OH |
| S | 1 | 2 | —CH₂NH—C(=O)—NH₂ | —CH₂—C(CH₃)(CH₃)— | H |
| S | 1 | 2 | —CH₂NH—C(=O)—NH₂ | —C(CH₃)(CH₃)— | H |
| S | 1 | 2 | —CH₂NH—C(=O)—NH₂ | —CH₂—C(CH₃)(CH₃)— | —CH₂CH(OH)CH₃ |
| S | 1 | 2 | —CH₂NH—C(=O)—NH₂ | —CH₂—C(CH₃)(CH₃)— | —CH₂CH(OH)CH₂OH |
| S | 1 | 2 | —CH₂NH—C(=O)—NH₂ | —CH₂—C(CH₃)(CH₃)— | H |
| S | 1 | 2 | —CH₂NH—C(=O)—NHCH₂Ph | —C(CH₃)(CH₃)— | H |
| S | 1 | 2 | —CH₂NH—C(=O)—NHC₂H₅ | —CH₂—C(CH₃)(CH₃)— | —CH₂CH(OH)CH₃ |
| S | 1 | 2 | —CH₂NH—C(=O)—NHPh | —CH₂—C(CH₃)(CH₃)— | —CH₂CH(OH)CH₂OH |
| O | 1 | 1 | —CH₂NH—C(=O)—NHCH₃ | —CH₂—C(CH₃)(CH₃)— | H |
| O | 1 | 1 | —CH₂NH—C(=O)—NHCH₃ | —C(CH₃)(CH₃)— | H |
| O | 1 | 1 | —CH₂NH—C(=O)—NH₂ | —CH₂—C(CH₃)(CH₃)— | —CH₂CH(OH)CH₃ |
| O | 1 | 1 | —CH₂NH—C(=O)—NHCH₃ | —CH₂—C(CH₃)(CH₃)— | —CH₂CH(OH)CH₂OH |

What is claimed is:
1. A compound having the formula:

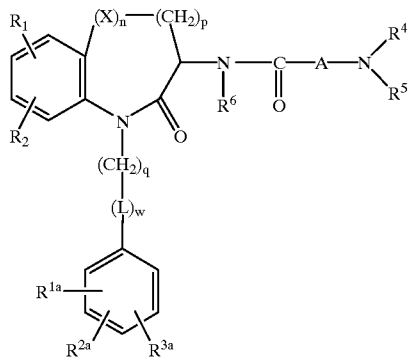

where L is

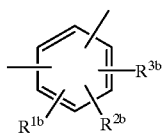

n is 1;
p is 1;
q is 0 to 4;
w is 0 or 1;
X is O, $S(O)_m$,
m is 0 to 2;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, $—S(O)_m R^{7a}$, cyano, nitro, $R^{7b}O(CH_2)_v—$, $R^{7b}COO(CH_2)_v—$, $R^{7b}OCO(CH_2)_v$-, $R^4R^5N(CH_2)_v—$, $R^{7b}CON(R^4)(CH_2)_v—$, $R^4R^5NCO(CH_2)_v—$, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl or substituted phenyl; phenyl or substituted phenyl where the phenyl substituents are from 1 to 3 of halogen, $C_1$–$C_6$ alkyl, $C_1$–$C_6$ alkoxy, or hydroxy and v is 0 to 3;

$R^{3a}$ and $R^{3b}$ are independently hydrogen, $R^9$, $C_1$–$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is $R^{4b}R^{12b}NCON(R^{12a})(CH_2)_v—$,
$R^{4b}R^{12b}NCSN(R^{12a})(CH_2)_v—$,
$R^{4b}R^{12c}NN(R^{12b})CSN(R^{12a})(CH_2)_v—$,
$R^{4b}R^{12c}NN(R^{12b})CON(R^{12a})(CH_2)_v—$,
$R^{4b}R^{12c}NN(R^{12b})COO(CH_2)_v—$, $R^{4b}R^{12b}NCOO(CH_2)_v—$
or $R^{13}OCON(R^{12a})(CH_2)_v—$, where v is 0 to 3;

$R^{12a}$, $R^{12b}$ and $R^{12c}$ are independently $R^{5a}$, $OR^{5a}$, or $COR^{5a}$, $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form $—(CH_2)_r—B—(CH_2)_s—$ where B is $CHR^1$, O, $S(O)_m$ or $NR^{10}$, m is 0, 1 or 2, r and s are independently 0 to 3 and $R^1$ and $R^{10}$ are as defined;

$R^{13}$ is: $C_1$–$C_3$ perfluoroalkyl, $C_1$–$C_6$ alkyl, substituted $C_1$–$C_6$ alkyl, where the substitutents are hydroxy, $NR^{10}R^{11}$, carboxy, phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy;

and v is as defined above;

$R^4$, $R^{4b}$, $R^5$ and $R^{5a}$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl, or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, fluoro, $R^1$, $R^2$ independently disubstituted phenyl $C_1$–$C_3$ alkoxy, $R^1$, $R^2$ independently disubstituted phenyl, $C_1$–$C_{20}$-alkanoyloxy, $C_1$–$C_5$ alkoxycarbonyl, carboxy, formyl or $—NR^{10}R^{11}$ where $R^{10}$ and $R^{11}$ are independently hydrogen, $C_1$–$C_6$ alkyl, phenyl, phenyl $C_1$–$C_6$ alkyl, $C_1$–$C_5$-alkoxycarbonyl or $C_1$–$C_5$-alkanoyl-$C_1$–$C_6$ alkyl; or $R^4$ and $R^5$ can be taken together to form $—(CH_2)_r—B—(CH_2)_s—$ where B is $CHR^1$, O, $S(O)_m$ or $N—R^{10}$, r and s are independently 1 to 3 and $R^1$ and $R^{10}$ are as defined above;

$R^6$ is hydrogen, $C_1$–$C_{10}$ alkyl, phenyl or phenyl $C_1$–$C_{10}$ alkyl;

A is

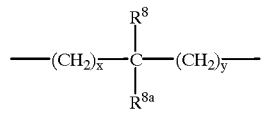

where x and y are independently 0–3;

$R^8$ and $R^{8a}$ are independently hydrogen, $C_1$–$C_{10}$ alkyl, trifluoromethyl, phenyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $C_3$–$C_7$ cycloalkyl, $R^1$, $R^2$ independently disubstituted phenyl $C_1$–$C_3$ alkoxy, $R^1$, $R^2$ independently disubstituted phenyl, $C_1$–$C_5$-alkanoyloxy, $C_1$–$C_5$ alkoxycarbonyl, carboxy, formyl, or $—NR^{10}R^{11}$ where $R^{10}$ and $R^{11}$ are as defined above; or $R^8$ and $R^{8a}$ can be taken together to form $—(CH_2)_t—$ where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

2. A compound of claim 1 wherein:
n is 1;
p is 1;
q is 0 to 2;
w is 0 or 1;
X is O, $S(O)_m$,
m is 0 to 2;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $—S(O)_m R^{7a}$, $R^{7b}O(CH_2)_v—$, $R^{7b}COO(CH_2)_v—$, $R^{7b}OCO(CH_2)_v—$, phenyl or substituted phenyl where the substituents are from 1 to 3 of halogen, $C_1$–$C_6$ alkyl, $C_1$–$C_6$ alkoxy or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl; phenyl and v is 0 to 2;

$R^{3a}$ and $R^{3b}$ are independently hydrogen, $R^9$, $C_1$–$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is $R^{4b}R^{12b}NCON(R^{12a})(CH_2)_v$—,
$R^{4b}R^{12b}NCSN(R^{12a})(CH_2)_v$—,
$R^{4b}R^{12c}NN(R^{12b})CON(R^{12a})(CH_2)_v$—,
$R^{4b}R^{12c}NN(R^{12b})COO(CH_2)_v$—,
$R^{4b}R^{12b}NCOO(CH_2)_v$— or $R^{13}OCON(R^{12a})(CH_2)_v$—, where v is 0 to 3;

$R^{12a}$, $R^{12b}$ and $R^{12c}$ are independently $R^{5a}$, $OR^{5a}$, or $COR^{5a}$, $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, $R^1$ is as defined above and $R^{10}$ is hydrogen, $C_1$–$C_6$ alkyl, phenyl $C_1$–$C_6$ alkyl or $C_1$–$C_5$ alkanoyl-$C_1$–$C_6$ alkyl;

$R^{13}$ is $C_1$–$C_3$ perfluoroalkyl, $C_1$–$C_6$ alkyl, substituted $C_1$–$C_6$ alkyl, where the substituents are hydroxy, $NR^{10}R^{11}$, carboxy, phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy;

where v is as defined above;

$R^4$, $R^{4b}$, $R^5$ and $R^{5a}$ are independently hydrogen, phenyl, substituted phenyl, $C_1$–$C_{10}$ alkyl, substituted $C_1$–$C_{10}$ alkyl, where the substituents on the alkyl or phenyl are from 1 to 5 of hydroxy, $C_1$–$C_6$ alkoxy, $C_3$–$C_7$ cycloalkyl, fluoro, $R^1$, $R^2$ independently disubstituted phenyl $C_1$–$C_3$ alkoxy, $R^1$, $R^2$ independently disubstituted phenyl, $C_1$–$C_{20}$-alkanoyloxy, $C_1$–$C_5$ alkoxycarbonyl, carboxy or formyl;

$R^4$ and $R^5$ can be taken together to form —$(CH_2)_r$—B—$(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$–$C_{10}$ alkyl or phenyl $C_1$–$C_{10}$ alkyl;

A is

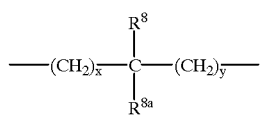

where x and y are independently 0–2;

$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, $S(O)_mR^{7a}$, $C_1$–$C_6$ alkoxy, $R^1$, $R^2$ independently disubstituted phenyl, $C_1$–$C_5$-alkanoyloxy, $C_1$–$C_5$ alkoxycarbonyl, carboxy, formyl, —$NR^{10}R^{11}$ where $R^{10}$ and $R^{11}$ are independently hydrogen, $C_1$–$C_6$ alkyl or $C_1$–$C_5$ alkanoyl-$C_1$–$C_6$ alkyl;

or $R^8$ and $R^{8a}$ can be taken together to formn —$(CH_2)_t$— where t is 2 to 4;

and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

3. A compound of claim 2 wherein:
n is 1;
p is 1;
q is 0 to 2;
w is 0 or 1;
X is $S(O)_m$ or;
m is 0 or 1;

$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, —$S(O)_mR^{7a}$, $R^{7b}O(CH_2)_v$—, $_R{}^{7b}COO(CH_2)_v$—, $R^{7b}OCO(CH_2)_v$—, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_6$ alkyl or substituted $C_1$–$C_6$ alkyl where the substituents are phenyl and v is 0 to 2;

$R^{3a}$ and $R^{3b}$ are independently hydrogen, $R^9$, $C_1$–$C_6$ alkyl substituted with $R^9$, phenyl substituted with $R^9$ or phenoxy substituted with $R^9$ with the proviso that either $R^{3a}$ or $R^{3b}$ must be a substituent other than hydrogen;

$R^9$ is $R^{4b}R^{12b}NCON(R^{12a})(CH_2)_v$—,
$R^{4b}R^{12b}NCSN(R^{12a})(CH_2)_v$—,
$R^{4b}R^{12c}NN(R^{12b})CON(R^{12a})(CH_2)_v$—,
$R^{4b}R^{12c}NN(R^{12b})COO(CH_2)_v$—,
$R^{4b}R^{12b}NCOO(CH_2)_v$— or $R^{13}OCON(R^{12a})(CH_2)_v$—, where v is 0 to 2;

$R^{12a}$, $R^{12b}$ and $R^{12c}$ are independently $R^{5a}$, $OR^{5a}$, or $COR^{5a}$, $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$–$C_6$ alkyl or $C_1$–$C_5$ alkanoyl-$C_1$–$C_6$ alkyl;

$R^{13}$ is $C_1$–$C_6$ alkyl, substituted $C_1$–$C_6$ alkyl, where the substituents are phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy;

$R^4$, $R^{4b}$, $R^5$ and $R^{5a}$ are independently hydrogen, $C_1$–$C_{10}$ alkyl, substituted $C_1$–$C_{10}$ alkyl, where the substituents on the alkyl are from 1 to 5 of hydroxy, $C_1$–$C_6$ alkoxy, fluoro, $R^1$, $R^2$ independently disubstituted phenyl, $C_1$–$C_{20}$-alkanoyloxy, $C_1$–$C_5$ alkoxycarbonyl or carboxy;

$R^6$ is hydrogen or $C_1$–$C_{10}$ alkyl;

A is

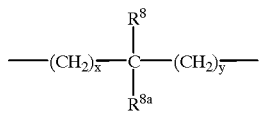

where x and y are independently 0–2;

$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, $S(O)_mR^{7a}$, $C_1$–$C_6$ alkoxy, $R^1$, $R^2$ independently disubstituted phenyl, $C_1$–$C_5$-alkanoyloxy, $C_1$–$C_5$ alkoxycarbonyl, carboxy; or $R^8$ and $R^{8a}$ can be taken together to form —$(CH_2)_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

4. A compound of claim 3 wherein:

n is 1;

p is 1;

q is 1;

w is 1;

X is $S(O)_m$;

m is 0 or 1;

$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, $-S(O)_m R^{7a}$, $R^{7b}O(CH_2)_v-$, $R^{7b}COO(CH_2)_v-$, phenyl or substituted phenyl where the substituents are from 1 to 3 of halogen, $C_1-C_6$ alkyl, $C_1-C_6$ alkoxy or hydroxy;

$R^{7a}$ and $R^{7b}$ are independently hydrogen, $C_1-C_6$ alkyl, substituted $C_1-C_6$ alkyl, where the substituents are phenyl and v is 0 or 1;

$R^{3a}$ and $R^{3b}$ are independently hydrogen, $R^9$, or $C_1-C_6$ alkyl substituted with $R^9$ with the proviso that either $R^{3a}$ or $R^{3b}$ must be a substituent other than hydrogen;

$R^9$ is $R^{4b}R^{12b}NCON(R^{12a})(CH_2)_v-$,
$R^{4b}R^{12c}NN(R^{12b})CON(R^{12a})(CH_2)_v-$,
$R^{4b}R^{12c}NN(R^{12b})COO(CH_2)_v-$,
$R^{4b}R^{12b}NCOO(CH_2)_v-$ or $R^{13}OCON(R^{12a})(CH_2)_v-$, where v is 0 or 1;

$R^{12a}$, $R^{12b}$ and $R^{12c}$ are independently $R^{5a}$, $OR^{5a}$, or $COR^{5a}$, $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form $-(CH_2)_r-B-(CH_2)_s-$ where B is $CHR^1$, O, $S(O)_m$ or $NR^{10}$, m is 0, 1 or 2, r and s are independently 0 to 2, $R^1$ is as defined above and $R^{10}$ is hydrogen, $C_1-C_6$ alkyl or $C_1-C_5$ alkanoyl-$C_1-C_6$ alkyl;

$R^{13}$ is $C_1-C_6$ alkyl, substituted $C_1-C_6$ alkyl, where the substituents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^4$, $R^{4b}$, $R^5$ and $R^{5a}$ are independently hydrogen, $C_1-C_{10}$ alkyl, substituted $C_1-C_{10}$ alkyl, where the substituents on the alkyl are from 1 to 3 of hydroxy, $C_1-C_3$ alkoxy, fluoro, $R^1$, $R^2$ independently disubstituted phenyl, $C_1-C_{20}$ alkanoyloxy, $C_1-C_5$ alkoxycarbonyl or carboxy;

$R^6$ is hydrogen;

A is

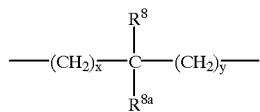

where x and y are independently 0–1;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_m R^{7a}$, $C_1-C_6$ alkoxy, $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $-(CH_2)_t-$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

5. A stereospecific compound of claim 1 having the following structural formula:

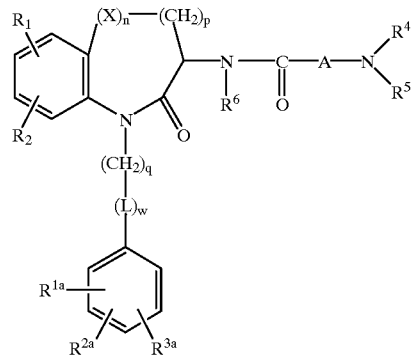

where $R^1$, $R^2$, X, n, p, q, L, w, $R^{1a}$, $R^{2a}$, $R^{3a}$, $R^4$, $R^5$, $R^6$ and A are as defined in claim 1.

6. A compound of claim 1 which is:

N-[5-[[2'-[(Methoxycarbonyl)amino][1,1'-biphenyl]-4-yl]methyl]-2,3,4,5-tetrahydro-4-oxo-1,5-benzothiazepin-3(S)-yl]-3-amino-3-methylbutanamide;

N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-amino-3-methylbutanamide;

N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-amino-3-methylbutanamide;

N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-amino-3-methylbutanamide;

N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[2(R)-hydroxypropyl]amino-3-methylbutanamide;

N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-[2(R)-hydroxypropyl]amino-3-methylbutanamide;

N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-[2(R)-hydroxypropyl]amino-3-methylbutanamide;

N-[-5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[2(S),3-dihydroxypropyl]amino-3-methylbutanamide;

2Amino-2-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]propanamide;

2-Amino-2-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]propanamide;

2-Amino-2-methyl-N-[2,3,4,5-tetrahydro-5-[[2'-[[[(methylamino)carbonyl]amino]methyl][1,1'- biphenyl]-4-yl]methyl]-8-methoxy-4-oxo-1,5-benzothiazepin-3(S)-yl]propanamide;

2-Amino-2-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]propanamide;

2-Amino-2-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]propanamide;

3-Amino-3-methyl-N-[2,3,4,5-tetrahydro-5-[[2'-[[[(methylamino)carbonyl]amino]methyl][1,1'-biphenyl]-4-yl]methyl]-4-oxo-1,5-benzothiazepin-3(S)-yl]butanamide;

3-Amino-3-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]butanamide;

3-Amino-3-methyl-N-[2,3,4,5-tetrahydro-5-[[2'-[[[(methylamino)carbonyl]amino]methyl][1,1'-biphenyl]-4-yl]methyl]-8-methoxy-4-oxo-1,5-benzothiazepin-3(S)-yl]butanamide;

3-Amino-3-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]butanamide;

3-Amino-3-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]butanamide;

3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]4-oxo-1,5-benzothiazepin-3(S)-yl]butanamide;

3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-fluoro-4-oxo-1,5-benzothiazepin-3(S)-yl]butanamide;

3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-methoxy-4-oxo-1,5-benzothiazepin-3(S)-yl]butanamide;

3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-methylthio-4-oxo-1,5-benzothiazepin-3(S)-yl]butanamide;

3-[2(R)-Hydroxypropyl]amino-3-methyl-N-[2,3,4,5-tetrahydro-5-[[2'-[[[(methylamino)carbonyl]amino]methyl][1,1'-biphenyl]-4-yl]methyl]-8-trifluoromethyl-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]-methyl]-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]-methyl]-8-fluoro-4-oxo-1,5-benzothiazepin-3(S)-yl]-butanamide;

3-[2(S),3-Dihydroxypropyl]amino-3-methyl-N-[2,3,4,5-tetrahydro-5-[[2'-[[[(methylamino)carbonyl]amino]methyl][1,1'-biphenyl)-4-yl]-methyl]-8-methoxy-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]-methyl]-8-methylthio-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(methylamino)carbonyl]amino]methyl][1,1'-biphenyl]-4-yl]-methyl]-8-trifluoromethyl-4-oxo-1,5-benzothiazepin-3(S)-yl]-butanamide;

2-Amino-2-methyl-N-[2,3,4,5-tetrahydro-1-[[2'-[[(aminocarbonyl)amino]methyl][1,1'-biphenyl]-4-yl]methyl]-4-oxo-1,5-benzothiazepin-3(S)-yl]propanamide;

2-Amino-2-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]propanamide;

2-Amino-2-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]propanamide;

2-Amino-2-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]propanamide;

2-Amino-2-methyl-N-[2,3,4,5-tetrahydro-1-[[2'-[[(aminocarbonyl)amino]methyl][1,1'-biphenyl]-4-yl]methyl]-8-trifluoromethyl-4-oxo-1,5-benzothiazepin-3(S)-yl]propanamide;

3-Amino-3-methyl-N-[2,3,4,5-tetrahydro-5-[[2'-[[(aminocarbonyl)amino]methyl][1,1'-biphenyl]-4-yl]methyl]-4-oxo-1,5-benzothiazepin-3(S)-yl]butanamide;

3-Amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;

3-Amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]butanamide;

3-Amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;

3-Amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]butanamide;

3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-4-oxo-1,5-benzothiazepin-3(S)-yl]butanamide;

3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]butanamide;

3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]butanamide;

3-[2(R)-Hydroxypropyl]amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]butanamide;

3-[2(R)-Hydroxypropyl]amino-3-methyl-N-[2,3,4,5-tetrahydro-5-[[2'-[[(aminocarbonyl)amino]methyl][1, 1'-biphenyl]-4-yl]methyl]-8-trifluoromethyl-4-oxo-1, 5-benzothiazepin-3(S)-yl]butanamide;

3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-4-oxo-1,5-benzothiazepin-3(S)-yl]butanamide;

3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-fluoro-4-oxo-1,5-benzothiazepin-3(S)-yl]-butanamide;

3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-methoxy-4-oxo-1,5-benzothiazepin-3(S)-yl]-butanamide;

3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-methylthio-4-oxo-1,5-benzothiazepin-3(S)-yl]-butanamide;

3-[2(S),3-Dihydroxypropyl]amino-3-methyl-N-[2,3,4,5-tetrahydro-5-[[2'-[[(aminocarbonyl)amino]methyl][1,1'-biphenyl]-4-yl]methyl]-8-trifluoromethyl-4-oxo-1,5-benzothiazepin-3(S)-yl]-butanamide;

2-Amino-2-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]propanamide;

2-Amino-2-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]propanamide;

2-Amino-2-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]propanamide;

2-Amino-2-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]propanamide;

2-Amino-2-methyl-N-[2,3,4,5-tetrahydro-5-[[2'-[[[(ethylamino)carbonyl]amino]methyl][1,1'-biphenyl]-4-yl]methyl]-8-trifluoro-methyl-4-oxo-1,5-benzothiazepin-3(S)-yl]propanamide;

3-Amino-3-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]butanamide;

3-Amino-3-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]butanamide;

3-Amino-3-methyl-N-[2,3,4,5-tetrahydro-5-[[2'-[[[(ethylamino)carbonyl]amino]methyl][1,1'-biphenyl]-4-yl]methyl]-8-methoxy-4-oxo-1,5-benzothiazepin-3(S)-yl]butanamide;

3-Amino-3-methyl-N-[2,3,4,5-tetrahydro-5-[[2'-[[[(ethylamino)carbonyl]-amino]methyl][1,1'-biphenyl]-4-yl]methyl]-8-methylthio-4-oxo-1,5-benzothiazepin-3(S)-yl]butanamide;

3-Amino-3-methyl-N-[2,3,4,5-tetrahydro-5-[[2'-[[[(ethylamino)carbonyl]amino]methyl][1,1'-biphenyl)-4-yl]methyl]-8-trifluoromethyl-4-oxo-1,5-benzothiazepin-3(S)-yl]butanamide;

3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]-methyl]-4-oxo-1,5-benzothiazepin-3(S)-yl]butanamide;

3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]-methyl]-8-fluoro-4-oxo-1,5-benzothiazepin-3(S)-yl]butanamide;

3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]-methyl]-8-methoxy-4-oxo-1,5-benzothiazepin-3(S)-yl]-butanamide;

3-[2(R)-Hydroxypropyl]amino-3-methyl-N-[2,3,4,5-tetrahydro-5-[[2'-[[[(ethylamino)carbonyl]amino]methyl][1,1'-biphenyl]-4'-yl]methyl]-8-methylthio-4-oxo-1,5-benzothiazepin-3(S)-yl]-butanamide;

3-[2(R)-Hydroxypropyl]amino-3-methyl-N-[2,3,4,5-tetrahydro-5-[[2'-[[[(ethylamino)carbonyl]amino]methyl][1,1'-biphenyl]-4-yl]-methyl]-8-trifluoromethyl-4-oxo-1,5-benzothiazepin-3(S)-yl]-butanamide;

3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-4-oxo-1,5-benzothiazepin-3(S)-yl]-butanamide;

3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-fluoro-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(ethylamino)carbonyl]amino]methyl [1,1'-biphenyl]-4-yl]methyl]-8-methoxy-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-methylthio-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[(ethylamino)carbonyl]amino]methyl][1,1'-biphenyl]-4-yl]methyl]-8-trifluoromethyl-4-oxo-1,5-benzo-thiazepin-3(S)-yl]butanamide;

2-Amino-2-methyl-N-[2,3,4,5-tetrahydro-5-[[2'-[[[[(hydroxyethyl)amino]carbonyl]amino]methyl][1,1'-biphenyl]-4-yl]methyl]-4-oxo-1,5-benzothiazepin-3(S)-yl]propanamide;

2-Amino-2-methyl-N-[2,3,4,5-tetrahydro-5-[[2'-[[[[(hydroxyethyl)amino]carbonyl]amino]methyl][1,1'-biphenyl]4-yl]methyl]-8-fluoro-4-oxo-1,5-benzothiazepin-3(S)-yl]propanamide;

2-Amino-2-methyl-N-[2,3,4,5-tetrahydro-5-[[2'-[[[[(hydroxyethyl)amino]carbonyl]amino]methyl][1,1'-biphenyl)-4-yl]methyl]-8-methoxy-4-oxo-1,5-benzothiazepin-3(S)-yl]propanamide;

2-Amino-2-methyl-N-[2,3,4,5-tetrahydro-5-[[2'-[[[[(hydroxyetbyl)amino]carbonyl]amino]methyl][1,1'-biphenyl]-4-yl]methyl]-8-methylthio-4-oxo-1,5-benzothiazepin-3(S)-yl]propanamide;

2-Amino-2-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]propanamide;

3-Amino-3-methyl-N-[2,3,4,5-tetrahydro-5-[[2'-[[[[(hydroxyethyl)amino]carbonyl]amino]methyl][1,1'-biphenyl]4-yl]methyl]-4-oxo-1,5-benzothiazepin-3(S)-yl]butanamide;

3-Amino-3-methyl-N-[2,3,4,5-tetrahydro-5-[[2'-[[[[(hydroxyethyl)amino]carbonyl]amino]methyl][1,1'-biphenyl]-4-yl]methyl]-8-fluoro-4-oxo-1,5-benzothiazepin-3(S)-yl]butanamide;

3-Amino-3-methyl-N-[2,3,4,5-tetrahydro-5-[[2'-[[[[(hydroxyethyl)amino]carbonyl]amino]methyl][1,1'-biphenyl]4-yl]methyl]-8-methoxy-4-oxo-1,5-benzothiazepin-3(S)-yl]butanamide;

3-Amino-3-methyl-N-[2,3,4,5-tetrahydro-5-[[2'-[[[[(hydroxyethyl)amino]carbonyl]amino]methyl][1,1'-biphenyl]-4-yl]methyl]-8-methylthio-4-oxo-1,5-benzothiazepin-3(S)-yl]butanamide;

3-Amino-3-methyl-N-[2,3,4,5-tetrahydro-5-[[2'-[[[[(hydroxyethyl)amino]carbonyl]amino]methyl][1,1'-biphenyl]-4-yl]methyl]-8-trifluoromethyl-4-oxo-1,5-benzothiazepin-3(S)-yl]butanamide;

3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]-methyl]-4-oxo-1,5-benzothiazepin-3(S)-yl]-butanamide;

3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]-methyl]-8-fluoro-4-oxo-1,5-benzothiazepin-3(S)-yl]butanamide;

3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]-methyl]-8-methoxy-4-oxo-1,5-benzothiazepin-3(S)-yl]butanamide;

3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]-methyl]-8-methylthio-4-oxo-1,5-benzothiazepin-3(S)-yl]butanamide;

3-[2(R)-Hydroxypropyl]amino-3-methyl-N-[2,3,4,5-tetrahydro-5-[[2'-[[[[(hydroxyethyl)amino]carbonyl]amino]methyl][1,1'-biphenyl]-4-yl]-methyl]-8-trifluoromethyl-4-oxo-1,5-benzo-thiazine-3(S)-yl]-butanamide;

3-[2(S),3-Dihydroxypropyl]amino-3-methyl-N-[2,3,4,5-tetrahydro-5-[[2'-[[[[(hydroxyethyl)amino]carbonyl]amino]-methyl][1,1'-biphenyl]-4-yl]methyl]-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[[(hydroxyethyl)amino]carbonyl]amino]-methyl][1,1'-biphenyl]-4-yl]methyl]-8-fluoro-4-oxo-1,5-benzo-thiazepin-3(S)-yl]butanamide;

3-[2(S),3-Dihydroxypropyl]amino-3-methyl-N-[2,3,4,5-tetrahydro-5-[[2'-[[[[(hydroxyethyl)amino]carbonyl]amino]-methyl][1,1'-biphenyl]-4-yl]methyl]-8-methoxy-4-oxo-1,5-benzo-thiazepin-3(S)-yl]butanamide;

3-[2(S),3-Dihydroxypropyl]amino-3-methyl-N-[2,3,4,5-tetrahydro-5-[[2'-[[[[(hydroxyethyl)amino]carbonyl]amino]-methyl][1,1'-biphenyl]-4-yl]methyl]-8-methylthio-4-oxo-1,5-benzothiazepin-3(S)-yl]butanamide;

3-[2(S),3-Dihydroxypropyl]amino-3-methyl-N-[2,3,4,5-tetrahydro-5-[[2'-[[[[(hydroxyethyl)amino]carbonyl]amino]-methyl][1,1'-biphenyl]-4-yl]methyl]-8-trifluoromethyl-4-oxo-1,5-benzothiazepin-3(S)-yl]-butanamide;

2-Amino-2-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]propanamide;

3-Amino-3-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]butanamide;

3-[2(R)-Hydroxypropyl]amino-3-methyl-N-[2,3,4,5-tetrahydro-5-[[2'-[[(methoxycarbonyl)amino]methyl][1,1'-biphenyl]-4-yl]-methyl]-4-oxo-1,5-benzothiazepin-3(S)-yl]butanamide;

3-[2(S),3-Dihydroxypropyl]amino-3-methyl-N-[2,3,4,5-tetrahydro-5-[[2'-[[(methoxycarbonyl)amino]methyl][1,1'-biphenyl]-4-yl]methyl]-4-oxo-1,5-benzothiazepin-3(S)-yl]-butanamide;

2-Amino-2-methyl-N-[2,3,4,5-tetrahydro-5-[[2'-[[[(methylamino)carbonyl]oxy]methyl][1,1'-biphenyl]-4-yl]methyl]4-oxo-1,5-benzo-thiazepin-3(S)-yl]propanamide;

3-Amino-3-methyl-N-[2,3,4,5-tetrahydro-5-[[2'-[[[(methylamino)carbonyl]oxy]methyl][1,1'-biphenyl]-4-yl]methyl]-4-oxo-1,5-benzo-thiazepin-3(S)-yl]butanamide;

3-[2(R)-Hydroxypropyl]amino-3-methyl-N-[2,3,4,5-tetrahydro-5-[[2'-[[[(methylamino)carbonyl]oxy]methyl][1,1'-biphenyl]-4-yl]-methyl]-4-oxo-1,5-benzothiazepin-3(S)-yl]butanamide or 3-[2(S),3-Dihydroxypropyl]amino-3-methyl-N-[2,3,4,5-tetra-hydro-5-[[2'-[[[(methylamino)carbonyl]oxy]methyl][1,1'-biphenyl]-4-yl]methyl]-4-oxo-1,5-benzothiazepin-3(S)-yl]butanamide.

7. A process for the preparation of a compound of claim 1 which comprises reacting a compound having a formula:

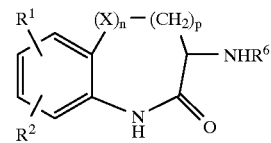

III where $R^1$, $R^2$, $R^6$, X, n and p are as defined in claim 1 with a compound having the formula:

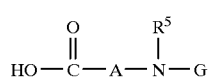

IV where $R^5$ and A are as defined in claim 1 and G is a protecting group; which step is either followed by or preceded by the treatment of the compound with

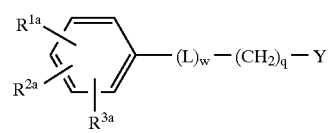

VI where $R^{1a}$, $R^{2a}$, $R^{3a}$, L, w and q are as defined in claim 1 and Y is a leaving group, followed by the replacement of the protecting group G with $R^4$.

8. The process of claim 7 where compound III is first reacted with compound IV followed by reaction with compound VI.

9. A process for the preparation of a compound of claim 1 which comprises reacting a compound having a formula:

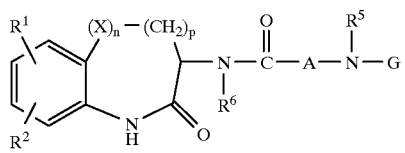

V where $R^1$, $R^2$, $R^5$, $R^6$, X, A, n and p are as defined in claim 1 and G is a protecting group, with a compound having the formula:

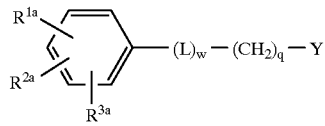

VI where $R^{1a}$, $R^{2a}$, $R^{3a}$, L, w and q are as defined in claim 1 and Y is a leaving group, followed by replacement of the protecting group G with $R^4$.

10. The process of claim 9 where the protecting group G is t-butoxycarbonyl or benzyloxycarbonyl and Y is chlorine, bromine, iodine, O-methanesulfonyl or O-(p-toluenesulfonyl).

11. A method for increasing levels of endogenous growth hormone in a human or an animal which comprises administering to such human or animal an effective amount of a compound of claim 1.

12. A composition useful for increasing the endogenous production or release of growth hormone in a human or an animal which comprises an inert carrier and an effective amount of a compound of claim 1.

13. A composition useful for increasing the endogenous production/release of growth hormone in a human or an animal which comprises an inert carrier and an effective amount of a compound of claim I used in combination with other growth hormone secretagogues such as GHRP-6, GHRP-1, GHRP-2, B-HT 920 or growth hormone releasing factor (GRF) or one of its analogs, or IGF-1 or IGF-2.

14. A method for the treatment of obesity which comprises administering to an obese patient a compound of claim 1 in combination with an $\alpha_2$ adrenergic agonist or $\beta_3$ adrenergic agonist.

15. A composition for the treatment of obesity which comprises an inert carrier and a compound of claim 1 in combination with an $\alpha_2$ adrenergic agonist or $\beta_3$ adrenergic agonist.

16. A method for the treatment of osteoporosis which comprises administering to a patient with osteoporosis a compound of claim 1 in combination with parathyroid hormone or a bisphosphonate.

17. A composition for the treatment of osteoporosis which comprises an inert carrier and a compound of claim 1 in combination with parathyroid hormone or a bisphosphonate.

18. A method for the treatment of the catabolic effects of nitrogen wasting which comprises administering to such patient a compound of claim 1 in combination with insulin-like growth factor I (IGF-I).

19. A composition for the treatment of the catabolic effects of nitrogen wasting which comprises an inert carrier and a compound of claim 1 in combination with insulin-like growth factor I (IGF-I).

* * * * *